United States Patent
Dietrich et al.

(10) Patent No.: US 11,680,280 B2
(45) Date of Patent: Jun. 20, 2023

(54) RECOMBINANT HOST CELLS AND METHODS FOR THE PRODUCTION OF ISOBUTYRIC ACID

(71) Applicant: Lygos, Inc., Berkeley, CA (US)

(72) Inventors: Jeffrey Dietrich, Berkeley, CA (US); Mario Ouellet, Berkeley, CA (US); Andrew Jonathan Conley, Berkeley, CA (US)

(73) Assignee: LYGOS, INC., Berkeley, CA (US)

( * ) Notice: Subject to any disclaimer, the term of this patent is extended or adjusted under 35 U.S.C. 154(b) by 0 days.

(21) Appl. No.: 16/961,057

(22) PCT Filed: Jan. 9, 2019

(86) PCT No.: PCT/US2019/012891
§ 371 (c)(1),
(2) Date: Jul. 9, 2020

(87) PCT Pub. No.: WO2019/139981
PCT Pub. Date: Jul. 18, 2019

(65) Prior Publication Data
US 2020/0370075 A1    Nov. 26, 2020

Related U.S. Application Data

(60) Provisional application No. 62/615,202, filed on Jan. 9, 2018.

(51) Int. Cl.
*C12P 7/52* (2006.01)

(52) U.S. Cl.
CPC .......... *C12P 7/52* (2013.01); *C12Y 101/01086* (2013.01); *C12Y 102/01005* (2013.01); *C12Y 202/01006* (2013.01); *C12Y 401/01072* (2013.01); *C12Y 402/01009* (2013.01)

(58) Field of Classification Search
None
See application file for complete search history.

(56) References Cited

U.S. PATENT DOCUMENTS

| | | |
|---|---|---|
| 2010/0120105 A1 | 5/2010 | Anthony et al. |
| 2011/0244536 A1 | 10/2011 | Nagarajan et al. |
| 2014/0065697 A1 | 3/2014 | Zhang et al. |

FOREIGN PATENT DOCUMENTS

| | | |
|---|---|---|
| WO | 2013016724 A2 | 1/2013 |
| WO | 2013043801 A1 | 3/2013 |
| WO | 2014039060 A1 | 3/2014 |
| WO | 2017194696 A1 | 11/2017 |

OTHER PUBLICATIONS

Chica et al. CurrOpin Biotechnol. Aug. 2005;16(4):378-84. (Year: 2005).*
Singh et al. Curr Protein PeptSci. 2017, 18, 1-11 (Year: 2017).*
Kizer et al. Appl Environ Microbiol. May 2008;74(10):3229-41. (Year: 2008).*
Prather et al. CurrOpin Biotechnol. Oct. 2008;19(5):468-74. (Year: 2008).*
Accession Q04789. Feb. 1, 1994 (Year: 1994).*
Accession R9CG82. Jul. 24, 2013 (Year: 2013).*
Accession C4ZZ44. Sep. 22, 2009 (Year: 2009).*
Accession Q02139. Jul. 1, 1993 (Year: 1993).*
Accession Q684J7. Oct. 11, 2004 (Year: 2004).*
Accession P80668. Oct. 1, 1996 (Year: 1996).*
Accession A0A099P4E1. Jan. 7, 2015 (Year: 2015).*
Accession Q9CIG9. Jun. 1, 2001 (Year: 2001).*
Accession AZW62852. Jul. 19, 2012 (Year: 2012).*
Search Report and Written Opinion issued in PCT/US2019/012891, dated Apr. 15, 2019, 15 pages.

\* cited by examiner

*Primary Examiner* — Christian L Fronda
(74) *Attorney, Agent, or Firm* — Faegre Drinker Biddle & Reath LLP

(57) ABSTRACT

Methods and materials related to producing isobutyric acid are disclosed. Specifically, isolated nucleic acids, polypeptides, host cells, methods and materials for producing isobutyric by direct microbial fermentation from a carbon source are disclosed.

17 Claims, 1 Drawing Sheet
Specification includes a Sequence Listing.

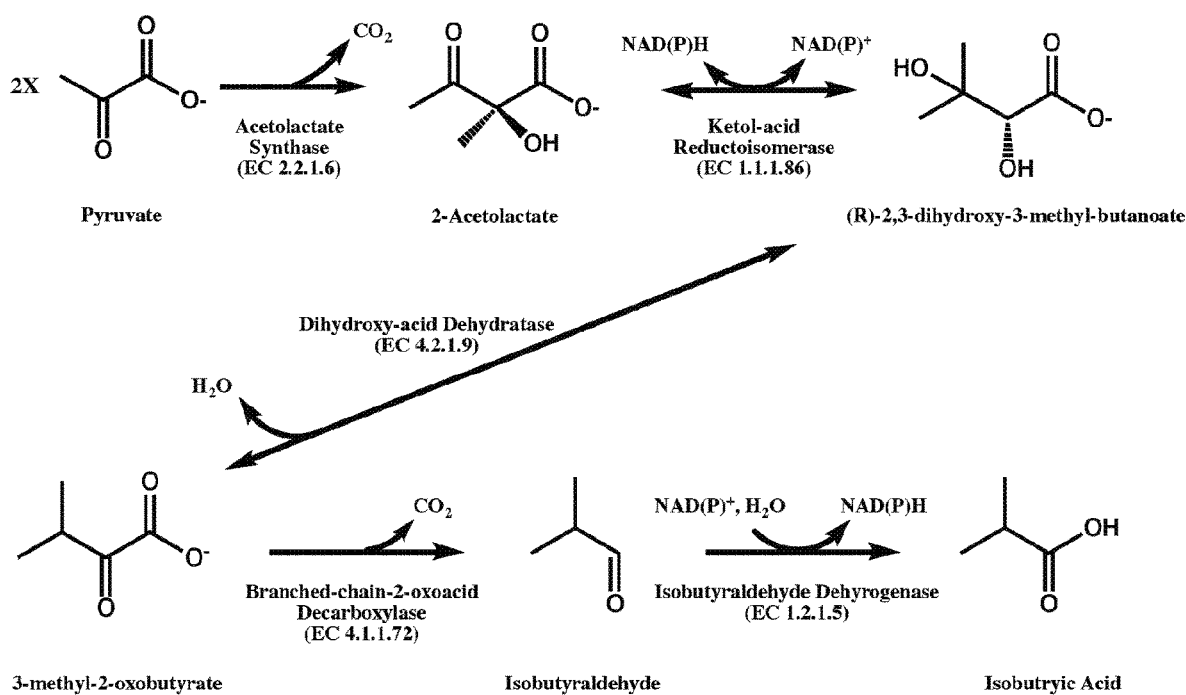

SEQUENCE LISTING

```
<160> NUMBER OF SEQ ID NOS: 24

<210> SEQ ID NO 1
<211> LENGTH: 570
<212> TYPE: PRT
<213> ORGANISM: Bacillus subtilis

<400> SEQUENCE: 1

Met Thr Lys Ala Thr Lys Glu Gln Lys Ser Leu Val Lys Asn Arg Gly
1               5                   10                  15

Ala Glu Leu Val Val Asp Cys Leu Val Glu Gln Gly Val Thr His Val
```

```
                20                  25                  30
Phe Gly Ile Pro Gly Ala Lys Ile Asp Ala Val Phe Asp Ala Leu Gln
            35                  40                  45
Asp Lys Gly Pro Glu Ile Ile Val Ala Arg His Glu Gln Asn Ala Ala
 50                  55                  60
Phe Met Ala Gln Ala Val Gly Arg Leu Thr Gly Lys Pro Gly Val Val
 65                  70                  75                  80
Leu Val Thr Ser Gly Pro Gly Ala Ser Asn Leu Ala Thr Gly Leu Leu
            85                  90                  95
Thr Ala Asn Thr Glu Gly Asp Pro Val Val Ala Leu Ala Gly Asn Val
            100                 105                 110
Ile Arg Ala Asp Arg Leu Lys Arg Thr His Gln Ser Leu Asp Asn Ala
            115                 120                 125
Ala Leu Phe Gln Pro Ile Thr Lys Tyr Ser Val Glu Val Gln Asp Val
            130                 135                 140
Lys Asn Ile Pro Glu Ala Val Thr Asn Ala Phe Arg Ile Ala Ser Ala
145                 150                 155                 160
Gly Gln Ala Gly Ala Ala Phe Val Ser Phe Pro Gln Asp Val Val Asn
            165                 170                 175
Glu Val Thr Asn Thr Lys Asn Val Arg Ala Val Ala Ala Pro Lys Leu
            180                 185                 190
Gly Pro Ala Ala Asp Asp Ala Ile Ser Ala Ala Ile Ala Lys Ile Gln
            195                 200                 205
Thr Ala Lys Leu Pro Val Val Leu Val Gly Met Lys Gly Gly Arg Pro
            210                 215                 220
Glu Ala Ile Lys Ala Val Arg Lys Leu Leu Lys Lys Val Gln Leu Pro
225                 230                 235                 240
Phe Val Glu Thr Tyr Gln Ala Ala Gly Thr Leu Ser Arg Asp Leu Glu
            245                 250                 255
Asp Gln Tyr Phe Gly Arg Ile Gly Leu Phe Arg Asn Gln Pro Gly Asp
            260                 265                 270
Leu Leu Leu Glu Gln Ala Asp Val Val Leu Thr Ile Gly Tyr Asp Pro
            275                 280                 285
Ile Glu Tyr Asp Pro Lys Phe Trp Asn Ile Asn Gly Asp Arg Thr Ile
            290                 295                 300
Ile His Leu Asp Glu Ile Ile Ala Asp Ile Asp His Ala Tyr Gln Pro
305                 310                 315                 320
Asp Leu Glu Leu Ile Gly Asp Ile Pro Ser Thr Ile Asn His Ile Glu
            325                 330                 335
His Asp Ala Val Lys Val Glu Phe Ala Glu Arg Glu Gln Lys Ile Leu
            340                 345                 350
Ser Asp Leu Lys Gln Tyr Met His Glu Gly Glu Gln Val Pro Ala Asp
            355                 360                 365
Trp Lys Ser Asp Arg Ala His Pro Leu Glu Ile Val Lys Glu Leu Arg
            370                 375                 380
Asn Ala Val Asp Asp His Val Thr Val Thr Cys Asp Ile Gly Ser His
385                 390                 395                 400
Ala Ile Trp Met Ser Arg Tyr Phe Arg Ser Tyr Glu Pro Leu Thr Leu
            405                 410                 415
Met Ile Ser Asn Gly Met Gln Thr Leu Gly Val Ala Leu Pro Trp Ala
            420                 425                 430
Ile Gly Ala Ser Leu Val Lys Pro Gly Glu Lys Val Val Ser Val Ser
            435                 440                 445
```

```
Gly Asp Gly Gly Phe Leu Phe Ser Ala Met Glu Leu Glu Thr Ala Val
        450                 455                 460

Arg Leu Lys Ala Pro Ile Val His Ile Val Trp Asn Asp Ser Thr Tyr
465                 470                 475                 480

Asp Met Val Ala Phe Gln Gln Leu Lys Lys Tyr Asn Arg Thr Ser Ala
                485                 490                 495

Val Asp Phe Gly Asn Ile Asp Ile Val Lys Tyr Ala Glu Ser Phe Gly
                500                 505                 510

Ala Thr Gly Leu Arg Val Glu Ser Pro Asp Gln Leu Ala Asp Val Leu
        515                 520                 525

Arg Gln Gly Met Asn Ala Glu Gly Pro Val Ile Ile Asp Val Pro Val
530                 535                 540

Asp Tyr Ser Asp Asn Ile Asn Leu Ala Ser Asp Lys Leu Pro Lys Glu
545                 550                 555                 560

Phe Gly Glu Leu Met Lys Thr Lys Ala Leu
                565                 570

<210> SEQ ID NO 2
<211> LENGTH: 491
<212> TYPE: PRT
<213> ORGANISM: Escherichia coli

<400> SEQUENCE: 2

Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
                20                  25                  30

Ser Tyr Leu Gln Gly Lys Lys Val Val Ile Val Gly Cys Gly Ala Gln
            35                  40                  45

Gly Leu Asn Gln Gly Leu Asn Met Arg Asp Ser Gly Leu Asp Ile Ser
        50                  55                  60

Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Gln His Ser
                100                 105                 110

Asp Val Val Arg Thr Val Gln Pro Leu Met Lys Asp Gly Ala Ala Leu
            115                 120                 125

Gly Tyr Ser His Gly Phe Asn Ile Val Glu Val Gly Glu Gln Ile Arg
        130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
                180                 185                 190

Ala Trp Ala Ala Ala Thr Gly Gly His Arg Ala Gly Val Leu Glu Ser
            195                 200                 205

Ser Phe Val Ala Glu Val Lys Ser Asp Leu Met Gly Glu Gln Thr Ile
        210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
```

```
                    245                 250                 255
Gly Trp Glu Thr Ile Thr Glu Ala Leu Lys Gln Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
                485                 490

<210> SEQ ID NO 3
<211> LENGTH: 570
<212> TYPE: PRT
<213> ORGANISM: Lactococcus lactis

<400> SEQUENCE: 3

Met Glu Phe Lys Tyr Asn Gly Lys Val Glu Ser Val Glu Leu Asn Lys
1               5                   10                  15

Tyr Ser Lys Thr Leu Thr Gln Asp Pro Thr Gln Pro Ala Thr Gln Ala
            20                  25                  30

Met Tyr Tyr Gly Ile Gly Phe Lys Asp Glu Asp Phe Lys Lys Ala Gln
        35                  40                  45

Val Gly Ile Val Ser Met Asp Trp Asp Gly Asn Pro Cys Asn Met His
    50                  55                  60

Leu Gly Thr Leu Gly Ser Lys Ile Lys Ser Ser Val Asn Gln Thr Asp
65                  70                  75                  80

Gly Leu Ile Gly Leu Gln Phe His Thr Ile Gly Val Ser Asp Gly Ile
                85                  90                  95

Ala Asn Gly Lys Leu Gly Met Arg Tyr Ser Leu Val Ser Arg Glu Val
            100                 105                 110

Ile Ala Asp Ser Ile Glu Thr Asn Ala Gly Ala Glu Tyr Tyr Asp Ala
        115                 120                 125
```

-continued

```
Ile Val Ala Ile Pro Gly Cys Asp Lys Asn Met Pro Gly Ser Ile Ile
130                 135                 140
Gly Met Ala Arg Leu Asn Arg Pro Ser Ile Met Val Tyr Gly Gly Thr
145                 150                 155                 160
Ile Glu His Gly Glu Tyr Lys Gly Glu Lys Leu Asn Ile Val Ser Ala
                165                 170                 175
Phe Glu Ser Leu Gly Gln Lys Ile Thr Gly Asn Ile Ser Asp Glu Asp
            180                 185                 190
Tyr His Gly Val Ile Cys Asn Ala Ile Pro Gly Gln Gly Ala Cys Gly
        195                 200                 205
Gly Met Tyr Thr Ala Asn Thr Leu Ala Ala Ile Glu Thr Leu Gly
210                 215                 220
Met Ser Leu Pro Tyr Ser Ser Asn Pro Ala Val Ser Gln Glu Lys
225                 230                 235                 240
Gln Glu Glu Cys Asp Glu Ile Gly Leu Ala Ile Lys Asn Leu Leu Glu
                245                 250                 255
Lys Asp Ile Lys Pro Ser Asp Ile Met Thr Lys Glu Ala Phe Glu Asn
            260                 265                 270
Ala Ile Thr Ile Val Met Val Leu Gly Gly Ser Thr Asn Ala Val Leu
        275                 280                 285
His Ile Ile Ala Met Ala Asn Ala Ile Gly Val Glu Ile Thr Gln Asp
    290                 295                 300
Asp Phe Gln Arg Ile Ser Asp Ile Thr Pro Val Leu Gly Asp Phe Lys
305                 310                 315                 320
Pro Ser Gly Lys Tyr Met Met Glu Asp Leu His Lys Ile Gly Gly Leu
                325                 330                 335
Pro Ala Val Leu Lys Tyr Leu Leu Lys Glu Gly Lys Leu His Gly Asp
            340                 345                 350
Cys Leu Thr Val Thr Gly Lys Thr Leu Ala Glu Asn Val Glu Thr Ala
        355                 360                 365
Leu Asp Leu Asp Phe Asp Ser Gln Asp Ile Met Arg Pro Leu Lys Asn
    370                 375                 380
Pro Ile Lys Ala Thr Gly His Leu Gln Ile Leu Tyr Gly Asn Leu Ala
385                 390                 395                 400
Gln Gly Gly Ser Val Ala Lys Ile Ser Gly Lys Glu Gly Glu Phe Phe
                405                 410                 415
Lys Gly Thr Ala Arg Val Phe Asp Gly Glu Gln His Phe Ile Asp Gly
            420                 425                 430
Ile Glu Ser Gly Arg Leu His Ala Gly Asp Val Ala Val Ile Arg Asn
        435                 440                 445
Ile Gly Pro Val Gly Gly Pro Gly Met Pro Glu Met Leu Lys Pro Thr
    450                 455                 460
Ser Ala Leu Ile Gly Ala Gly Leu Gly Lys Ser Cys Ala Leu Ile Thr
465                 470                 475                 480
Asp Gly Arg Phe Ser Gly Thr His Gly Phe Val Val Gly His Ile
                485                 490                 495
Val Pro Glu Ala Val Glu Gly Gly Leu Ile Gly Leu Val Glu Asp Asp
            500                 505                 510
Asp Ile Ile Glu Ile Asp Ala Val Asn Asn Ser Ile Ser Leu Lys Val
        515                 520                 525
Ser Asp Glu Glu Ile Ala Lys Arg Arg Ala Asn Tyr Gln Lys Pro Thr
    530                 535                 540
Pro Lys Ala Thr Arg Gly Val Leu Ala Lys Phe Ala Lys Leu Thr Arg
```

```
                545                 550                 555                 560
Pro Ala Ser Glu Gly Cys Val Thr Asp Leu
                    565                 570

<210> SEQ ID NO 4
<211> LENGTH: 548
<212> TYPE: PRT
<213> ORGANISM: Lactococcus lactis

<400> SEQUENCE: 4

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
    290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350
```

```
Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                    405                 410                 415

Ala Asp Lys Glu Ser Arg His Leu Phe Ile Gly Asp Gly Ser Leu
                420                 425                 430

Gln Leu Thr Val Gln Glu Leu Gly Leu Ala Ile Arg Glu Lys Ile Asn
        435                 440                 445

Pro Ile Cys Phe Ile Ile Asn Asn Asp Gly Tyr Thr Val Glu Arg Glu
450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
                500                 505                 510

Gln Ala Asp Pro Asn Arg Met Tyr Trp Ile Glu Leu Ile Leu Ala Lys
        515                 520                 525

Glu Gly Ala Pro Lys Val Leu Lys Lys Met Gly Lys Leu Phe Ala Glu
530                 535                 540

Gln Asn Lys Ser
545

<210> SEQ ID NO 5
<211> LENGTH: 499
<212> TYPE: PRT
<213> ORGANISM: Escherichia coli

<400> SEQUENCE: 5

Met Thr Glu Pro His Val Ala Val Leu Ser Gln Val Gln Gln Phe Leu
1               5                   10                  15

Asp Arg Gln His Gly Leu Tyr Ile Asp Gly Arg Pro Gly Pro Ala Gln
                20                  25                  30

Ser Glu Lys Arg Leu Ala Ile Phe Asp Pro Ala Thr Gly Gln Glu Ile
            35                  40                  45

Ala Ser Thr Ala Asp Ala Asn Glu Ala Asp Val Asp Asn Ala Val Met
50                  55                  60

Ser Ala Trp Arg Ala Phe Val Ser Arg Arg Trp Ala Gly Arg Leu Pro
65                  70                  75                  80

Ala Glu Arg Glu Arg Ile Leu Leu Arg Phe Ala Asp Leu Val Glu Gln
                85                  90                  95

His Ser Glu Glu Leu Ala Gln Leu Glu Thr Leu Glu Gln Gly Lys Ser
            100                 105                 110

Ile Ala Ile Ser Arg Ala Phe Glu Val Gly Cys Thr Leu Asn Trp Met
        115                 120                 125

Arg Tyr Thr Ala Gly Leu Thr Thr Lys Ile Ala Gly Lys Thr Leu Asp
130                 135                 140

Leu Ser Ile Pro Leu Pro Gln Gly Ala Arg Tyr Gln Ala Trp Thr Arg
145                 150                 155                 160

Lys Glu Pro Val Gly Val Val Ala Gly Ile Val Pro Trp Asn Phe Pro
                165                 170                 175
```

Leu Met Ile Gly Met Trp Lys Val Met Pro Ala Leu Ala Ala Gly Cys
            180                 185                 190

Ser Ile Val Ile Lys Pro Ser Glu Thr Thr Pro Leu Thr Met Leu Arg
        195                 200                 205

Val Ala Glu Leu Ala Ser Glu Ala Gly Ile Pro Asp Gly Val Phe Asn
    210                 215                 220

Val Val Thr Gly Ser Gly Ala Val Cys Gly Ala Ala Leu Thr Ser His
225                 230                 235                 240

Pro His Val Ala Lys Ile Ser Phe Thr Gly Ser Thr Ala Thr Gly Lys
                245                 250                 255

Gly Ile Ala Arg Thr Ala Ala Asp His Leu Thr Arg Val Thr Leu Glu
            260                 265                 270

Leu Gly Gly Lys Asn Pro Ala Ile Val Leu Lys Asp Ala Asp Pro Gln
        275                 280                 285

Trp Val Ile Glu Gly Leu Met Thr Gly Ser Phe Leu Asn Gln Gly Gln
    290                 295                 300

Val Cys Ala Ala Ser Ser Arg Ile Tyr Ile Glu Ala Pro Leu Phe Asp
305                 310                 315                 320

Thr Leu Val Ser Gly Phe Glu Gln Ala Val Lys Ser Leu Gln Val Gly
                325                 330                 335

Pro Gly Met Ser Pro Val Ala Gln Ile Asn Pro Leu Val Ser Arg Ala
            340                 345                 350

His Cys Asp Lys Val Cys Ser Phe Leu Asp Asp Ala Gln Ala Gln Gln
        355                 360                 365

Ala Glu Leu Ile Arg Gly Ser Asn Gly Pro Ala Gly Glu Gly Tyr Tyr
    370                 375                 380

Val Ala Pro Thr Leu Val Val Asn Pro Asp Ala Lys Leu Arg Leu Thr
385                 390                 395                 400

Arg Glu Glu Val Phe Gly Pro Val Val Asn Leu Val Arg Val Ala Asp
                405                 410                 415

Gly Glu Glu Ala Leu Gln Leu Ala Asn Asp Thr Glu Tyr Gly Leu Thr
            420                 425                 430

Ala Ser Val Trp Thr Gln Asn Leu Ser Gln Ala Leu Glu Tyr Ser Asp
        435                 440                 445

Arg Leu Gln Ala Gly Thr Val Trp Val Asn Ser His Thr Leu Ile Asp
    450                 455                 460

Ala Asn Leu Pro Phe Gly Gly Met Lys Gln Ser Gly Thr Gly Arg Asp
465                 470                 475                 480

Phe Gly Pro Asp Trp Leu Asp Gly Trp Cys Glu Thr Lys Ser Val Cys
                485                 490                 495

Val Arg Tyr

<210> SEQ ID NO 6
<211> LENGTH: 563
<212> TYPE: PRT
<213> ORGANISM: Pichia kudriavzevii

<400> SEQUENCE: 6

Met Ile Pro Arg Leu Asn Pro Leu Leu Asn Ile Ser His Leu Arg Gly
1               5                   10                  15

Gly Pro Lys Phe Ile Gly Lys Ala Ile Lys Pro Ser Gln Phe Glu Phe
            20                  25                  30

Arg Lys Asn Asn Phe Arg Phe Asn Ser Thr Ser Thr Lys Thr Gly Ser
        35                  40                  45

```
Ala Arg Thr Ile Lys Ser Gly Phe Leu Ser Trp Ser Phe Arg Ala Ala
 50                  55                  60

Thr Phe Thr Gly Ile Ala Gly Trp Leu Tyr Leu Thr Tyr Leu Val Tyr
 65                      70                  75                  80

Lys Glu Thr Asn Pro Gly Ser Gln Ser Pro Gln Thr Glu Phe Ser Glu
                     85                  90                  95

Ile Gly Asn Lys Lys Asn Ile Val Ile Leu Gly Ser Gly Trp Gly
                 100                 105                 110

Ala Val Ser Val Leu Lys Thr Leu Asp Thr Thr Lys Tyr Asn Val Thr
             115                 120                 125

Ile Val Ser Pro Arg Asn Tyr Phe Leu Phe Thr Pro Leu Leu Pro Ser
 130                 135                 140

Val Pro Ser Gly Thr Ile Asp Ile Lys Ser Ile Cys Asp Ser Ile Arg
 145                 150                 155                 160

Thr Ile Ala Arg Gln Thr Pro Gly Glu Val Thr Tyr Leu Glu Ala Ala
                 165                 170                 175

Ala Thr Asp Ile Asp Pro Val Lys Lys Thr Ile Lys Leu Glu His Lys
             180                 185                 190

Ser Gln Arg Phe Leu Ile Gly Asp Ala Phe Thr Ser Glu Gly Asp Val
         195                 200                 205

Ile Glu Asn Glu Leu Ser Tyr Asp Tyr Leu Val Tyr Ala Val Gly Ala
 210                 215                 220

Thr Val Asn Thr Phe Gly Ile Pro Gly Ile Pro Glu Tyr Ala Ser Tyr
 225                 230                 235                 240

Leu Lys Glu Ala Asn Asp Ala Thr Ala Val Arg Gln Lys Leu Phe Asn
                 245                 250                 255

Gln Ile Glu Ala Ser Arg Leu Leu Pro Lys Asp Ser Gly Asp Arg Lys
             260                 265                 270

Arg Leu Leu Ser Phe Val Val Cys Gly Gly Pro Thr Gly Val Glu
         275                 280                 285

Leu Ala Ala Glu Ile Lys Asp Tyr Ile Asp Gln Asp Leu Cys Lys Phe
 290                 295                 300

Ile Pro Gly Ile Glu Lys Glu Met Gln Val Thr Leu Ile Glu Ala Gln
 305                 310                 315                 320

His Asn Val Leu Ser Met Phe His Pro Lys Leu Ile Glu Tyr Thr Lys
                 325                 330                 335

Glu Val Phe Lys Gln Gln Asn Leu His Leu Gln Val Asp Thr Met Val
             340                 345                 350

Lys Lys Val Asp Asp Lys Asn Val Tyr Ala Thr Tyr Arg His Pro Asp
         355                 360                 365

Gly Lys Thr Glu Asp Met Val Ile Pro Tyr Gly Thr Leu Val Trp Ala
 370                 375                 380

Gly Gly Asn Ala Gln Arg Lys Leu Thr Arg Asp Leu Ser Ser Lys Ile
 385                 390                 395                 400

Ile Glu Gln Lys Thr Ala Arg Arg Gly Leu Leu Val Asp Glu Tyr Leu
                 405                 410                 415

Lys Leu Asp Gly Asp Asp Ser Ile Tyr Ala Ile Gly Asp Cys Thr Phe
             420                 425                 430

Thr Pro Asn Pro Pro Thr Ala Gln Val Ala His Gln Gln Gly Glu Tyr
         435                 440                 445

Leu Gly Glu His Phe Asn Lys Leu Ala Lys Ile Asp Glu Leu Asn Tyr
 450                 455                 460
```

```
Leu Ile Thr Asn Ser Thr Asp Asp Ser Thr Lys Tyr Ser Lys Arg Leu
465                 470                 475                 480

Glu Arg Ala Glu Lys Ala Ile Lys Pro Phe Glu Tyr Asp His Gln Gly
            485                 490                 495

Ala Leu Ala Tyr Val Gly Ser Glu Arg Ala Val Ala Asp Leu His Trp
            500                 505                 510

Gly Ser Trp Ser Thr Val Ala Leu Gly Gly Thr Met Thr Phe Phe Phe
            515                 520                 525

Trp Arg Thr Ala Tyr Val Ser Met Leu Leu Ser Ile Arg Asn Lys Ile
            530                 535                 540

Leu Val Val Thr Asp Trp Val Lys Val Ala Ile Phe Gly Arg Asp Cys
545                 550                 555                 560

Ser Gln Glu

<210> SEQ ID NO 7
<211> LENGTH: 446
<212> TYPE: PRT
<213> ORGANISM: Lactococcus lactis

<400> SEQUENCE: 7

Met Lys Ile Val Val Ile Gly Thr Asn His Ala Gly Ile Ala Thr Ala
1               5                   10                  15

Asn Thr Leu Ile Asp Arg Tyr Pro Gly His Glu Ile Val Met Ile Asp
            20                  25                  30

Arg Asn Ser Asn Met Ser Tyr Leu Gly Cys Gly Thr Ala Ile Trp Val
        35                  40                  45

Gly Arg Gln Ile Glu Lys Pro Asp Glu Leu Phe Tyr Ala Lys Ala Glu
    50                  55                  60

Asp Phe Glu Lys Lys Gly Val Lys Ile Leu Thr Glu Thr Glu Val Ser
65                  70                  75                  80

Glu Ile Asp Phe Thr Asn Lys Met Ile Tyr Ala Lys Ser Lys Thr Gly
                85                  90                  95

Glu Lys Ile Thr Glu Ser Tyr Asp Lys Leu Val Leu Ala Thr Gly Ser
            100                 105                 110

Arg Pro Ile Ile Pro Asn Leu Pro Gly Lys Asp Leu Lys Gly Ile His
        115                 120                 125

Phe Leu Lys Leu Phe Gln Glu Gly Gln Ala Ile Asp Glu Glu Phe Ala
130                 135                 140

Lys Asn Asp Val Lys Arg Ile Ala Val Ile Gly Ala Gly Tyr Ile Gly
145                 150                 155                 160

Thr Glu Ile Ala Glu Ala Ala Lys Arg Arg Gly Lys Glu Val Leu Leu
                165                 170                 175

Phe Asp Ala Glu Ser Thr Ser Leu Ala Ser Tyr Tyr Asp Glu Glu Phe
            180                 185                 190

Ala Lys Gly Met Asp Glu Asn Leu Ala Gln His Gly Ile Glu Leu His
        195                 200                 205

Phe Gly Glu Leu Ala Gln Glu Phe Lys Ala Asn Glu Lys Gly His Val
    210                 215                 220

Ser Gln Ile Val Thr Asn Lys Ser Thr Tyr Asp Val Asp Leu Val Ile
225                 230                 235                 240

Asn Cys Ile Gly Phe Thr Ala Asn Ser Ala Leu Ala Gly Glu His Leu
                245                 250                 255

Glu Thr Phe Lys Asn Gly Ala Ile Lys Val Asp Lys His Gln Gln Ser
            260                 265                 270
```

```
Ser Asp Pro Asp Val Ser Ala Gly Asp Val Ala Thr Ile Tyr Ser
            275                 280                 285

Asn Ala Leu Gln Asp Phe Thr Tyr Ile Ala Leu Ala Ser Asn Ala Val
        290                 295                 300

Arg Ser Gly Ile Val Ala Gly His Asn Ile Gly Gly Lys Ser Ile Glu
305                 310                 315                 320

Ser Val Gly Val Gln Gly Ser Asn Gly Ile Ser Ile Phe Gly Tyr Asn
                325                 330                 335

Met Thr Ser Thr Gly Leu Ser Val Lys Ala Ala Lys Lys Ile Gly Leu
            340                 345                 350

Glu Val Ser Phe Ser Asp Phe Glu Asp Lys Gln Lys Ala Trp Phe Leu
        355                 360                 365

His Glu Asn Asn Asp Ser Val Lys Ile Arg Ile Val Tyr Glu Thr Lys
    370                 375                 380

Asn Arg Arg Ile Ile Gly Ala Gln Leu Ala Ser Lys Ser Glu Ile Ile
385                 390                 395                 400

Ala Gly Asn Ile Asn Met Phe Ser Leu Ala Ile Gln Glu Lys Lys Thr
                405                 410                 415

Ile Asp Glu Leu Ala Leu Leu Asp Leu Phe Phe Leu Pro His Phe Asn
            420                 425                 430

Ser Pro Tyr Asn Tyr Met Thr Val Ala Ala Leu Asn Ala Lys
        435                 440                 445

<210> SEQ ID NO 8
<211> LENGTH: 575
<212> TYPE: PRT
<213> ORGANISM: Pichia kudriavzevii

<400> SEQUENCE: 8

Met Thr Asp Lys Ile Ser Leu Gly Thr Tyr Leu Phe Glu Lys Leu Lys
1               5                   10                  15

Glu Ala Gly Ser Tyr Ser Ile Phe Gly Val Pro Gly Asp Phe Asn Leu
                20                  25                  30

Ala Leu Leu Asp His Val Lys Glu Val Glu Gly Ile Arg Trp Val Gly
            35                  40                  45

Asn Ala Asn Glu Leu Asn Ala Gly Tyr Glu Ala Asp Gly Tyr Ala Arg
        50                  55                  60

Ile Asn Gly Phe Ala Ser Leu Ile Thr Thr Phe Gly Val Gly Glu Leu
65                  70                  75                  80

Ser Ala Val Asn Ala Ile Ala Gly Ser Tyr Ala Glu His Val Pro Leu
                85                  90                  95

Ile His Ile Val Gly Met Pro Ser Leu Ser Ala Met Lys Asn Asn Leu
            100                 105                 110

Leu Leu His His Thr Leu Gly Asp Thr Arg Phe Asp Asn Phe Thr Glu
        115                 120                 125

Met Ser Lys Lys Ile Ser Ala Lys Val Glu Ile Val Tyr Asp Leu Glu
    130                 135                 140

Ser Ala Pro Lys Leu Ile Asn Asn Leu Ile Glu Thr Ala Tyr His Thr
145                 150                 155                 160

Lys Arg Pro Val Tyr Leu Gly Leu Pro Ser Asn Phe Ala Asp Glu Leu
                165                 170                 175

Val Pro Ala Ala Leu Val Lys Glu Asn Lys Leu His Leu Glu Glu Pro
            180                 185                 190

Leu Asn Asn Pro Val Ala Glu Glu Glu Phe Ile His Asn Val Val Glu
        195                 200                 205
```

Met Val Lys Lys Ala Glu Lys Pro Ile Ile Leu Val Asp Ala Cys Ala
210                 215                 220

Ala Arg His Asn Ile Ser Lys Glu Val Arg Glu Leu Ala Lys Leu Thr
225                 230                 235                 240

Lys Phe Pro Val Phe Thr Thr Pro Met Gly Lys Ser Thr Val Asp Glu
                245                 250                 255

Asp Asp Glu Glu Phe Phe Gly Leu Tyr Leu Gly Ser Leu Ser Ala Pro
                260                 265                 270

Asp Val Lys Asp Ile Val Gly Pro Thr Asp Cys Ile Leu Ser Leu Gly
            275                 280                 285

Gly Leu Pro Ser Asp Phe Asn Thr Gly Ser Phe Ser Tyr Gly Tyr Thr
    290                 295                 300

Thr Lys Asn Val Val Glu Phe His Ser Asn Tyr Cys Lys Phe Lys Ser
305                 310                 315                 320

Ala Thr Tyr Glu Asn Leu Met Met Lys Gly Ala Val Gln Arg Leu Ile
                325                 330                 335

Ser Glu Leu Lys Asn Ile Lys Tyr Ser Asn Val Ser Thr Leu Ser Pro
                340                 345                 350

Pro Lys Ser Lys Phe Ala Tyr Glu Ser Ala Lys Val Ala Pro Glu Gly
            355                 360                 365

Ile Ile Thr Gln Asp Tyr Leu Trp Lys Arg Leu Ser Tyr Phe Leu Lys
    370                 375                 380

Pro Arg Asp Ile Ile Val Thr Glu Thr Gly Thr Ser Ser Phe Gly Val
385                 390                 395                 400

Leu Ala Thr His Leu Pro Arg Asp Ser Lys Ser Ile Ser Gln Val Leu
                405                 410                 415

Trp Gly Ser Ile Gly Phe Ser Leu Pro Ala Ala Val Gly Ala Ala Phe
                420                 425                 430

Ala Ala Glu Asp Ala His Lys Gln Thr Gly Glu Gln Glu Arg Arg Thr
            435                 440                 445

Val Leu Phe Ile Gly Asp Gly Ser Leu Gln Leu Thr Val Gln Ser Ile
    450                 455                 460

Ser Asp Ala Ala Arg Trp Asn Ile Lys Pro Tyr Ile Phe Ile Leu Asn
465                 470                 475                 480

Asn Arg Gly Tyr Thr Ile Glu Lys Leu Ile His Gly Arg His Glu Asp
                485                 490                 495

Tyr Asn Gln Ile Gln Pro Trp Asp His Gln Leu Leu Leu Lys Leu Phe
                500                 505                 510

Ala Asp Lys Thr Gln Tyr Glu Asn His Val Val Lys Ser Ala Lys Asp
            515                 520                 525

Leu Asp Ala Leu Met Lys Asp Glu Ala Phe Asn Lys Glu Asp Lys Ile
    530                 535                 540

Arg Val Ile Glu Leu Phe Leu Asp Glu Phe Asp Ala Pro Glu Ile Leu
545                 550                 555                 560

Val Ala Gln Ala Lys Leu Ser Asp Glu Ile Asn Ser Lys Ala Ala
                565                 570                 575

<210> SEQ ID NO 9
<211> LENGTH: 608
<212> TYPE: PRT
<213> ORGANISM: Pichia kudriavzevii

<400> SEQUENCE: 9

Met Leu Gln Thr Ala Asn Ser Glu Val Pro Asn Ala Ser Gln Ile Thr

-continued

```
1               5                   10                  15
Ile Asp Ala Ala Ser Gly Leu Pro Ala Asp Arg Val Leu Pro Asn Ile
                20                  25                  30

Thr Asn Thr Glu Ile Thr Ile Ser Glu Tyr Ile Phe Tyr Arg Ile Leu
                35                  40                  45

Gln Leu Gly Val Arg Ser Val Phe Gly Val Pro Gly Asp Phe Asn Leu
                50                  55                  60

Arg Phe Leu Glu His Ile Tyr Asp Val His Gly Leu Asn Trp Ile Gly
65                  70                  75                  80

Cys Cys Asn Glu Leu Asn Ala Ala Tyr Ala Ala Asp Ala Tyr Ala Lys
                85                  90                  95

Ala Ser Lys Lys Met Gly Val Leu Leu Thr Thr Tyr Gly Val Gly Glu
                100                 105                 110

Leu Ser Ala Leu Asn Gly Val Ala Gly Ala Tyr Thr Glu Phe Ala Pro
                115                 120                 125

Val Leu His Leu Val Gly Thr Ser Ala Leu Lys Phe Lys Arg Asn Pro
                130                 135                 140

Arg Thr Leu Asn Leu His His Leu Ala Gly Asp Lys Lys Thr Phe Lys
145                 150                 155                 160

Lys Ser Asp His Tyr Lys Tyr Glu Arg Ile Ala Ser Glu Phe Ser Val
                165                 170                 175

Asp Ser Ala Ser Ile Glu Asp Pro Ile Glu Ala Cys Glu Met Ile
                180                 185                 190

Asp Arg Val Ile Tyr Ser Thr Trp Arg Glu Ser Arg Pro Gly Tyr Ile
                195                 200                 205

Phe Leu Pro Cys Asp Leu Ser Glu Met Lys Val Asp Ala Gln Arg Leu
210                 215                 220

Ala Ser Pro Ile Glu Leu Thr Tyr Arg Phe Asn Ser Pro Val Ser Arg
225                 230                 235                 240

Val Glu Gly Val Ala Asp Gln Ile Leu Gln Leu Ile Tyr Gln Asn Lys
                245                 250                 255

Asn Val Ser Ile Ile Val Asp Gly Phe Ile Arg Lys Phe Arg Met Glu
                260                 265                 270

Ser Glu Phe Tyr Asp Ile Met Glu Lys Phe Gly Asp Lys Val Asn Ile
                275                 280                 285

Phe Ser Thr Met Tyr Gly Lys Gly Leu Ile Gly Glu Glu His Pro Arg
290                 295                 300

Phe Val Gly Thr Tyr Phe Gly Lys Tyr Glu Lys Ala Val Gly Asn Leu
305                 310                 315                 320

Leu Glu Ala Ser Asp Leu Ile Ile His Phe Gly Asn Phe Asp His Glu
                325                 330                 335

Leu Asn Met Gly Gly Phe Thr Phe Asn Ile Pro Gln Glu Lys Tyr Ile
                340                 345                 350

Asp Leu Ser Ala Gln Tyr Val Asp Ile Thr Gly Asn Leu Asp Glu Ser
                355                 360                 365

Ile Thr Met Met Glu Val Leu Pro Val Leu Ala Ser Lys Leu Asp Ser
                370                 375                 380

Ser Arg Val Asn Val Ala Asp Lys Phe Glu Lys Phe Asp Lys Tyr Tyr
385                 390                 395                 400

Glu Thr Pro Asp Tyr Gln Arg Glu Ala Ser Leu Gln Glu Thr Asp Ile
                405                 410                 415

Met Gln Ser Leu Asn Glu Asn Leu Thr Gly Asp Asp Ile Leu Ile Val
                420                 425                 430
```

-continued

```
Glu Thr Cys Ser Phe Leu Phe Ala Val Pro Asp Leu Lys Val Lys Gln
            435                 440                 445

His Thr Asn Ile Ile Leu Gln Ala Tyr Trp Ala Ser Ile Gly Tyr Ala
        450                 455                 460

Leu Pro Ala Thr Leu Gly Ala Ser Leu Ala Ile Arg Asp Phe Asn Leu
465                 470                 475                 480

Ser Gly Lys Val Tyr Thr Ile Glu Gly Asp Gly Ser Ala Gln Met Ser
                485                 490                 495

Leu Gln Glu Leu Ser Ser Met Leu Arg Tyr Asn Ile Asp Ala Thr Met
            500                 505                 510

Ile Leu Leu Asn Asn Ser Gly Tyr Thr Ile Glu Arg Val Ile Val Gly
        515                 520                 525

Pro His Ser Ser Tyr Asn Asp Ile Asn Thr Asn Trp Gln Trp Thr Asp
    530                 535                 540

Leu Leu Arg Ala Phe Gly Asp Val Ala Asn Glu Lys Ser Val Ser Tyr
545                 550                 555                 560

Thr Ile Lys Glu Arg Glu Gln Leu Leu Asn Ile Leu Ser Asp Pro Ser
                565                 570                 575

Phe Lys His Asn Gly Lys Phe Arg Leu Leu Glu Cys Val Leu Pro Met
            580                 585                 590

Phe Asp Val Pro Lys Lys Leu Gly Gln Phe Thr Gly Lys Ile Pro Ala
        595                 600                 605

<210> SEQ ID NO 10
<211> LENGTH: 584
<212> TYPE: PRT
<213> ORGANISM: Pichia kudriavzevii

<400> SEQUENCE: 10

Met Ala Pro Val Ser Leu Glu Thr Cys Thr Leu Glu Phe Ser Cys Lys
1               5                   10                  15

Leu Pro Leu Ser Glu Tyr Ile Phe Arg Arg Ile Ala Ser Leu Gly Ile
            20                  25                  30

His Asn Ile Phe Gly Val Pro Gly Asp Tyr Asn Leu Ser Phe Leu Glu
        35                  40                  45

His Leu Tyr Ser Val Pro Glu Leu Ser Trp Val Gly Cys Cys Asn Glu
    50                  55                  60

Leu Asn Ser Ala Tyr Ala Thr Asp Gly Tyr Ser Arg Thr Ile Gly His
65                  70                  75                  80

Asp Lys Phe Gly Val Leu Leu Thr Thr Gln Gly Val Gly Glu Leu Ser
                85                  90                  95

Ala Ala Asn Ala Ile Ala Gly Ser Phe Ala Glu His Val Pro Ile Leu
            100                 105                 110

His Ile Val Gly Thr Thr Pro Tyr Ser Leu Lys His Lys Gly Ser His
        115                 120                 125

His His His Leu Ile Asn Gly Val Ser Thr Arg Glu Pro Thr Asn His
    130                 135                 140

Tyr Ala Tyr Glu Glu Met Ser Lys Asn Ile Ser Cys Lys Ile Leu Ser
145                 150                 155                 160

Leu Ser Asp Asp Leu Thr Asn Ala Ala Asn Glu Ile Asp Asp Leu Phe
                165                 170                 175

Arg Thr Ile Leu Met Leu Lys Lys Pro Gly Tyr Leu Tyr Ile Pro Cys
            180                 185                 190

Asp Leu Val Asn Val Glu Ile Asp Ala Ser Asn Leu Gln Ser Val Pro
```

```
                    195                 200                 205
Ala Asn Lys Leu Arg Glu Arg Val Pro Ser Thr Asp Ser Gln Thr Ile
210                 215                 220

Ala Lys Ile Thr Ser Thr Ile Val Asp Lys Leu Leu Ser Ser Ser Asn
225                 230                 235                 240

Pro Val Val Leu Cys Asp Ile Leu Thr Asp Arg Tyr Gly Met Thr Ala
                245                 250                 255

Tyr Ala Gln Asp Leu Val Asp Ser Leu Lys Val Pro Cys Cys Asn Ser
                260                 265                 270

Phe Met Gly Lys Ala Leu Leu Asn Glu Ser Lys Glu His Tyr Ile Gly
                275                 280                 285

Asp Phe Asn Gly Glu Glu Ser Asn Lys Met Val His Ser Tyr Ile Ser
290                 295                 300

Asn Thr Asp Cys Phe Leu His Ile Gly Asp Tyr Tyr Asn Glu Ile Asn
305                 310                 315                 320

Ser Gly His Trp Ser Leu Tyr Asn Gly Ile Asn Lys Glu Ser Ile Val
                325                 330                 335

Ile Leu Asn Pro Glu Tyr Val Lys Ile Gly Ser Gln Thr Tyr Gln Asn
                340                 345                 350

Val Ser Phe Glu Asp Ile Leu Pro Ala Ile Leu Ser Ser Ile Lys Ala
                355                 360                 365

Asn Pro Asn Leu Pro Cys Phe His Ile Pro Lys Ile Met Ser Thr Ile
370                 375                 380

Glu Gln Ile Pro Ser Asn Thr Pro Ile Ser Gln Thr Leu Met Leu Glu
385                 390                 395                 400

Lys Leu Gln Ser Phe Leu Lys Pro Asn Asp Val Leu Val Thr Glu Thr
                405                 410                 415

Cys Ser Leu Met Phe Gly Leu Pro Asp Ile Arg Met Pro Glu Asn Ser
                420                 425                 430

Lys Val Ile Gly Gln His Phe Tyr Leu Ser Ile Gly Met Ala Leu Pro
                435                 440                 445

Cys Ser Phe Gly Val Ser Val Ala Leu Asn Glu Leu Lys Lys Asp Ser
450                 455                 460

Arg Leu Ile Leu Ile Glu Gly Asp Gly Ser Ala Gln Met Thr Val Gln
465                 470                 475                 480

Glu Leu Ser Asn Phe Asn Arg Glu Asn Val Val Lys Pro Leu Ile Ile
                485                 490                 495

Leu Leu Asn Asn Ser Gly Tyr Thr Val Glu Arg Val Ile Lys Gly Pro
                500                 505                 510

Lys Arg Glu Tyr Asn Asp Ile Arg Pro Asp Trp Lys Trp Thr Gln Leu
                515                 520                 525

Leu Gln Thr Phe Gly Met Asp Asp Ala Lys Ser Met Lys Val Thr Thr
                530                 535                 540

Pro Glu Glu Leu Asp Asp Ala Leu Asp Glu Tyr Gly Asn Asn Leu Ser
545                 550                 555                 560

Thr Pro Arg Leu Leu Glu Val Val Leu Asp Lys Leu Asp Val Pro Trp
                565                 570                 575

Arg Phe Asn Lys Met Val Gly Asn
                580
```

<210> SEQ ID NO 11
<211> LENGTH: 407
<212> TYPE: PRT
<213> ORGANISM: Pichia kudriavzevii

<400> SEQUENCE: 11

```
Met Leu Arg Leu Phe Ser Arg Arg Thr Pro Ser Val Arg Ala Leu Pro
1               5                   10                  15

Lys Phe Thr Arg Ser Leu Ala Thr Ala Ser Pro Glu Ala Gly Ala Gln
            20                  25                  30

Glu Val Ser Asn Leu His Asp Ile Val Glu Ile Glu Leu Pro Glu Tyr
        35                  40                  45

Ser Phe Glu Gly Tyr Lys Leu Asp Val Pro Glu Leu Asn Tyr Ser Thr
    50                  55                  60

Glu Lys Gly Thr Leu Leu Gln Met Tyr Lys Asp Met Val Ile Ile Arg
65                  70                  75                  80

Arg Met Glu Met Ala Ala Asp Ala Leu Tyr Lys Ala Lys Lys Ile Arg
                85                  90                  95

Gly Phe Cys His Leu Ser Val Gly Gln Glu Ala Ile Ala Val Gly Ile
            100                 105                 110

Glu Asn Ala Ile Thr Lys Gln Asp Asp Ile Ile Thr Ser Tyr Arg Cys
        115                 120                 125

His Gly Thr Thr Tyr Met Arg Gly Ala Ser Val Gln Glu Val Leu Ala
    130                 135                 140

Glu Leu Met Gly Arg Arg Ser Gly Val Ser Tyr Gly Lys Gly Gly Ser
145                 150                 155                 160

Met His Met Tyr Thr Lys Gly Phe Tyr Gly Gly Asn Gly Ile Val Gly
                165                 170                 175

Ala Gln Val Pro Leu Gly Thr Gly Leu Ala Phe Ala His His Tyr Arg
            180                 185                 190

Asp Gln Lys Asn Met Thr Trp Thr Met Tyr Gly Asp Gly Ala Ala Asn
        195                 200                 205

Gln Gly Gln Val Phe Glu Ser Phe Asn Met Ala Lys Leu Trp Asn Leu
    210                 215                 220

Pro Cys Val Phe Thr Cys Glu Asn Asn Lys Tyr Gly Met Gly Thr Ser
225                 230                 235                 240

Ala Ser Arg Ser Ser Ala Met Thr Glu Tyr Tyr Lys Arg Gly Gln Tyr
                245                 250                 255

Ile Pro Gly Leu Lys Val Asn Gly Met Asp Ile Leu Ala Val Tyr Gln
            260                 265                 270

Ala Ala Lys Phe Ala Lys Glu Trp Thr Ser Asn Asp Asn Gly Pro Leu
        275                 280                 285

Val Ile Glu Phe Glu Thr Tyr Arg Tyr Gly Gly His Ser Met Ser Asp
    290                 295                 300

Pro Gly Thr Thr Tyr Arg Thr Arg Glu Glu Val Gln Asn Met Arg Ser
305                 310                 315                 320

Lys Lys Asp Pro Ile Ala Gly Leu Lys Ala His Leu Leu Glu Phe Asn
                325                 330                 335

Ile Ala Thr Glu Glu Ile Lys Ala Phe Asp Lys Ser Ala Arg Lys
            340                 345                 350

Tyr Val Asp Glu Gln Val Lys Leu Ala Asp Ala Ser Pro Pro Glu
        355                 360                 365

Ala Lys Met Ser Ile Leu Phe Glu Asp Val Tyr Val Pro Gly Ser Glu
        370                 375                 380

Ile Pro Val Leu Arg Gly Arg Ile Arg Asp Asp Ser Trp Ser Phe Glu
385                 390                 395                 400

Lys Gly Gly Phe Ala Tyr Lys
```

<210> SEQ ID NO 12
<211> LENGTH: 388
<212> TYPE: PRT
<213> ORGANISM: Pichia kudriavzevii

<400> SEQUENCE: 12

```
Met Val Ser Pro Ala Glu Arg Leu Ser Thr Ile Ala Ser Thr Ile Lys
1               5                   10                  15

Pro Asn Arg Lys Asp Ser Thr Ser Leu Gln Pro Glu Asp Tyr Pro Glu
            20                  25                  30

His Pro Phe Lys Val Thr Val Val Gly Ser Gly Asn Trp Gly Cys Thr
        35                  40                  45

Ile Ala Lys Val Ile Ala Glu Asn Thr Val Glu Arg Pro Arg Gln Phe
    50                  55                  60

Gln Arg Asp Val Asn Met Trp Val Tyr Glu Glu Leu Ile Glu Gly Glu
65                  70                  75                  80

Lys Leu Thr Glu Ile Ile Asn Thr Lys His Glu Asn Val Lys Tyr Leu
                85                  90                  95

Pro Gly Ile Lys Leu Pro Val Asn Val Ala Val Pro Asp Ile Val
            100                 105                 110

Glu Ala Cys Ala Gly Ser Asp Leu Ile Val Phe Asn Ile Pro His Gln
        115                 120                 125

Phe Leu Pro Arg Ile Leu Ser Gln Leu Lys Gly Lys Val Asn Pro Lys
130                 135                 140

Ala Arg Ala Ile Ser Cys Leu Lys Gly Leu Asp Val Asn Pro Asn Gly
145                 150                 155                 160

Cys Lys Leu Leu Ser Thr Val Ile Thr Glu Glu Leu Gly Ile Tyr Cys
                165                 170                 175

Gly Ala Leu Ser Gly Ala Asn Leu Ala Pro Glu Val Ala Gln Cys Lys
            180                 185                 190

Trp Ser Glu Thr Thr Val Ala Tyr Thr Ile Pro Asp Asp Phe Arg Gly
        195                 200                 205

Lys Gly Lys Asp Ile Asp His Gln Ile Leu Lys Ser Leu Phe His Arg
    210                 215                 220

Pro Tyr Phe His Val Arg Val Ile Ser Asp Val Ala Gly Ile Ser Ile
225                 230                 235                 240

Ala Gly Ala Leu Lys Asn Val Val Ala Met Ala Ala Gly Phe Val Glu
                245                 250                 255

Gly Leu Gly Trp Gly Asp Asn Ala Lys Ala Ala Val Met Arg Ile Gly
            260                 265                 270

Leu Val Glu Thr Ile Gln Phe Ala Lys Thr Phe Phe Asp Gly Cys His
        275                 280                 285

Ala Ala Thr Phe Thr His Glu Ser Ala Gly Val Ala Asp Leu Ile Thr
    290                 295                 300

Thr Cys Ala Gly Gly Arg Asn Val Arg Val Gly Arg Tyr Met Ala Gln
305                 310                 315                 320

His Ser Val Ser Ala Thr Glu Ala Glu Lys Leu Leu Asn Gly Gln
                325                 330                 335

Ser Cys Gln Gly Ile His Thr Thr Arg Glu Val Tyr Glu Phe Leu Ser
            340                 345                 350

Asn Met Gly Arg Thr Asp Glu Phe Pro Leu Phe Thr Thr Tyr Arg
        355                 360                 365
```

```
Ile Ile Tyr Glu Asn Phe Pro Ile Glu Lys Leu Pro Glu Cys Leu Glu
    370                 375                 380

Pro Val Glu Asp
385

<210> SEQ ID NO 13
<211> LENGTH: 388
<212> TYPE: PRT
<213> ORGANISM: Pichia kudriavzevii

<400> SEQUENCE: 13

Met Val Ser Pro Ala Glu Arg Leu Ser Thr Ile Ala Ser Thr Ile Lys
1               5                   10                  15

Pro Asn Arg Lys Asp Ser Thr Ser Leu Gln Pro Glu Asp Tyr Pro Glu
            20                  25                  30

His Pro Phe Lys Val Thr Val Val Gly Ser Gly Asn Trp Gly Cys Thr
        35                  40                  45

Ile Ala Lys Val Ile Ala Glu Asn Thr Val Glu Arg Pro Arg Gln Phe
    50                  55                  60

Gln Arg Asp Val Asn Met Trp Val Tyr Glu Glu Leu Ile Glu Gly Glu
65                  70                  75                  80

Lys Leu Thr Glu Ile Ile Asn Thr Lys His Glu Asn Val Lys Tyr Leu
                85                  90                  95

Pro Gly Ile Lys Leu Pro Val Asn Val Ala Val Pro Asp Ile Val
            100                 105                 110

Glu Ala Cys Ala Gly Ser Asp Leu Ile Val Phe Asn Ile Pro His Gln
        115                 120                 125

Phe Leu Pro Arg Ile Leu Ser Gln Leu Lys Gly Lys Val Asn Pro Lys
    130                 135                 140

Ala Arg Ala Ile Ser Cys Leu Lys Gly Leu Asp Val Asn Pro Asn Gly
145                 150                 155                 160

Cys Lys Leu Leu Ser Thr Val Ile Thr Glu Glu Leu Gly Ile Tyr Cys
                165                 170                 175

Gly Ala Leu Ser Gly Ala Asn Leu Ala Pro Glu Val Ala Gln Cys Lys
            180                 185                 190

Trp Ser Glu Thr Thr Val Ala Tyr Thr Ile Pro Asp Asp Phe Arg Gly
        195                 200                 205

Lys Gly Lys Asp Ile Asp His Gln Ile Leu Lys Ser Leu Phe His Arg
    210                 215                 220

Pro Tyr Phe His Val Arg Val Ile Ser Asp Val Ala Gly Ile Ser Ile
225                 230                 235                 240

Ala Gly Ala Leu Lys Asn Val Val Ala Met Ala Ala Gly Phe Val Glu
                245                 250                 255

Gly Leu Gly Trp Gly Asp Asn Ala Lys Ala Ala Val Met Arg Ile Gly
            260                 265                 270

Leu Val Glu Thr Ile Gln Phe Ala Lys Thr Phe Phe Asp Gly Cys His
        275                 280                 285

Ala Ala Thr Phe Thr His Glu Ser Ala Gly Val Ala Asp Leu Ile Thr
    290                 295                 300

Thr Cys Ala Gly Gly Arg Asn Val Arg Val Gly Arg Tyr Met Ala Gln
305                 310                 315                 320

His Ser Val Ser Ala Thr Glu Ala Glu Lys Leu Leu Asn Gly Gln
                325                 330                 335

Ser Cys Gln Gly Ile His Thr Thr Arg Glu Val Tyr Glu Phe Leu Ser
            340                 345                 350
```

```
Asn Met Gly Arg Thr Asp Glu Phe Pro Leu Phe Thr Thr Thr Tyr Arg
        355                 360                 365

Ile Ile Tyr Glu Asn Phe Pro Ile Glu Lys Leu Pro Glu Cys Leu Glu
        370                 375                 380

Pro Val Glu Asp
385

<210> SEQ ID NO 14
<211> LENGTH: 374
<212> TYPE: PRT
<213> ORGANISM: Pichia kudriavzevii

<400> SEQUENCE: 14

Met Ala Lys Val Asn Tyr Pro Glu Glu Phe Ala Gly Phe Ala Ile Val
1               5                   10                  15

Asp Thr Asn Glu Trp Asn Lys Pro Lys Tyr Ile Thr Tyr Lys Pro Lys
                20                  25                  30

Thr Phe Gly Asp His Asp Ile Asp Ile Glu Ile Glu Cys Cys Gly Leu
            35                  40                  45

Cys Gly Ser Asp Ile Met Thr Ala Arg Gly Gly Glu Ala Gly Trp Gly
        50                  55                  60

Gln Ile Thr Leu Pro Gln Val Val Gly His Glu Ile Ile Gly Lys Val
65                  70                  75                  80

Ile Lys Val Gly Pro Lys Val Thr Leu His Arg Leu Gly Asp Arg Val
                85                  90                  95

Gly Leu Gly Ala Gln Ala Phe Ala Cys Leu Asp Cys Asn Arg Cys Lys
            100                 105                 110

Gln Asp Asn Glu Gln Tyr Cys Pro His Gly Val Thr Thr Tyr Asp Gly
        115                 120                 125

Lys Tyr Pro Asp Gly Tyr Val Ser Gln Gly Gly Tyr Ala Ser His Val
    130                 135                 140

Arg Ala His Glu His Leu Cys Phe Pro Ile Pro Glu Lys Leu Gln Ser
145                 150                 155                 160

Ile His Ala Ala Ser Leu Cys Cys Ala Gly Leu Thr Val Phe Ser Pro
                165                 170                 175

Leu Lys Arg Tyr Ile Pro Lys Asp Leu Pro Asn Gly Val Lys Ala Lys
            180                 185                 190

Val Ala Ile Val Gly Leu Gly Gly Leu Gly His Leu Ala Val Gln Leu
        195                 200                 205

Cys Lys Ala Leu Gly Ala Glu Pro Trp Val Phe Ser Arg Gly Asn Ser
    210                 215                 220

Lys Lys Glu Gln Ala Phe Lys Leu Gly Ala Ser Gly Phe Val Ala Thr
225                 230                 235                 240

Gly Glu Lys Asp Trp Glu Lys Pro Leu Phe Asp Gln Phe Asp Leu Ile
                245                 250                 255

Leu Asn Cys Ala Ile Gly Leu Ser Gly Leu Asn Leu Asp Ala Phe Ile
            260                 265                 270

Ser Ile Leu Lys Val Asp Gly Arg Phe Cys Ser Val Gly Leu Pro Ser
        275                 280                 285

Glu Ser Glu Lys Tyr Asp Val Ser Pro Phe Thr Phe Phe Ser Asn Gly
    290                 295                 300

Ser Cys Leu Cys Ser Ser Ala Leu Gly Ser Arg Glu Glu Ala Leu Glu
305                 310                 315                 320

Leu Phe Glu Leu Ala Ala Glu Asn Asn Ile Val Pro Trp Val Glu Thr
```

```
                325                 330                 335
Ile Pro Ile Ser Glu Lys Gly Cys Glu Glu Ala Leu Thr Arg Ala Trp
            340                 345                 350
Asp Gly Asp Val Arg Tyr Arg Phe Val Phe Thr Glu Phe Asp Lys Ala
            355                 360                 365
Phe Gly Thr Gly Thr Ser
        370

<210> SEQ ID NO 15
<211> LENGTH: 501
<212> TYPE: PRT
<213> ORGANISM: Pichia kudriavzevii

<400> SEQUENCE: 15

Met Ala Leu Pro Leu Ala Thr Thr Ile Ser Leu Ser Ser Gly Lys Thr
1               5                   10                  15
Leu Glu Gln Pro Ile Gly Leu Phe Ile Asp Asn Glu Phe Val Asn Pro
            20                  25                  30
Ile Ser Val Ser Asn Ala Arg Thr Leu Thr Thr Phe Asn Pro Ser Thr
        35                  40                  45
Gly Glu Pro Ile Thr Asp Val His Cys Ala Ser Ala Asp Val Asp
    50                  55                  60
Val Ala Val Asn Ala Ala Asn Lys Ala Met Glu Thr Trp Lys Asp Ile
65                  70                  75                  80
Asp Pro Thr Val Arg Val Glu Leu Leu Leu Lys Leu Ala Ser Leu Val
                85                  90                  95
Asp Glu His Ser Gln Ala Ile Ala Glu Ile Glu Ala Leu Asp Ser Gly
            100                 105                 110
Lys Pro Leu Tyr Ser Asn Ala Leu Ala Asp Val Gln Ser Val Ala Glu
        115                 120                 125
Tyr Leu Arg Tyr Cys Ala Gly Trp Ala Asp Lys Leu His Gly Thr Gln
    130                 135                 140
Ile Pro Ile Asn Ser Lys Val Met Ala Ile Thr Lys Arg Val Pro Leu
145                 150                 155                 160
Val Val Gly Cys Ile Ile Pro Trp Asn Tyr Pro Ile Ser Met Ala Ser
                165                 170                 175
Trp Lys Phe Cys Pro Ala Leu Ala Ala Gly Cys Thr Ile Val Met Lys
            180                 185                 190
Ser Ser Glu Ile Thr Pro Leu Ser Leu Leu Tyr Phe Ala Asn Leu Val
        195                 200                 205
Lys Leu Ala Gly Phe Pro Lys Gly Val Phe Asn Val Ser Gly Phe
    210                 215                 220
Gly Asp Asp Val Gly Ser Ala Leu Ser Asn His Pro Lys Leu Gly Lys
225                 230                 235                 240
Ile Ala Phe Thr Gly Ser Thr Leu Thr Gly Gln Lys Val Met Ala Asp
                245                 250                 255
Ala Ala Arg Ser Asn Leu Lys Ser Val Ser Leu Glu Cys Gly Gly Lys
            260                 265                 270
Ser Pro Leu Ile Val Phe Glu Asp Ala Glu Leu Asp Glu Cys Val Lys
        275                 280                 285
Trp Ala Ser Phe Gly Val Met Tyr Asn Thr Gly Gln Asn Cys Thr Ala
    290                 295                 300
Asn Ser Arg Ile Ile Val His Asp Lys Val Tyr Asp Gln Phe Ile Glu
305                 310                 315                 320
```

Lys Phe Leu Ser Gln Leu Lys Glu Asp Trp Lys Met Gly Asp Val Met
                325                 330                 335

Asn Glu Lys Thr Thr Leu Gly Pro Leu Val Ser Gln Gln Tyr Glu
        340                 345                 350

Arg Val Gln Ser Tyr Ile Asp Ile Gly Val Lys Glu Gly Ala Thr Leu
            355                 360                 365

Ile Gln Pro Leu Lys Glu Ser Thr Pro Ser Asn Gly Phe Tyr Ile Ser
370                 375                 380

Pro Thr Val Phe Thr Asn Val Lys Glu Asp Met Arg Ile Val Lys Glu
385                 390                 395                 400

Glu Ile Phe Gly Pro Val Val Thr Ile Ser Lys Phe Ser Thr Glu Glu
                405                 410                 415

Glu Ala Ile Ser Lys Ala Asn Asp Thr Ile Tyr Gly Leu Ala Ala Met
            420                 425                 430

Leu Phe Thr Thr Asn Phe Glu Arg Ala Asn Arg Val Ala Asp Lys Leu
    435                 440                 445

Glu Ala Gly Ser Val Tyr Ile Asn Ser Ser Asn Glu Ser Thr Lys
        450                 455                 460

Val Pro Phe Gly Gly Met Lys Met Ser Gly Ile Gly Arg Glu Leu Gly
465                 470                 475                 480

Gln Glu Ala Phe Asn Leu Tyr Thr Val Thr Lys Ser Ile Tyr Tyr Ser
                485                 490                 495

Tyr Gly Ala Lys Leu
            500

<210> SEQ ID NO 16
<211> LENGTH: 501
<212> TYPE: PRT
<213> ORGANISM: Pichia kudriavzevii

<400> SEQUENCE: 16

Met Ser Ala Leu Phe Arg Thr Ile Glu Thr Pro Asn Gly Lys Thr Leu
1               5                   10                  15

Glu Gln Pro Leu Gly Leu Phe Ile Asp Asn Glu Trp Val Lys Thr Asn
            20                  25                  30

Arg Thr Phe Glu Thr Ile Asn Pro Ser Thr Gly Glu Ala Ile Cys His
        35                  40                  45

Val Tyr Arg Ala Gly Val Gln Glu Val Asn Asp Ala Val Glu Ala Ala
    50                  55                  60

Asn Arg Ala Phe Arg Asn Glu Ser Trp Ser Gly Leu Thr Gly Ser Gln
65                  70                  75                  80

Arg Gly Asp Leu Leu Tyr Arg Met Tyr Gln Val Ile Lys Arg Asp Ala
                85                  90                  95

Glu Ser Ile Ala Ser Ile Glu Ser Ile Asp Asn Gly Lys Pro Tyr Ala
            100                 105                 110

Ala Glu Cys Leu Asp Gly Asp Leu Gly Glu Ala Ala Asp Val Phe Lys
        115                 120                 125

Tyr Tyr Ala Gly Trp Ala Asp Lys Ile Thr Gly Glu Leu Ile Gly Ser
    130                 135                 140

Ser Val Leu Gly Lys Asn Lys Met Cys Tyr Val Glu Pro Thr Pro Leu
145                 150                 155                 160

Gly Ala Val Gly Gly Ile Val Pro Trp Asn Phe Pro Phe Thr Met Met
                165                 170                 175

Ala Trp Lys Ile Ala Pro Ala Leu Ala Thr Gly Cys Thr Val Val Met
            180                 185                 190

```
Lys Ser Ser Glu Val Thr Pro Leu Thr Ala Leu Trp Tyr Gly Lys Ile
        195                 200                 205

Ala Leu Glu Val Gly Leu Pro Lys Gly Val Leu Asn Ile Leu Ser Gly
    210                 215                 220

Phe Gly Ser Asp Val Gly Ser Ala Met Ala Ser His Pro Lys Leu Ala
225                 230                 235                 240

Lys Ile Ala Phe Thr Gly Ser Thr Ala Thr Gly Lys Lys Ile Met Glu
            245                 250                 255

Ala Ala Gly Gly Ser Asn Leu Lys Lys Val Thr Leu Glu Cys Gly Gly
            260                 265                 270

Lys Ser Pro Tyr Ile Val Phe Asp Asp Ala Asp Leu Glu Leu Ala Val
        275                 280                 285

Glu Trp Ala Tyr Trp Gly Ile Trp Tyr Asn Lys Gly Glu Val Cys Thr
    290                 295                 300

Ser Thr Ser Arg Phe Leu Ile Gln Glu Asp Ile Tyr Asp Lys Phe Val
305                 310                 315                 320

Glu Ser Phe Val Glu Leu Thr Lys Thr Arg Ala Ile Thr Ala Asp Pro
            325                 330                 335

Phe Asp Asp Arg Cys Thr Ile Gly Pro Leu Val Ser Ser Gln Tyr
        340                 345                 350

Glu Lys Val Lys Lys Tyr Val Glu Ile Gly Lys Asn Glu Gly Ala Lys
    355                 360                 365

Leu Leu Thr Gly Lys Phe Ile Asp Gly Pro Gly Tyr Phe Cys Glu Pro
    370                 375                 380

Phe Ile Phe Ser Glu Cys Thr Asp Met Thr Ile Met Lys Glu Glu
385                 390                 395                 400

Ile Phe Gly Pro Val Val Gly Ile Thr Lys Phe Ser Thr Val Lys Glu
            405                 410                 415

Ala Ile Glu Arg Ala Asn Ala Thr Thr Tyr Gly Leu Gly Ala Ala Leu
        420                 425                 430

Phe Ser Ser Asn Ile Thr Lys Ala His Ser Val Ala Ala Lys Leu Glu
    435                 440                 445

Ala Gly Met Val Trp Ile Asn Ser Asn Gly Asp Ser Asp Ile His Ile
    450                 455                 460

Pro Phe Gly Gly Ser Lys Met Ser Gly Ile Gly Arg Glu Leu Gly Pro
465                 470                 475                 480

Tyr Ala Leu Asp Leu Phe Thr Glu Lys Lys Ala Val His Val Asn Leu
            485                 490                 495

Ser Leu Pro Val Lys
        500

<210> SEQ ID NO 17
<211> LENGTH: 502
<212> TYPE: PRT
<213> ORGANISM: Pichia kudriavzevii

<400> SEQUENCE: 17

Met Gly Ala Thr Thr Ala Glu Ile Ser Ile Pro Asn Gly Asn Lys Tyr
1               5                   10                  15

Glu Gln Pro Thr Gly Leu Phe Ile Asn Gly Asp Phe Val Ala Ser Ser
            20                  25                  30

Asp Gly Lys Thr Ala Glu Val Glu Asn Pro Gly Asn Gly Asn Ile Val
        35                  40                  45

Cys Ser Val His Leu Ala Ser Ile Glu Asp Ile Asn Thr Ala Val Glu
```

-continued

```
              50                  55                  60
Ala Ala Glu Asp Ala Phe Phe Lys Arg Trp Ala Thr Ile Ser Gly Lys
 65                  70                  75                  80

Ala Lys Gly Glu Tyr Leu Ser Lys Ile Ala Asp Leu Ile Val Lys Tyr
                 85                  90                  95

Ser Asp Gln Leu Ala Asp Leu Glu Ala Ile Glu Ser Gly Lys Pro Lys
                100                 105                 110

Asp Thr Asn Ala Ile Phe Asp Val Leu His Ser Ala Asp Val Phe Arg
                115                 120                 125

Tyr Tyr Ala Gly Lys Ala Val Thr Ala Gln Ser Gly Lys Thr Ile Glu
                130                 135                 140

Ser Glu Leu Ser Lys Phe Thr Tyr Thr Val Tyr Glu Pro Tyr Gly Val
145                 150                 155                 160

Cys Ala Ala Ile Ile Ala Trp Asn Phe Pro Met Ser Thr Phe Ala Trp
                165                 170                 175

Lys Val Ala Ala Cys Leu Ala Ala Gly Asn Thr Met Val Val Lys Thr
                180                 185                 190

Ser Glu Leu Thr Pro Leu Ser Ala Leu Phe Met Cys Lys Ile Phe Gln
                195                 200                 205

Glu Ala Asp Leu Pro Ala Gly Val Ile Asn Val Thr Cys Gly Leu Gly
                210                 215                 220

Ser Val Ala Gly Val Arg Leu Ser Glu His Glu Lys Val Gln Lys Ile
225                 230                 235                 240

Ser Phe Thr Gly Ser Thr Gly Val Gly Lys Leu Ile Gln Glu Ser Ala
                245                 250                 255

Ala Lys Ser Asn Leu Lys Tyr Cys Thr Leu Glu Cys Gly Gly Lys Ser
                260                 265                 270

Pro Leu Val Ile Tyr Glu Asp Ala Asp Leu Glu Gln Ala Val Lys Trp
                275                 280                 285

Ala Ala Phe Gly Ile Phe Phe Asn Lys Gly Glu Ile Cys Thr Ala Ser
                290                 295                 300

Ser Arg Ile Tyr Val Gln Glu Ser Val Tyr Asp Lys Phe Leu Thr Met
305                 310                 315                 320

Tyr Lys Asp His Val Glu Glu Ala Tyr Val Gln Gly Glu Gln Phe Ala
                325                 330                 335

Thr Gly Val Asn Val Gly Pro Thr Val Cys Lys Ala Gln Gln Glu Lys
                340                 345                 350

Ile Leu Ala Tyr Ile Glu Ser Ala Lys Gln Glu Gly Arg Ile Ile
                355                 360                 365

Thr Gly Gly Lys Ile Pro Ser Tyr Thr Asn Lys Asn Gly Tyr Tyr Leu
                370                 375                 380

Glu Pro Thr Ile Ile Ala Asp Cys Asn Gln Asp Met Lys Val Val Arg
385                 390                 395                 400

Glu Glu Ile Phe Gly Pro Val Val Thr Val Ser Lys Phe Thr Ser Asp
                405                 410                 415

Glu Glu Ala Ile Lys Leu Ser Asn Asp Ser Glu Tyr Gly Leu Ala Ala
                420                 425                 430

Tyr Leu Phe Thr Lys Asp Leu Val Arg Ser Gln Asn Tyr Ile Arg Lys
                435                 440                 445

Val Gln Ser Gly Gln Val Phe Val Asn Phe Thr Phe Ala Ala Asp Phe
                450                 455                 460

Arg Leu Pro Phe Gly Gly Tyr Lys Met Ser Gly Asn Gly Arg Glu Leu
465                 470                 475                 480
```

Gly Asp Glu Gly Leu Ser Ala Phe Gln Gln Val Lys Ala Val His Ile
                485                 490                 495
Asn Leu Thr Gly Lys Leu
            500

<210> SEQ ID NO 18
<211> LENGTH: 497
<212> TYPE: PRT
<213> ORGANISM: Pichia kudriavzevii

<400> SEQUENCE: 18

Met Ser Ala Thr Ser Val Thr Phe Pro Ile Ile Asn Glu Thr Tyr Gln
1               5                   10                  15

Gln Pro Thr Gly Leu Phe Ile Asn Asn Glu Phe Val Ser Ala Lys Ser
            20                  25                  30

Gly Lys Thr Phe Asp Val Asn Thr Pro Ile Asp Glu Ser Leu Ile Cys
        35                  40                  45

Lys Val Gln Gln Ala Asp Ala Glu Asp Val Glu Ile Ala Val Gln Ala
    50                  55                  60

Ala Ser Lys Ala Tyr Lys Thr Trp Arg Phe Thr Pro Pro Asn Glu Arg
65                  70                  75                  80

Gly Arg Tyr Leu Asn Lys Leu Ala Asp Leu Met Asp Glu Lys Arg Asp
                85                  90                  95

Leu Leu Ala Lys Ile Glu Ser Leu Asp Asn Gly Lys Ala Leu His Cys
            100                 105                 110

Ala Lys Phe Asp Val Asn Leu Val Ile Glu Tyr Phe Arg Tyr Cys Ala
        115                 120                 125

Gly Tyr Cys Asp Lys Ile Asp Gly Arg Thr Ile Thr Thr Asp Val Glu
    130                 135                 140

His Phe Thr Tyr Thr Arg Lys Glu Pro Leu Gly Val Cys Gly Ala Ile
145                 150                 155                 160

Thr Pro Trp Asn Phe Pro Leu Leu Met Phe Ala Trp Lys Ile Gly Pro
                165                 170                 175

Ala Leu Ala Thr Gly Asn Thr Ile Ile Leu Lys Pro Ala Ser Ala Thr
            180                 185                 190

Pro Leu Ser Asn Leu Phe Thr Cys Thr Leu Ile Lys Glu Ala Gly Ile
        195                 200                 205

Pro Ala Gly Val Val Asn Val Val Pro Gly Ser Gly Arg Gly Cys Gly
    210                 215                 220

Asn Ser Ile Leu Gln His Pro Lys Ile Lys Lys Val Ala Phe Thr Gly
225                 230                 235                 240

Ser Thr Glu Val Gly Lys Thr Val Met Lys Glu Cys Ala Asn Ser Ile
                245                 250                 255

Lys Lys Val Thr Leu Glu Leu Gly Gly Lys Ser Pro Asn Ile Val Phe
            260                 265                 270

Lys Asp Cys Asn Val Glu Gln Thr Ile Gln Asn Leu Ile Thr Gly Ile
        275                 280                 285

Phe Phe Asn Gly Gly Glu Val Cys Cys Ala Gly Ser Arg Ile Tyr Ile
    290                 295                 300

Glu Ala Thr Asp Glu Lys Trp Tyr Thr Glu Leu Thr Lys Phe Lys
305                 310                 315                 320

Glu Thr Val Glu Lys Leu Lys Ile Gly Asn Pro Phe Glu Glu Gly Val
                325                 330                 335

Phe Gln Gly Ala Gln Thr Thr Pro Asp Gln Phe Gln Thr Val Leu Asp

```
              340                 345                 350
Tyr Ile Thr Ala Ala Asn Glu Ser Ser Leu Lys Leu Leu Thr Gly Gly
                355                 360                 365

Lys Arg Ile Gly Asn Lys Gly Tyr Phe Val Glu Pro Thr Ile Phe Tyr
            370                 375                 380

Asp Val Pro Gln Asn Ser Lys Leu Thr Gln Glu Glu Ile Phe Gly Pro
385                 390                 395                 400

Val Ala Val Val Leu Pro Phe Lys Ser Thr Glu Glu Leu Ile Glu Lys
                405                 410                 415

Ala Asn Asp Ser Asp Phe Gly Leu Gly Ser Gly Ile His Thr Glu Asp
            420                 425                 430

Phe Asn Lys Ala Ile Trp Val Ser Glu Arg Leu Glu Ala Gly Ser Val
            435                 440                 445

Trp Ile Asn Thr Tyr Asn Asp Phe His Pro Ala Pro Phe Gly Gly
            450                 455                 460

Tyr Lys Glu Ser Gly Ile Gly Arg Glu Met Gly Ile Glu Ala Phe Asp
465                 470                 475                 480

Asn Tyr Thr Gln Thr Lys Leu Val Arg Ala Arg Val Asn Lys Pro Ala
                485                 490                 495

Phe

<210> SEQ ID NO 19
<211> LENGTH: 567
<212> TYPE: PRT
<213> ORGANISM: Artificial Sequence
<220> FEATURE:
<223> OTHER INFORMATION: Synthetic Sequence

<400> SEQUENCE: 19

Met Ser Thr Gly Val Lys Ala Asn Asp Val Lys Thr Lys Thr Lys Gly
1               5                   10                  15

Ala Asp Leu Val Val Asp Cys Leu Ile Ala Gln Gly Val Thr His Val
            20                  25                  30

Phe Gly Ile Pro Gly Ala Lys Ile Asp Ala Val Phe Asp Val Leu Gln
        35                  40                  45

Asp Arg Gly Pro Glu Leu Ile Val Cys Arg His Glu Gln Asn Ala Ala
    50                  55                  60

Phe Met Ala Ala Ala Val Gly Arg Leu Thr Gly Lys Pro Gly Val Cys
65                  70                  75                  80

Leu Val Thr Ser Gly Pro Gly Ala Ser Asn Leu Ala Thr Gly Leu Val
                85                  90                  95

Thr Ala Asn Ala Glu Gly Asp Pro Val Val Ala Leu Ala Gly Ala Val
            100                 105                 110

Pro Arg Ala Asp Arg Leu Lys Arg Thr His Gln Ser Met Asp Asn Ala
        115                 120                 125

Ala Leu Phe Glu Pro Ile Thr Lys Tyr Ser Val Glu Val His Pro
    130                 135                 140

Asp Asn Ile Pro Glu Ala Leu Thr Asn Ala Phe Arg Ala Thr Ser
145                 150                 155                 160

Gly Asn Pro Gly Ala Ala Phe Val Ser Leu Pro Gln Asp Val Val Thr
                165                 170                 175

Ala Glu Thr Thr Val Lys Ser Ile Gly Ala Leu Ser Ala Pro Gln Leu
            180                 185                 190

Gly Pro Ala Pro Asp Glu Ala Ile Ser Ala Val Val Ala Lys Ile Lys
        195                 200                 205
```

Ser Ala Lys Leu Pro Val Ile Leu Leu Gly Met Arg Ala Ser Arg Pro
210                 215                 220

Glu Val Thr Lys Ala Val Arg Lys Leu Leu Ala Lys Thr Glu Leu Pro
225                 230                 235                 240

Val Val Glu Thr Tyr Gln Ala Gly Ala Ile Ser Arg Glu Leu Glu
            245                 250                 255

Asp His Phe Phe Gly Arg Val Gly Leu Phe Arg Asn Gln Pro Gly Asp
            260                 265                 270

Ile Leu Leu Glu Gln Ala Asp Leu Val Ile Thr Ile Gly Tyr Asp Pro
            275                 280                 285

Ile Glu Tyr Asp Pro Lys Phe Trp Asn Lys Leu Gly Asp Arg Thr Ile
290                 295                 300

Ile His Leu Asp Asp Ile Gln Ala Asp Ile Asp His Asp Tyr Gln Pro
305                 310                 315                 320

Glu Leu Glu Leu Ile Gly Asp Ile Ala Leu Thr Val Asn Ser Ile Ala
            325                 330                 335

Glu Asp Leu Pro Lys Leu Val Leu Ser Ser Lys Ser Glu Glu Val Leu
            340                 345                 350

Glu Asp Leu Arg Ala Lys Leu Ser Glu Gln Ala Glu Val Pro Ala Arg
            355                 360                 365

Ala Lys Glu Gly Leu Thr His Pro Leu Gln Val Ile Arg Thr Leu Arg
370                 375                 380

Ser Leu Ile Asp Asp Thr Thr Val Thr Cys Asp Ile Gly Ser His
385                 390                 395                 400

Ala Ile Trp Met Ala Arg Tyr Phe Arg Ser Tyr Glu Pro Arg Arg Leu
            405                 410                 415

Leu Phe Ser Asn Gly Met Gln Thr Leu Gly Val Ala Leu Pro Trp Ala
            420                 425                 430

Ile Ala Ala Thr Leu Val Asn Pro Gly Glu Lys Val Val Ser Val Ser
            435                 440                 445

Gly Asp Gly Gly Phe Leu Phe Ser Ala Met Glu Leu Glu Thr Ala Val
            450                 455                 460

Arg Leu Lys Ala Pro Ile Val His Leu Val Trp Asn Asp Gly Thr Tyr
465                 470                 475                 480

Asp Met Val Ala Phe Gln Gln Met Met Lys Tyr Gly Arg Thr Ser Ala
            485                 490                 495

Val Glu Phe Gly Asp Val Asp Ile Val Lys Tyr Ala Glu Ser Phe Gly
            500                 505                 510

Ala Lys Gly Leu Arg Val Asn Ser Pro Asp Glu Leu Glu Asp Val Leu
            515                 520                 525

Lys Ala Ala Leu Asp Ala Glu Gly Pro Val Ile Asp Ile Pro Ile
530                 535                 540

Asp Tyr Arg Asp Asn Ile Lys Leu Ser Glu Lys Leu Leu Pro Asn Gln
545                 550                 555                 560

Phe Asn Glu Met Lys Lys Ala
            565

<210> SEQ ID NO 20
<211> LENGTH: 340
<212> TYPE: PRT
<213> ORGANISM: Artificial Sequence
<220> FEATURE:
<223> OTHER INFORMATION: Synthetic Sequence

<400> SEQUENCE: 20

```
Met Ala Val Lys Val Tyr Tyr Asp Lys Asp Ala Asp Leu Ser Ile Ile
1               5                   10                  15

Gln Gly Lys Lys Val Ala Ile Ile Gly Tyr Gly Ser Gln Gly His Ala
            20                  25                  30

His Ala Leu Asn Leu Arg Asp Ser Gly Val Asp Val Ile Val Gly Leu
        35                  40                  45

Arg Glu Gly Ser Lys Ser Phe Ala Lys Ala Glu Asp Gly Phe Lys
    50                  55                  60

Val Phe Thr Val Ala Glu Ala Ala Lys Gln Ala Asp Val Ile Met Ile
65                  70                  75                  80

Leu Ala Pro Asp Glu Ile Gln Ala Asp Ile Tyr Glu Glu Ile Glu
                85                  90                  95

Pro Asn Leu Lys Ala Gly Asn Ala Leu Phe Phe Ala His Gly Phe Asn
            100                 105                 110

Ile His Phe Gly Gln Ile Lys Pro Pro Ala Asp Val Asp Val Phe Met
        115                 120                 125

Val Ala Pro Lys Gly Pro Gly His Leu Val Arg Arg Thr Phe Val Glu
130                 135                 140

Gly Gly Gly Val Pro Cys Leu Ile Ala Val Tyr Gln Asp Ala Ser Gly
145                 150                 155                 160

Asn Ala Lys Asp Leu Ala Leu Ser Tyr Ala Lys Gly Ile Gly Gly Ala
            165                 170                 175

Arg Ala Gly Val Ile Glu Thr Thr Phe Lys Glu Glu Thr Glu Thr Asp
            180                 185                 190

Leu Phe Gly Glu Gln Ala Val Leu Cys Gly Gly Leu Thr Ala Leu Val
        195                 200                 205

Lys Ala Gly Phe Glu Thr Leu Val Glu Ala Gly Tyr Ala Pro Glu Met
210                 215                 220

Ala Tyr Phe Glu Cys Leu His Glu Leu Lys Leu Ile Val Asp Leu Met
225                 230                 235                 240

Tyr Glu Gly Gly Ile Ala Asn Met Arg Tyr Ser Ile Ser Asp Thr Ala
            245                 250                 255

Glu Tyr Gly Asp Tyr Val Ser Gly Pro Arg Val Ile Thr Ala Glu Thr
        260                 265                 270

Lys Glu Ala Met Lys Ala Val Leu Ala Asp Ile Gln Asp Gly Thr Phe
            275                 280                 285

Ala Lys Arg Phe Ile Ala Glu Asn Lys Ala Gly Arg Pro Glu Phe Asn
        290                 295                 300

Ala Leu Arg Ala Lys Glu Ala Glu His Pro Ile Glu Lys Val Gly Ala
305                 310                 315                 320

Lys Leu Arg Asp Met Met Pro Trp Val Lys Asn Lys Asp Val Asp
        325                 330                 335

Ala Lys Lys Asn
            340

<210> SEQ ID NO 21
<211> LENGTH: 340
<212> TYPE: PRT
<213> ORGANISM: Lactococcus lactis

<400> SEQUENCE: 21

Met Ala Val Thr Met Tyr Tyr Glu Asp Asp Val Glu Val Ser Ala Leu
1               5                   10                  15

Ala Gly Lys Gln Ile Ala Val Ile Gly Tyr Gly Ser Gln Gly His Ala
```

```
                20                  25                  30

His Ala Gln Asn Leu Arg Asp Ser Gly His Asn Val Ile Ile Gly Val
                35                  40                  45

Arg His Gly Lys Ser Phe Asp Lys Ala Lys Glu Asp Gly Phe Glu Thr
            50                  55                  60

Phe Glu Val Gly Glu Ala Val Ala Lys Ala Asp Val Ile Met Val Leu
 65                  70                  75                  80

Ala Pro Asp Glu Leu Gln Gln Ser Ile Tyr Glu Glu Asp Ile Lys Pro
                85                  90                  95

Asn Leu Lys Ala Gly Ser Ala Leu Gly Phe Ala His Gly Phe Asn Ile
            100                 105                 110

His Phe Gly Tyr Ile Lys Val Pro Glu Asp Val Asp Val Phe Met Val
            115                 120                 125

Ala Pro Lys Ala Pro Gly His Leu Val Arg Arg Thr Tyr Thr Glu Gly
            130                 135                 140

Phe Gly Thr Pro Ala Leu Phe Val Ser His Gln Asn Ala Ser Gly His
145                 150                 155                 160

Ala Arg Glu Ile Ala Met Asp Trp Ala Lys Gly Ile Gly Cys Ala Arg
                165                 170                 175

Val Gly Ile Ile Glu Thr Thr Phe Lys Glu Thr Glu Glu Asp Leu
                180                 185                 190

Phe Gly Glu Gln Ala Val Leu Cys Gly Gly Leu Thr Ala Leu Val Glu
            195                 200                 205

Ala Gly Phe Glu Thr Leu Thr Glu Ala Gly Tyr Ala Gly Glu Leu Ala
            210                 215                 220

Tyr Phe Glu Val Leu His Glu Met Lys Leu Ile Val Asp Leu Met Tyr
225                 230                 235                 240

Glu Gly Gly Phe Thr Lys Met Arg Gln Ser Ile Ser Asn Thr Ala Glu
                245                 250                 255

Phe Gly Asp Tyr Val Thr Gly Pro Arg Ile Ile Thr Asp Ala Val Lys
            260                 265                 270

Lys Asn Met Lys Leu Val Leu Ala Asp Ile Gln Ser Gly Lys Phe Ala
            275                 280                 285

Gln Asp Phe Val Asp Asp Phe Lys Ala Gly Arg Pro Lys Leu Thr Ala
            290                 295                 300

Tyr Arg Glu Ala Ala Lys Asn Leu Glu Ile Glu Lys Ile Gly Ala Glu
305                 310                 315                 320

Leu Arg Lys Ala Met Pro Phe Thr Gln Ser Gly Asp Asp Ala Phe
                325                 330                 335

Lys Ile Tyr Gln
            340

<210> SEQ ID NO 22
<211> LENGTH: 606
<212> TYPE: PRT
<213> ORGANISM: Artificial Sequence
<220> FEATURE:
<223> OTHER INFORMATION: Synthetic Sequence

<400> SEQUENCE: 22

Met Pro Lys Tyr Arg Ser Arg Thr Ile Thr His Gly Arg Asn Met Ala
 1               5                  10                  15

Gly Ala Arg Ala Leu Trp Arg Ala Thr Gly Met Lys Asp Glu Asp Phe
                20                  25                  30

Gly Lys Pro Ile Ile Ala Val Ala Asn Ser Phe Thr Gln Phe Val Pro
```

```
                35                  40                  45
Gly His Val His Leu Lys Asp Leu Gly Gln Leu Val Lys Glu Glu Ile
 50                  55                  60

Glu Ala Ala Gly Gly Val Pro Lys Glu Phe Asn Thr Ile Ala Val Asp
 65                  70                  75                  80

Asp Gly Ile Ala Met Gly His Asp Gly Met Leu Tyr Ser Leu Pro Ser
                 85                  90                  95

Arg Glu Ile Ile Ala Asp Ser Val Glu Tyr Met Val Asn Ala His Cys
                100                 105                 110

Ala Asp Ala Met Val Cys Ile Ser Asn Cys Asp Lys Ile Thr Pro Gly
            115                 120                 125

Met Leu Met Ala Ala Arg Leu Asn Ile Pro Ala Val Phe Val Ser
    130                 135                 140

Gly Gly Pro Met Glu Ala Gly Lys Thr Lys Leu Ser Asp Gly Leu Thr
145                 150                 155                 160

Lys Leu Asp Leu Phe Glu Ala Met Gly Ala Ala Asp Gly Lys Ile
                165                 170                 175

Ser Asp Glu Asp Val Ala Gln Ile Glu Arg Ser Ala Cys Pro Thr Cys
            180                 185                 190

Gly Ser Cys Ser Gly Met Phe Thr Ala Asn Ser Met Asn Cys Leu Thr
        195                 200                 205

Glu Ala Leu Gly Leu Ser Leu Pro Gly Asn Gly Ser Ile Leu Ala Thr
    210                 215                 220

His Ala Asp Arg Lys Glu Leu Phe Arg Glu Ala Gly Arg Ala Ile Val
225                 230                 235                 240

Glu Leu Ala Lys Arg Tyr Tyr Glu Gln Asp Asp Lys Ser Ile Leu Pro
                245                 250                 255

Arg Asp Ile Ala Thr Lys Glu Ala Phe Glu Asn Ala Met Ala Leu Asp
            260                 265                 270

Met Ala Met Gly Gly Ser Thr Asn Thr Val Leu His Leu Leu Ala Ile
        275                 280                 285

Ala Gln Glu Ala Glu Val Asp Phe Thr Leu Asp Ile Asp Arg Ile
    290                 295                 300

Ser Arg Arg Val Pro His Leu Cys Lys Val Ala Pro Ser Gly Gln Lys
305                 310                 315                 320

Tyr His Met Glu Asp Val His Arg Ala Gly Gly Ile Pro Ala Ile Leu
                325                 330                 335

Gly Glu Leu Leu Arg Ala Gly Leu Leu His Gly Asp Cys Leu Thr Val
            340                 345                 350

Thr Gly Lys Thr Leu Ala Glu Asn Leu Ala Asp Trp Asp Ile Pro Pro
        355                 360                 365

Thr Gln Asp Glu Ala Val Gln Glu Phe Phe Arg Ala Pro Gly Gly
    370                 375                 380

Ile Arg Thr Gln Lys Ala Phe Ser Gln Ser Cys Arg Trp Asp Thr Leu
385                 390                 395                 400

Asp Leu Asp Arg Asp Glu Gly Val Ile Arg Pro Leu Glu Asn Ala Phe
                405                 410                 415

Ser Lys Asp Gly Gly Leu Ala Val Leu Lys Gly Asn Leu Ala Pro Asp
            420                 425                 430

Gly Cys Val Val Lys Thr Ala Gly Val Asp Glu Ser Ile Leu Lys Phe
        435                 440                 445

Thr Gly Pro Ala Arg Val Phe Glu Ser Gln Asp Glu Ala Val Glu Ala
    450                 455                 460
```

```
Ile Leu Asn Gly Lys Val Lys Ala Gly Asp Val Val Ile Arg Tyr
465                 470                 475                 480

Glu Gly Pro Lys Gly Pro Gly Met Gln Glu Met Leu Tyr Pro Thr
            485                 490                 495

Ser Tyr Leu Lys Gly Lys Gly Leu Gly Lys Asp Cys Ala Leu Ile Thr
        500                 505                 510

Asp Gly Arg Phe Ser Gly Gly Thr Ser Gly Leu Ser Ile Gly His Val
            515                 520                 525

Ser Pro Glu Ala Ala Glu Gly Pro Ile Ala Leu Val Glu Asp Gly
            530                 535                 540

Asp Arg Ile Thr Ile Asp Ile Pro Asn Arg Ser Ile Asp Leu Leu Val
545                 550                 555                 560

Ser Asp Glu Glu Leu Ala Ala Arg Arg Ala Ala Trp Lys Pro Pro
                565                 570                 575

Arg Pro Arg Tyr Val Ser Gly Ala Leu Lys Ala Tyr Ala Lys Leu Val
            580                 585                 590

Thr Ser Ala Asp Lys Gly Ala Val Arg Asp Leu Ser Lys Leu
            595                 600                 605

<210> SEQ ID NO 23
<211> LENGTH: 547
<212> TYPE: PRT
<213> ORGANISM: Artificial Sequence
<220> FEATURE:
<223> OTHER INFORMATION: Synthetic Sequence

<400> SEQUENCE: 23

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Lys Asp Met Lys Trp Ile Gly Asn Ala Asn
        35                  40                  45

Glu Leu Asn Ala Ser Tyr Met Ala Asp Gly Tyr Ala Arg Thr Lys Lys
50                  55                  60

Ala Ala Ala Phe Leu Thr Thr Phe Gly Val Gly Glu Leu Ser Ala Ile
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Asp Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Glu Gln
            180                 185                 190

Glu Ile Leu Asn Lys Ile Glu Glu Ser Leu Lys Asn Ala Lys Lys Pro
        195                 200                 205

Val Val Ile Ala Gly His Glu Ile Ile Ser Phe Gly Leu Glu Lys Thr
    210                 215                 220
```

```
Val Thr Gln Phe Ile Ser Lys Thr Lys Leu Pro Ile Thr Thr Leu Asn
225                 230                 235                 240

Phe Gly Lys Ser Ala Val Asp Glu Glu Leu Pro Ser Phe Leu Gly Ile
            245                 250                 255

Tyr Asn Gly Lys Leu Ser Glu Glu Ser Leu Lys Glu Phe Val Glu Ser
            260                 265                 270

Ala Asp Phe Ile Leu Met Leu Gly Val Lys Leu Thr Asp Ser Ser Thr
            275                 280                 285

Gly Ala Phe Thr His His Leu Asn Glu Asn Lys Met Ile Ser Leu Asn
            290                 295                 300

Ile Asp Glu Gly Lys Ile Phe Asn Glu Val Ile Glu Asn Phe Asp Phe
305                 310                 315                 320

Glu Ser Leu Val Ser Ser Leu Ser Asp Leu Ser Gly Ile Glu Tyr Glu
                325                 330                 335

Gly Lys Tyr Ile Asp Lys Lys Gln Glu Asp Phe Ile Pro Ser Asp Ala
            340                 345                 350

Leu Leu Ser Gln Asp Arg Leu Trp Gln Ala Val Glu Asn Leu Thr Gln
            355                 360                 365

Ser Asn Glu Thr Ile Val Ala Glu Gln Gly Thr Ser Phe Phe Gly Ala
            370                 375                 380

Ser Asn Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Leu Asn
            435                 440                 445

Pro Ile Cys Phe Ile Ile Asn Asn Asp Gly Tyr Thr Val Glu Arg Glu
450                 455                 460

Ile His Gly Pro Asn Gln Ser Tyr Asn Asp Ile Pro Met Trp Asn Tyr
465                 470                 475                 480

Ser Lys Leu Pro Glu Val Phe Gly Ala Thr Glu Asp Arg Val Val Ser
            485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Val Leu Ala Lys
            515                 520                 525

Glu Asp Ala Pro Lys Leu Leu Lys Lys Met Gly Lys Leu Phe Ala Glu
            530                 535                 540

Gln Asn Lys
545

<210> SEQ ID NO 24
<211> LENGTH: 499
<212> TYPE: PRT
<213> ORGANISM: Artificial Sequence
<220> FEATURE:
<223> OTHER INFORMATION: Synthetic Sequence

<400> SEQUENCE: 24

Met Ser Glu Ser Gln Val Ala Val Leu Pro Asn Val Gln Gln Phe Leu
1               5                   10                  15

Asp Arg Gln His Gly Leu Tyr Ile Asp Gly Arg Gln Val Ala Ser Gln
            20                  25                  30
```

-continued

```
Ser Glu Lys Arg Leu Pro Val Phe Asn Pro Ala Thr Gly Gln Ala Ile
         35                  40                  45

Ala Ser Thr Ala Asp Ala Ser Glu Ala Asp Val Asp Arg Ala Val Met
     50                  55                  60

Ser Ala Trp Arg Ala Phe Val Asp Arg Arg Trp Ala Gly Arg Leu Pro
 65                  70                  75                  80

Ala Glu Arg Glu Arg Ile Leu Leu Arg Phe Ala Asp Leu Val Glu Gln
                 85                  90                  95

His Ala Glu Glu Leu Ala Gln Leu Gly Thr Leu Glu Gln Gly Lys Ser
                100                 105                 110

Ile Ala Ile Ser Arg Ala Phe Glu Val Gly Cys Thr Leu Asn Trp Met
            115                 120                 125

Arg Tyr Thr Ala Gly Leu Thr Thr Lys Ile Ala Gly Lys Thr Leu Asp
        130                 135                 140

Leu Ser Ile Pro Leu Pro Pro Gly Ala Arg Tyr Gln Ala Trp Thr Arg
145                 150                 155                 160

Lys Glu Pro Val Gly Val Val Ala Gly Ile Val Pro Trp Asn Phe Pro
                165                 170                 175

Leu Met Ile Gly Met Trp Lys Val Met Pro Ala Leu Ala Ala Gly Cys
                180                 185                 190

Ser Ile Val Ile Lys Pro Ser Glu Thr Thr Pro Leu Thr Leu Leu Arg
            195                 200                 205

Val Ala Glu Leu Ala Ser Glu Ala Gly Ile Pro Asp Gly Val Phe Asn
        210                 215                 220

Val Val Thr Gly Ser Gly Ala Val Cys Gly Ala Ala Leu Thr Ser His
225                 230                 235                 240

Pro His Val Ala Lys Val Ser Phe Thr Gly Ser Thr Ala Thr Gly Lys
                245                 250                 255

Gln Ile Ala Arg Thr Ala Ala Asp Arg Leu Thr Arg Val Thr Leu Glu
            260                 265                 270

Leu Gly Gly Lys Asn Pro Ala Ile Val Leu Lys Asp Ala Asp Pro Gln
        275                 280                 285

Trp Val Ile Glu Gly Leu Met Met Gly Ser Phe Leu Asn Gln Gly Gln
        290                 295                 300

Val Cys Ala Ala Ser Ser Arg Ile Tyr Ile Glu Ala Pro Leu Phe Asp
305                 310                 315                 320

Thr Leu Val Ala Gly Phe Glu Gln Ala Val Lys Ser Leu Ser Val Gly
                325                 330                 335

Pro Gly Met Ser Pro Thr Ala Gln Ile Asn Pro Leu Val Ser Arg Ala
            340                 345                 350

His Cys Asp Lys Val Ala Ala Phe Leu Asp Asp Ala Gln Ala Gln Gly
        355                 360                 365

Ala Glu Leu Ile Arg Gly Ala Ala Gly Pro Ala Gly Gln Gly Tyr Tyr
        370                 375                 380

Val Ser Pro Thr Leu Val Val Asn Pro Asp Ala Gly Leu Arg Leu Thr
385                 390                 395                 400

Arg Glu Glu Val Phe Gly Pro Val Val Asn Leu Val Arg Val Ala Asp
                405                 410                 415

Gly Glu Glu Ala Leu Arg Leu Ala Asn Asp Thr Asp Tyr Gly Leu Thr
            420                 425                 430

Ala Ser Val Trp Thr Gln Asp Leu Ser Gln Ala Leu Glu Tyr Thr Asp
        435                 440                 445
```

```
Arg Leu Gln Ala Gly Thr Val Trp Val Asn Ser His Thr Leu Ile Asp
    450                 455                 460
Ala Asn Leu Pro Phe Gly Gly Met Lys Gln Ser Gly Thr Gly Arg Asp
465                 470                 475                 480
Phe Gly Pro Asp Trp Leu Asp Gly Trp Cys Glu Thr Lys Ser Val Cys
                485                 490                 495
Val Arg Tyr
```

RECOMBINANT HOST CELLS AND METHODS FOR THE PRODUCTION OF ISOBUTYRIC ACID

CROSS-REFERENCE TO RELATED APPLICATIONS

This application claims the benefit of priority under 35 U.S.C. 119(e) and Article 2 of the Paris Convention for the Protection of Industrial Property (1883) to U.S. provisional application Ser. No. 62/615,202 filed 9 Jan. 2018, the entire contents of which are incorporated herein by this reference.

REFERENCE TO SEQUENCE LISTING

This application contains a Sequence Listing submitted via EFS-web and is hereby incorporated by reference in its entirety. The ASCII copy, created on Jan. 4, 2019, is named LYGOS_0011_01_WO_ST25 and is 101 KB in size.

FIELD

Embodiments herein relate to recombinant host cells and methods for producing isobutyric acid in recombinant host cells. In certain embodiments, the methods include using recombinant host cells and methods to produce isobutyric acid by microbial fermentation using a carbon source, such as a sugar feedstock. In some embodiments, the recombinant host cells include archaeal, prokaryotic, or eukaryotic cells. In some embodiments, the recombinant host cells contain heterologous nucleic acids encoding one or more isobutyric acid pathway enzyme, wherein the pathway enzymes may include acetolactate synthase, ketol-acid reductoisomerase, dihydroxy-acid dehydratase, branched-chain-2-oxoacid decarboxylase and isobutyraldehyde dehydrogenase.

BACKGROUND

The long-term economic and environmental concerns associated with the petrochemical industry have provided the impetus for increased research, development, and commercialization of processes for conversion of carbon feedstocks into chemicals that can replace those petroleum feedstocks. One approach is the development of biorefining processes to convert renewable feedstocks into products that can replace petroleum-derived chemicals. Two common goals in improving a biorefining process include achieving a lower cost of production and reducing detrimental effects on the environment.

Isobutyric acid (CAS No. 79-31-2) is an important intermediate chemical that can be dehydrogenated to produce the industrially important compound methacrylic acid (see Ullmann's Encyclopedia of Industrial Chemistry), a key component in the manufacture of polymer dispersions (coatings, paints and printing inks), adhesives, binding agents, super absorbent polymers, flocculants, detergents, varnishes, fibers and plastics, as well as chemical intermediates. Esters of isobutyric acid (for example, methyl butyrate and ethyl butyrate) are also important solvents, coalescents, extractants, flavor and fragrance compounds, and diluents used in paints, lacquers, and coatings.

Isobutyric acid can be produced by several routes of chemical synthesis, each requiring a petrochemical feedstock. Isobutyric acid may be prepared by: 1) carbonylation of propene with a strong acid catalyst; 2) hydrolysis of isobutyronitrile with alkalis; 3) oxidation of isobutanol with potassium dichromate and sulfuric acid; or 4) reacting sodium amalgam with methacrylic acid.

The present disclosure provides recombinant host cells and methods to produce isobutyric acid by microbial fermentation using a carbon source, such as a sugar feedstock. The methods described herein not only comprise a renewable and cheaper starting material compared to petrochemicals, but also contribute to energy independence. The methods described herein enable higher fermentation yields and productivities in the production of isobutyric acid.

SUMMARY

In a first aspect, one embodiment of this disclosure provides recombinant host cells capable of producing isobutyric acid containing one or more heterologous nucleic acids that encode the isobutyric acid biosynthetic pathway, wherein the pathway enzymes include acetolactate synthase, ketol-acid reductoisomerase, dihydroxy-acid dehydratase, branched-chain-2-oxoacid decarboxylase and isobutyraldehyde dehydrogenase.

In some embodiments, the recombinant host cell is a yeast cell. In certain embodiments, the yeast cell belongs to the *Issatchenkia orientalis/Pichia fermentans* clade. In some embodiments, the yeast cell belongs to the genus *Pichia*, *Issatchenkia* or *Candida*. In some embodiments, the yeast cell is *Pichia kudriavzevii*. In some embodiments, the yeast cell belongs to the *Saccharomyces* clade. In some embodiments, the yeast cell is *Saccharomyces cerevisiae*.

In other embodiments, the recombinant host cell is a prokaryotic cell. In some embodiments, the prokaryotic cell belongs to the genus *Escherichia*, *Corynebacterium*, *Bacillus*, or *Lactococcus*. In some embodiments, the prokaryotic cell is *Escherichia coli*, *Corynebacterium glutamicum*, *Bacillus subtilis*, or *Lactococcus lactis*.

In some embodiments, the recombinant host cells contain heterologous nucleic acids encoding an acetolactate synthase with substantial amino acid sequence homology to SEQ ID NO: 1 or SEQ ID NO: 19. In some embodiments, the recombinant host cells contain heterologous nucleic acids encoding a ketol-acid reductoisomerase with substantial homology to the amino acid sequence represented by SEQ ID NO: 2 or SEQ ID NO: 21. In some embodiments, the recombinant host cells contain heterologous nucleic acids encoding a dihydroxy-acid dehydratase with substantial homology to the amino acid sequence represented by SEQ ID NO: 3 or SEQ ID NO: 22. In some embodiments, the recombinant host cells contain heterologous nucleic acids encoding a branched-chain-2-oxoacid decarboxylase with substantial homology to the amino acid sequence represented by SEQ ID NO: 4 or SEQ ID NO: 23. In some embodiments, the recombinant host cells contain heterologous nucleic acids encoding a isobutyraldehyde dehydrogenase with substantial homology to the amino acid sequence represented by SEQ ID NO: 5 or SEQ ID NO: 24.

In another aspect, some embodiments of this disclosure provide recombinant host cells that further contain one or more heterologous nucleic acids encoding one or more ancillary proteins that function in redox cofactor recycling, redox cofactor biogenesis, or organic acid transport. In some embodiments, the one or more ancillary proteins include mitochondrial external NADH dehydrogenase, water-forming NADH oxidase, isobutyric acid transporter, or combination thereof. Both the mitochondrial external NADH dehydrogenase and water-forming NADH oxidase oxidize NADH to NAD+, recycling the cofactor necessary for efficient isobutyric acid pathway activity. In one embodiment, the ancillary protein is an external NADH dehydrogenase, NdeI, derived from *P. kudriavzevii*. In some embodiments, the ancillary protein has at least 60%, at least 70%, at least 80%, at least 90%, or at least 95% amino acid identity to the amino acid sequence represented by SEQ ID NO: 6. In one embodiment, the ancillary protein is a water forming NADH oxidase derived from *Lactococcus lactis* (NoxE; UniProt ID: A2RIB7; SEQ ID NO: 7). In some embodiments, the ancillary protein has at least 60%, at least 70%, at least 80%, at least 90%, or at least 95% amino acid identity to the amino acid sequence represented by SEQ ID NO: 7. In one embodiment, the ancillary protein has isobutyric acid transporter activity. Examples of isobutyric acid transporters include *Saccharomyces cerevisiae* PDR12, *Saccharomyces cerevisiae* WAR1, and *Kluyveromyces marxianus* PDC12 and in some embodiments the ancillary protein has at least 60%, at least 70%, at least 80%, at least 90%, or at least 95% amino acid identity to *S. cerevisiae* PDR12, *S. cerevisiae* WAR1, and/or *K. marxianus* PDC12.

In another aspect, some embodiments of this disclosure provide recombinant host cells that further include a genetic disruption of one or more genes wherein the one or more genes encodes pyruvate decarboxylase, pyruvate dehydrogenase, alcohol dehydrogenase, acetaldehyde dehydrogenase, or glycerol-3-phosphate dehydrogenase, or combination thereof. In some embodiments, the one or more genes encodes an amino acid sequence that has at least 60%, at least 70%, at least 80%, at least 90%, or at least 95% homology to SEQ ID NO: 12, encoding *P. kudriavzevii* NAD-dependent glycerol-3-phosphate dehydrogenase (PkGPD1). Glycerol-3-phosphate dehydrogenase catalyzes the conversion of dihydroxyacetone phosphate to glycerol 3-phosphate and its activity can lead to production of the byproduct glycerol. As such, deletion or disruption of the nucleic acid(s) encoding glycerol-3-phosphate dehydrogenase decreases glycerol production as compared to a control, parental host cell that does not comprise said deletion or disruption. In some embodiments, the recombinant host cell comprising deletion or disruption of one or more nucleic acids encoding one or more glycerol-3-phosphate dehydrogenase enzymes produces less than 2.5 g/l glycerol. In some embodiments, the one or more genes encodes a pyruvate decarboxylase with amino acid sequence represented by SEQ ID NO: 8, SEQ ID NO: 9, SEQ ID NO: 10, or a combination thereof. Pyruvate decarboxylase catalyzes the conversion of pyruvate to acetaldehyde and its activity can lead to production of the byproduct ethanol. As such, deletion or disruption of the nucleic acid(s) encoding one or more pyruvate decarboxylase enzymes decreases ethanol production as compared to a control, parental host cell that does not comprise said deletion or disruption. In some embodiments, the recombinant host cell comprising deletion or disruption of one or more nucleic acids encoding one or more pyruvate decarboxylase enzymes produces less than 2.5 g/l ethanol. In some embodiments, the one or more genes encodes an alcohol dehydrogenase with amino acid sequence represented by SEQ ID NO: 13, SEQ ID NO: 14, or a combination thereof. Alcohol dehydrogenase catalyzes the conversion of aldehydes to alcohols, and as such can convert isobutyraldehyde to isobutanol, an undesirable byproduct. Deletion or disruption of the nucleic acid(s) encoding one or more alcohol dehydrogenase enzymes decreases ethanol production as compared to a control, parental host cell that does not comprise said deletion or disruption. In some embodiments, the recombinant host cell comprising deletion or disruption of one or more nucleic acids encoding one or more alcohol dehydrogenase enzymes produces less than 5 g/l isobutanol. In some embodiments, the one or more genes encodes an acetaldehyde dehydrogenase with amino acid sequence represented by SEQ ID NO: 15, SEQ ID NO: 16, SEQ ID NO: 17, SEQ ID NO: 18, or a combination thereof. Acetaldehyde dehydrogenase catalyzes the conversion of acetaldehyde to acetate, an undesirable byproduct. Deletion or disruption of the nucleic acid(s) encoding one or more acetaldehyde dehydrogenase enzymes decreases acetate production as compared to a control, parental host cell that does not comprise said deletion or disruption. In some embodiments, the recombinant host cell comprising deletion or disruption of one or more nucleic acids encoding one or more acetaldehyde dehydrogenase enzymes produces less than 5 g/l acetate.

In another aspect, some embodiments of this disclosure provide a method for the production of isobutyric acid that includes culturing the recombinant host cells detailed in this disclosure for a sufficient period of time to produce isobutyric acid. In some embodiments, the method further includes an oxygen transfer rate greater than 10 mmol/l/hr. In some embodiments, the method further includes an operational temperature of between about 25° C. and about 45° C. In some embodiments, the method further includes a final fermentation broth pH of about pH 5. In some embodiments, the method produces a solution containing at least 50 g/l isobutyric acid. In some embodiments, the method further includes providing at least 100 g-glucose to the recombinant host cell and producing an isobutyric acid yield of at least 25%.

BRIEF DESCRIPTION OF THE DRAWINGS

The following drawing forms part of the instant specification and is included to further demonstrate certain aspects of particular embodiments herein. Those skilled in the art will understand that the drawing described herein is for illustration purposes only. The drawing is not intended to limit the scope of the present disclosure.

FIG. 1. represents an example of an isobutyric acid pathway, which may be used to convert two molecules of pyruvate into one molecule isobutyric acid.

DETAILED DESCRIPTION

The present disclosure provides recombinant host cells and materials and methods for the biological production and purification of isobutyric acid using recombinant host cells.

While the present disclosure describes aspects and specific embodiments, those skilled in the art will recognize that various changes may be made and equivalents may be substituted without departing from embodiments of the present disclosure. The present disclosure is not limited to particular nucleic acids, expression vectors, enzymes, biosynthetic pathways, host microorganisms, or processes, as such may vary. The terminology used herein is for the purposes of describing particular aspects and embodiments only and is not to be construed as limiting. In addition, many modifications may be made to adapt a particular situation, material, composition of matter, process, process steps or process flows, in accordance with embodiments of the present disclosure. All such modifications are within the scope of the claims appended hereto.

Definitions

Unless defined otherwise, all technical and scientific terms used herein have the same meaning as is commonly understood by one of ordinary skill in the art to which this disclosure pertains.

The term "accession number" and similar terms such as "protein accession number", "UniProt ID", "gene ID" and "gene accession number" refer to designations given to specific proteins or genes. These identifiers described a gene or protein sequence in publicly accessible databases such as the National Center for Biotechnology Information (NCBI).

A plus (+) in a consensus sequence indicates any amino acid may be present at the specified position. Thus, a plus in a consensus sequence herein indicates a position at which the amino acid is generally non-conserved; a homologous protein sequence, when aligned with the consensus sequence, can have any amino acid at the indicated "+" position.

As used herein, when one of multiple closely related amino acids is found at the aligned position of an amino acid sequence, the following one-letter symbol is used—"B" refers to aspartic acid or asparagine; "Z" refers to glutamine or glutamic acid; "J" refers to leucine or isoleucine; and "X" or "+" refers to any amino acid. Generally, homologous proteins share substantial sequence identity. Sets of homologous proteins generally possess one or more specific amino acids that are conserved across all members of the consensus sequence protein class. The percent sequence identity of a protein relative to a consensus sequence is determined by aligning the protein sequence against the consensus sequence. Practitioners in the art will recognized that various sequence alignment algorithms are suitable for aligning a protein with a consensus sequence. See, for example, Needleman, S B, et al., "A general method applicable to the search for similarities in the amino acid sequence of two proteins." Journal of Molecular Biology 48 (3): 443-53 (1970). Following alignment of the protein sequence relative to the consensus sequence, the percentage of positions where the protein possesses an amino acid described by the same position in the consensus sequence determines the percent sequence identity. When a degenerate amino acid is present (i.e., B, Z, X, J or "+") in a consensus sequence, any of the amino acids described by the degenerate amino acid may be present in the protein at the aligned position for the protein to be identical to the consensus sequence at the aligned position.

As used herein, the term "express", when used in connection with a nucleic acid encoding an enzyme or an enzyme itself in a cell, means that the enzyme, which may be an endogenous or exogenous (heterologous) enzyme, is produced in the cell. The term "overexpress", in these contexts, means that the enzyme is produced at a higher level, i.e., enzyme levels are increased, as compared to the wild-type, in the case of an endogenous enzyme. Those skilled in the art appreciate that overexpression of an enzyme can be achieved by increasing the strength or changing the type of the promoter used to drive expression of a coding sequence, increasing the strength of the ribosome binding site or Kozak sequence, increasing the stability of the mRNA transcript, altering the codon usage, increasing the stability of the enzyme, and the like.

The terms "expression vector" or "vector" refer to a nucleic acid and/or a composition containing a nucleic acid that can be introduced into a host cell, e.g., by transduction, transformation, or infection, such that the cell then produces (i.e., expresses) nucleic acids and/or proteins other than those native to the cell, or in a manner not native to the cell, that are contained in or encoded by the nucleic acid so introduced. Thus, an "expression vector" contains nucleic acids (ordinarily DNA) to be expressed by the host cell. Optionally, the expression vector can be contained in materials to aid in achieving entry of the nucleic acids into the host cell, such as the materials associated with a virus, liposome, protein coating, or the like. Expression vectors suitable for use in various aspects and embodiments of the present disclosure include those into which a nucleic acid sequence can be, or has been, inserted, along with any preferred or required operational elements. Thus, an expression vector can be transferred into a host cell and, typically, replicated therein (although, on can also employ, in some embodiments, non-replicable vectors that provide for "transient" expression). In some embodiments, an expression vector that integrates into chromosomal, mitochondrial, or plastid DNA is employed. In other embodiments, an expression vector that replicates extrachromasomally is employed. Typical expression vectors include plasmids, and expression vectors typically contain the operational elements required for transcription of a nucleic acid in the vector. Such plasmids, as well as other expression vectors, are described herein or are well known to those of ordinary skill in the art.

The terms "ferment", "fermentative", and "fermentation" are used herein to describe culturing microbes under conditions to produce useful chemicals, including but not limited to conditions under which microbial growth, be it aerobic or anaerobic, occurs.

The term "heterologous" as used herein refers to a material that is non-native to a particular cell. For example, a nucleic acid is heterologous to a cell, and so is a "heterologous nucleic acid" with respect to that cell, if at least one of the following is true: 1) the nucleic acid is not naturally found in that cell (that is, it is an "exogenous" nucleic acid); 2) the nucleic acid is naturally found in a given host cell (that is, "endogenous to"), but the nucleic acid or the RNA or protein resulting from transcription and translation of this nucleic acid is produced or present in the host cell in an unnatural (e.g., greater or lesser than naturally present) amount; 3) the nucleic acid contains a nucleotide sequence that encodes a protein endogenous to a host cell but differs in sequence from the endogenous nucleotide sequence that encodes that same protein (having the same or substantially the same amino acid sequence), typically resulting in the protein being produced in a greater amount in the cell, or in the case of an enzyme, producing a mutant version possessing altered (e.g., higher or lower or different) activity; and/or 4) the nucleic acid includes two or more nucleotide sequences that are not found in the same relationship to each other in the cell. As another example, a protein is heterologous to a host cell if it is produced by translation of RNA or the corresponding RNA is produced by transcription of a heterologous nucleic acid. Further, a protein is also heterologous to a host cell if it is a mutated version of an endogenous protein, and the mutation was introduced by genetic engineering.

The term "homologous", as well as variations thereof, such as "homology", refers to the similarity of a nucleic acid or amino acid sequence, typically in the context of a coding sequence for a gene or the amino acid sequence of a protein. Homology searches can be employed using a known amino acid or coding sequence (the "reference sequence") for a useful protein to identify homologous coding sequences or proteins that have similar sequences and thus are likely to perform the same useful function as the protein defined by the reference sequence. As will be appreciated by those of skill in the art, a protein having homology to a reference protein is determined, for example and without limitation, by a BLAST (https://blast.ncbi.nlm.nih.gov) search. A protein with high percent homology is highly likely to carry out the identical biochemical reaction as the reference protein. In some cases, two enzymes having greater than 50% identity will carry out identical biochemical reactions, and the higher the identity, i.e., 50%, 60%, 70%, 80%, 90% or greater than 95% identity, the more likely the two proteins have the same or similar function. A protein with at least 60% homology, and in some cases, at least 45% homology, to its reference protein is defined as substantially homologous. Proteins that share a specific function are not always defined or limited by percent sequence identity. In some cases, a protein with low percent sequence identity to a reference protein is able to carry out the identical biochemical reaction as the reference protein. Such proteins may share three-dimensional structure which enables shared specific functionality, but not necessarily sequence similarity. Such proteins may share an insufficient amount of sequence similarity to indicate that they are homologous via evolution from a common ancestor and would not be identified by a BLAST search or other sequence-based searches. Thus, in some embodiments of the present disclosure, homologous proteins comprise proteins that lack substantial sequence similarity but share substantial functional similarity and/or substantial structural similarity.

The terms "host cell", "host microorganism" and "host microbe" are used interchangeably herein to refer to a living cell that can be (or has been) transformed via insertion of an expression vector. A host cell or microorganism as described herein may be a prokaryotic cell (e.g., a microorganism of the kingdom Eubacteria) or a eukaryotic cell. As will be appreciated by one of skill in the art, a prokaryotic cell lacks a membrane-bound nucleus, while a eukaryotic cell has a membrane-bound nucleus.

The terms "isolated" or "pure" refer to material that is substantially, e.g., greater than 50% or greater than 75%, or essentially, e.g., greater than 90%, 95%, 98% or 99%, free of components that normally accompany it in its native state, e.g., the state in which it is naturally found or the state in which it exists when it is first produced. Additionally, any reference to a "purified" material is intended to refer to an isolated or pure material.

As used herein, the term "nucleic acid" and variations thereof shall be generic to polydeoxyribonucleotides (containing 2-deoxy-D-ribose), polyribonucleotides (containing D-ribose), segments of polydeoxyribonucleotides, and segments of polyribonucleotides. "Nucleic acid" can also refer to any other type of polynucleotide that is an N-glycoside of a purine or pyrimidine base, and to other polymers containing nonnucleotidic backbones, provided that the polymers contain nucleobases in a configuration that allows for base pairing and base stacking, as found in DNA and RNA. As used herein, the symbols for nucleotides and polynucleotides are those recommended by the IUPAC-IUB Commission of Biochemical Nomenclature (Biochem. 9:4022, 1970). A "nucleic acid" may also be referred to herein with respect to its sequence, the order in which different nucleotides occur in the nucleic acid, as the sequence of nucleotides in a nucleic acid typically defines its biological activity, e.g., as in the sequence of a coding region, the nucleic acid in a gene composed of a promoter and coding region, which encodes the product of a gene, which may be an RNA, e.g., a rRNA, tRNA, or mRNA, or a protein (where a gene encodes a protein, both the mRNA and the protein are "gene products" of that gene).

In the present disclosure, the term "genetic disruption" refers to several ways of altering genomic, chromosomal or plasmid-based gene expression. Genetic disruptions encompass nucleic acid deletions, nucleic acid insertions, nucleic acid substitutions, nucleic acid mutations, knockouts, premature stop codons and transcriptional promoter modifications. In the present disclosure, "genetic disruption" is used interchangeably with "genetic modification", "genetic mutation" and "genetic alteration." Genetic disruptions give rise to altered gene expression and or altered protein activity. Altered gene expression encompasses decreased, eliminated and increased gene expression levels. In some examples, gene expression results in protein expression, in which case the term "gene expression" is synonymous with "protein expression".

The term "operably linked" refers to a functional linkage between a nucleic acid expression control sequence (such as a promoter, ribosome-binding site, and transcription terminator) and a second nucleic acid sequence, the coding sequence or coding region, wherein the expression control sequence directs or otherwise regulates transcription and/or translation of the coding sequence.

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

As used herein, the term "recombinant" refers to the alteration of genetic material by human intervention. Typically, recombinant refers to the manipulation of DNA or RNA in a cell or virus or expression vector by molecular biology (recombinant DNA technology) methods, including cloning and recombination. Recombinant can also refer to manipulation of DNA or RNA in a cell or virus by random or directed mutagenesis. A "recombinant" cell or nucleic acid can typically be described with reference to how it differs from a naturally occurring counterpart (the "wild-type"). In addition, any reference to a cell or nucleic acid that has been "engineered" or "modified" and variations of those terms, is intended to refer to a recombinant cell or nucleic acid.

The terms "transduce", "transform", "transfect", and variations thereof as used herein refers to the introduction of one or more nucleic acids into a cell. For practical purposes, the nucleic acid must be stably maintained or replicated by the cell for a sufficient period of time to enable the function(s) or product(s) it encodes to be expressed for the cell to be referred to as "transduced", "transformed", or "transfected". As will be appreciated by those of skill in the art, stable maintenance or replication of a nucleic acid may take place either by incorporation of the sequence of nucleic acids into the cellular chromosomal DNA, e.g., the genome, as occurs by chromosomal integration, or by replication extrachromosomally, as occurs with a freely-replicating plasmid. A virus can be stably maintained or replicated when it is "infective": when it transduces a host microorganism, replicates, and (without the benefit of any complementary virus or vector) spreads progeny expression vectors, e.g., viruses, of the same type as the original transducing expression vector to other microorganisms, wherein the progeny expression vectors possess the same ability to reproduce.

As used herein, "isobutyric acid" is intended to mean the molecule having the chemical formula $(CH_3)_2CHCO_2H$ and a molecular mass of 88.11 g/mol (CAS #79-31-2). The terms "isobutyric acid", "isobutanoic acid", "2-methylpropanoic acid", "dimethylacetic acid", "isopropylformic acid" and "2-methylpropionic acid" are used interchangeably in the present disclosure, and practitioners skilled in the art understand that these terms are synonyms.

Herein, "isobutyrate" is also used interchangeably with "isobutyric acid", "isobutyrate anion" and practitioners skilled in the art understand that these terms are synonyms. In conditions with pH values higher than the pKa of isobutyric acid (e.g., about pH>4.84 when using a sodium base, such as sodium hydroxide), isobutyric acid is deprotonated to the isobutyrate anion $C_4H_7O_2^-$.

The term "isobutyrates" is intended to mean a variety of isobutyrate salt forms and is used interchangeably with "isobutyrate salts". The isobutyrate anion is capable of forming an ionic bond with a cation to produce an isobutyrate salt. Non-limiting examples of isobutyrates include ammonium isobutyrate (CAS #22228-82-6), calcium isobutyrate (CAS #533-09-4), potassium isobutyrate (CAS #19455-20-0), and sodium isobutyrate (CAS #996-30-5).

As used herein, "isobutyric acid" is defined as "bio-based isobutyric acid" and "isobutyrate" is defined as "bio-based isobutyrate." As used herein, the prefix "bio-" or the adjective "bio-based" may be used to distinguish e biologically-produced isobutyric acid and isobutyrates from those that are derived from petroleum feedstocks. The isobutyric acid and isobutyrates of the present disclosure are synthesized from biologically produced organic components by a fermenting microorganism. For example, isobutyric acid and isobutyrates are synthesized from the fermentation of a carbon source, for example sugars, by recombinant host cells of the present disclosure The term "byproduct" or "by-product" means an undesired chemical related to the biological production of a target molecule. In the present disclosure, "byproduct" is intended to mean any amino acid, amino acid precursor, chemical, chemical precursor, organic acid, organic acid precursor, biofuel, biofuel precursor, or small molecule, that may accumulate during biosynthesis of isobutyric acid. In some cases, "byproduct" accumulation may decrease the yields, titers or productivities of the target product (e.g., isobutyric acid) in a fermentation.

The redox cofactor nicotinamide adenine dinucleotide, NAD, comes in two forms—phosphorylated and un-phosphorylated. As used herein, the term "NAD(P)" refers to either phosphorylated (NADP) and/or un-phosphorylated (NAD) forms and encompasses oxidized versions ($NAD^+$ and $NADP^+$) and reduced versions (NADH and NADPH) of both forms. The term "$NAD(P)^+$" refers to the oxidized versions of phosphorylated and un-phosphorylated NAD, i.e., $NAD^+$ and $NADP^+$. Similarly, the term "NAD(P)H" refers to the reduced versions of phosphorylated and un-phosphorylated NAD, i.e., NADH and NADPH. When NAD(P)H is used to describe the redox cofactor in an enzyme catalyzed reaction, it indicates that NADH and/or NADPH is used. Similarly, when $NAD(P)^+$ is the notation used, it indicates that $NAD^+$ and/or $NADP^+$ is used. Those skilled in the art will also appreciate that while many proteins may only bind either a phosphorylated or un-phosphorylated cofactor, there are redox cofactor promiscuous proteins, natural or engineered, that are indiscriminate; in these cases, the protein may use either NADH and/or NADPH.

Various values for temperatures, titers, yields, oxygen transfer rate (OTR), and pH are recited in the description and in the claims. It should be understood that these values are not exact. However, the values can be approximated to the rightmost/last/least significant figure, except where otherwise indicated. For example, a temperature range of from about 30° C. to about 42° C. covers the range 25° C. to 44° C. It should be understood that numerical ranges recited can also include the recited minimum value and the recited maximum value when the values are approximated to the rightmost/last/least significant figure. For example, a temperature range of from about 25° C. to about 50° C. covers the range of 25° C. to 50° C.

Recombinant Host Cells for Production of Isobutyric Acid
Host Cells

The present disclosure provides recombinant host cells engineered to produce isobutyric acid, wherein the recombinant host cells may contain one or more heterologous nucleic acids encoding one or more isobutyric acid pathway enzymes. In certain embodiments, the recombinant host cells may further contain one or more heterologous nucleic acids encoding ancillary gene products (i.e., gene products other than the isobutyric acid pathway enzymes) that improve yields, titers and/or productivities of isobutyric acid. In particular embodiments, the recombinant cells further contain genetic disruptions that improve yields, titers and/or productivities of isobutyric acid. In some embodiments, the recombinant host cells are capable of producing isobutyric acid under aerobic conditions. In some embodiments, the recombinant host cells are capable of producing isobutyric acid under substantially anaerobic conditions.

In many embodiments, the recombinant host cells contain one or more heterologous nucleic acids encoding an isobutyric acid pathway enzyme. The recombinant host cells produce isobutyric acid at increased titers, yields and productivities host cells that do not contain the heterologous nucleic acids.

Any suitable host cell may be used in practice of the methods of the present disclosure, and examples of host cells useful in the compositions and methods provided herein include archaeal, prokaryotic, or eukaryotic cells. In some embodiments of the present disclosure, the recombinant host cell is a prokaryotic cell. In some embodiments of the present disclosure, the recombinant host cell is a eukaryotic cell. In some embodiments of the present disclosure, the recombinant host cell is a *Pichia kudriavzevii* (*P. kudriavzevii*) strain. Methods of construction and genotypes of these recombinant host cells are described herein.

Eukaryotic Cells

In some embodiments, eukaryotic cells are suitable for use in accordance with methods of the present disclosure, so long as the engineered host cell is capable of growth and/or product formation. Illustrative examples of eukaryotic host cells provided by the present disclosure include, but are not limited to, cells belonging to the genera *Aspergillus, Crypthecodinium, Cunninghamella, Entomophthora, Mortierella, Mucor, Neurospora, Pythium, Schizochytrium, Thraustochytrium, Trichoderma*, and *Xanthophyllomyces*. Examples of eukaryotic strains include, but are not limited to *Aspergillus niger, Aspergillus oryzae, Crypthecodinium cohnii, Cunninghamella, japonica, Entomophthora coronata, Mortierella alpina, Mucor circinelloides, Neurospora crassa, Pythium ultimum, Schizochytrium limacinum, Thraustochytrium aureum, Trichoderma reesei* and *Xanthophyllomyces dendrorhous*. Illustrative examples of eukaryotic host cells provided by the present disclosure also include yeast cells, as detailed below.

Yeast Cells

In some embodiments of the present disclosure, the recombinant host cell is a yeast cell. Yeast cells are excellent host cells for construction of recombinant metabolic pathways containing heterologous enzymes catalyzing production of small-molecule products. There are established molecular biology techniques and nucleic acids encoding genetic elements necessary for construction of yeast expression vectors, including, but not limited to, promoters, origins of replication, antibiotic resistance markers, auxotrophic markers, terminators, and the like. Techniques for integration/insertion of nucleic acids into the yeast chromosome by homologous recombination are also well established. Yeast also offers a number of advantages as an industrial fermentation host. Yeast cells can generally tolerate high concentrations of organic acids and maintain cell viability at low pH and can grow under both aerobic and anaerobic culture conditions, and there are established fermentation broths and fermentation protocols. This characteristic results in efficient product biosynthesis when the host cell is supplied with a carbohydrate carbon source. Also, from a process standpoint, the ability to run fermentations under substantially anaerobic conditions can decrease production cost.

In various embodiments, yeast cells useful in the methods of the present disclosure include yeasts of the genera *Aciculoconidium, Ambrosiozyma, Arthroascus, Arxiozyma, Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkara, Dipodascopsis, Dipodascus, Eeniella, Endomycopsella, Eremascus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella, Sakaguchia, Saturnospora, Schizoblastosporion, Schizosaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, Zygosaccharomyces, Zygowilliopsis,* and *Zygozyma,* among others.

In various embodiments, the yeast cell is of a species selected from the non-limiting group including *Candida albicans, Candida ethanolica, Candida guilliermondii, Candida krusei, Candida lipolytica, Candida methanosorbosa, Candida sonorensis, Candida tropicalis, Candida utilis, Cryptococcus curvatus, Hansenula polymorpha, Issatchenkia orientalis, Kluyveromyces lactis, Kluyveromyces marxianus, Kluyveromyces thermotolerans, Komagataella pastoris, Lipomyces starkeyi, Pichia angusta, Pichia deserticola, Pichia galeiformis, Pichia kodamae, Pichia kudriavzevii (P. kudriavzevii), Pichia membranaefaciens, Pichia methanolica, Pichia pastoris, Pichia salicaria, Pichia stipitis, Pichia thermotolerans, Pichia trehalophila, Rhodosporidium toruloides, Rhodotorula glutinis, Rhodotorula graminis, Saccharomyces bayanus, Saccharomyces boulardi, Saccharomyces cerevisiae (S. cerevisiae), Saccharomyces kluyveri, Schizosaccharomyces pombe (S. pombe)* and *Yarrowia lipolytica.*

The Crabtree phenomenon refers to the capability of yeast cells to convert glucose to alcohol in the presence of high sugar concentrations and oxygen instead of producing biomass via the tricarboxylic acid (TCA) cycle. Yeast cells produce alcohol to prevent growth of competing microorganisms in high sugar environments, which yeast cells can utilize later on when the sugars are depleted. One skilled in the art will recognize that many yeast can typically use two pathways to produce ATP from sugars: the first involves the conversion of sugars (via pyruvate) to carbon dioxide via the TCA cycle, and the second involves the conversion of sugars (via pyruvate) to ethanol. Yeast cells that display a Crabtree effect (known as Crabtree-positive yeast cells) are able to simultaneously use both pathways. Yeast cells that do not display a Crabtree effect (known as Crabtree-negative yeast cells) will only convert pyruvate to ethanol at high yields when oxygen is absent.

In some embodiments of the present disclosure, the host cell is a Crabtree-positive yeast cell. In other embodiments, the host cell is a Crabtree-negative yeast cell. It may be advantageous to use a Crabtree-negative yeast to produce isobutyric acid because high glucose concentrations can be maintained during product biosynthesis without ethanol accumulation; ethanol is an undesired byproduct in isobutyric acid production. For example, *P. kudriavzevii* does not produce appreciable amounts of ethanol from pyruvate at high glucose concentrations in the presence of oxygen, and as such is a Crabtree-negative yeast. In some embodiments, the host cell is *P. kudriavzevii.*

In certain embodiments, the recombinant yeast cells provided herein are engineered by the introduction of one or more genetic modifications (including, for example, heterologous nucleic acids encoding enzymes and/or the disruption of native nucleic acids encoding enzymes) into a Crabtree-negative yeast cell. In certain of these embodiments, the host cell belongs to the *Pichia/Issatchenkia/Saturnispora/Dekkera* clade. In certain of these embodiments, the host cell belongs to the genus selected from the group including *Pichia, Issatchenkia,* or *Candida.* In certain embodiments, the host cell belongs to the genus *Pichia,* and in some of these embodiments the host cell is *P. kudriavzevii.* Members of the *Pichia/Issatchenkia/Saturnispora/Dekkera* or the *Saccharomyces* clade are identified by analysis of their 26S ribosomal DNA using the methods described by Kurtzman C. P., and Robnett C. J., ("Identification and Phylogeny of Ascomycetous Yeasts from Analysis of Nuclear Large Subunit (26S) Ribosomal DNA Partial Sequences", Atonie van Leeuwenhoek 73(4):331-371; 1998). Kurtzman and Robnett report analysis of approximately 500 ascomycetous yeasts were analyzed for the extent of divergence in the variable D1/D2 domain of the large subunit (26S) ribosomal DNA. Host cells encompassed by a clade exhibit greater sequence identity in the D1/D2 domain of the 26S ribosomal subunit DNA to other host cells within the clade as compared to host cells outside the clade. Therefore, host cells that are members of a clade (e.g., the *Pichia/Issatchenkia/Saturnispora/Dekkera* or *Saccharomyces* clades) can be identified using the methods of Kurtzman and Robnett.

In certain embodiments of the present disclosure, the recombinant host cells are engineered by introduction of one or more genetic modifications into a Crabtree-positive yeast cell. In certain of these embodiments, the host cell belongs to the *Saccharomyces* clad. In certain of these embodiments, the host cell belongs to a genus selected from the group including *Saccharomyces, Schizosaccharomyces, Brettanomyces, Torulopsis,* Nematospora and Nadsonia. In certain embodiments, the host cell belongs to the genus *Saccharomyces,* and in one of these embodiments the host cell is *S. cerevisiae.*

Prokaryotic Cells

In an embodiment of the present disclosure, the recombinant host cell is a prokaryotic cell. Prokaryotic cells are suitable host cells for construction of recombinant metabolic pathways including heterologous enzymes catalyzing production of small-molecule products. Prokaryotic cells may be archaeal cells or bacterial cells, as further detailed herein.

Archaeal Cells

Archaeal cells are also suitable for use in accordance with methods of the present disclosure, and in some embodiments of the present disclosure, the recombinant host cell is an archaeal cell. Illustrative examples of recombinant archaea host cells provided by the present disclosure include, but are not limited to, cells belonging to the genera *Aeropyrum, Archaeglobus, Halobacterium, Methanococcus, Methanobacterium, Pyrococcus, Sulfolobus,* and *Thermoplasma.* Examples of archaea strains include, but are not limited to *Archaeoglobus fulgidus, Halobacterium* sp., *Methanococcus jannaschii, Methanobacterium thermoautotrophicum, Thermoplasma acidophilum, Thermoplasma volcanium, Pyrococcus horikoshii, Pyrococcus abyssi,* and *Aeropyrum pernix.*

Bacterial Cells

In an embodiment of the present disclosure, the recombinant host cell is a bacterial cell. Bacterial cells are suitable host cells for construction of recombinant metabolic pathways including heterologous enzymes catalyzing production of small-molecule products. Illustrative examples of recombinant bacterial host cells include, but are not limited to, cells belonging to the genera *Agrobacterium, Alicyclobacillus, Anabaena, Anacystis, Arthrobacter, Azobacter, Bacillus, Brevibacterium, Chromatium, Clostridium, Corynebacterium, Enterobacter, Envinia, Escherichia, Lactobacillus, Lactococcus, Mesorhizobium, Methylobacterium, Microbacterium, Pantoea, Phormidium, Pseudomonas, Rhodobacter, Rhodopseudomonas, Rhodospirillum, Rhodococcus, Salmonella, Scenedesmun, Serratia, Shigella, Staphylococcus, Strepromyces, Synnecoccus,* and *Zymomonas.* Examples of bacterial strains include, but are not limited to, *Bacillus subtilis (B. subtilis), Brevibacterium ammoniagenes, Bacillus amyloliquefacines, Brevibacterium ammoniagenes, Brevibacterium immariophilum, Clostridium acetobutylicum, Clostridium beigerinckii, Corynebacterium glutamicum (C. glutamicum), Enterobacter sakazakii, Escherichia coli (E. coli), Lactobacillus acidophilus, Lactococcus lactis, Mesorhizobium loti, Pantoea ananatis (P. ananatis), Pseudomonas aeruginosa, Pseudomonas mevalonii, Pseudomonas pudita, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei,* and *Staphylococcus aureus.*

In some embodiments of the present disclosure, the recombinant host cell is selected from the group including *Corynebacterium glutamicum, Escherichia coli,* and *Lactococcus lactis.* In one embodiment, the recombinant host cell is *Escherichia coli.* In another embodiment, the recombinant host cell is *Lactococcus lactis.*

Isobutyric Acid Pathway Enzymes

Provided herein in certain embodiments are recombinant host cells having at least one active isobutyric acid pathway from pyruvate to isobutyric acid. Recombinant host cells having an active isobutyric acid pathway as used herein produce active enzymes necessary to catalyze each metabolic reaction in an isobutyric acid pathway, and therefore are capable of producing isobutyric acid in measurable yields and/or titers when cultured under suitable conditions. Recombinant host cells having an active isobutyric acid pathway contain one or more heterologous nucleic acids encoding isobutyric acid pathway enzymes and are capable of producing isobutyric acid.

In certain embodiments, recombinant host cells of the present disclosure have an isobutyric acid pathway that proceeds via pyruvate (see, e.g. Table 1). This isobutyric pathway, as described herein, includes five enzymes: acetolactate synthase (EC 2.2.1.6), ketol-acid reductoisomerase (EC 1.1.1.86), dihydroxy-acid dehydratase (EC 4.2.1.9), branched-chain-2-oxoacid decarboxylase (EC 4.1.1.72) and isobutyraldehyde dehydrogenase (EC 1.2.1.5). In this pathway, all five isobutyric acid pathway enzymes are required to convert pyruvate to isobutyric acid.

TABLE 1

Enzymes Used To Convert Pyruvate to Isobutyric Acid

| EC # | Enzyme name | Reaction catalyzed |
| --- | --- | --- |
| 2.2.1.6 | Acetolactate synthase | 2 Pyruvate → 2-Acetolactate + $CO_2$ |
| 1.1.1.86 | Ketol-acid reductoisomerase | 2-Acetolactate + Reduced cofactor → 2,3-Dihydroxy-3-methylbutanoate + Oxidized cofactor |
| 4.2.1.9 | Dihydroxy-acid dehydratase | 2,3-Dihydroxy-3-methylbutanoate → 3-Methyl-2-oxobutanoate + $H_2O$ |
| 4.1.1.72 | Branched-chain-2-oxoacid decarboxylase | 3-Methyl-2-oxobutanoate → Isobutyraldehyde + $CO_2$ |
| 1.2.1.5 | Isobutyraldehyde dehydrogenase | Isobutyraldehyde + $H_2O$ + Oxidized cofactor Isobutyric acid + Reduced cofactor |

One advantage of the described isobutyric acid pathway is that all five isobutyric acid pathway reactions are thermodynamically irreversible (i.e., have a negative Gibbs free energy such that greater than about 99% of reaction flux is calculated to be in the forward direction under physiological conditions—1 mM metabolite concentrations, 25° C., pH 7.0, and 0.1 M ionic strength—typically observed in a yeast) and three of the five isobutyric acid pathway reactions are catalyzed by unidirectional enzymes (i.e., where the enzyme mechanism does not permit the reverse reaction). Enzymes catalyzing either thermodynamically or mechanistically irreversible reactions are referred to herein as irreversible enzymes. As the pathway intermediates pass through these steps, they become locked into the portion of the isobutyric acid pathway downstream of each irreversible enzyme. Generally speaking, when multiple enzymes in a metabolic pathway are irreversible, this helps to increase product yields, titers, and productivities. A feature that is particularly advantageous in the described isobutyric acid pathway is that both the first and last two isobutyric acid pathway steps are thermodynamically and mechanistically irreversible; thus, there is a strong driving force both pushing carbon into the isobutyric acid pathway and out of the isobutyric acid pathway. In some embodiments of the present disclosure, the recombinant host cell contains an isobutyric acid pathway wherein some or all reaction steps are thermodynamically and/or mechanistically irreversible.

In addition to the specific isobutyric acid pathway steps being thermodynamically favored, the conversion of glucose to isobutyric acid is thermodynamically favored. The calculated cumulative change in Gibbs free energy at 1 mM metabolite concentrations, 25° C., pH 7.0, and 0.1 M ionic strength (i.e., $\Delta_r G'''$) for the conversion of glucose to isobutyric acid using the described isobutyric acid pathway is negative, and thus strongly favors product formation. The advantaged thermodynamics of the pathway will help to achieve high isobutyric acid yields, titers and productivities. The conversion of glucose to isobutyric acid using the isobutyric pathway described herein has a calculated $\Delta_r G'''$ of −228.7+/−5.1 kJ/mol, indicative of a strong driving force that pushes the reaction to completion. Second, the pathway has net accumulation of 2 mol of ATP for every mol of isobutyric acid produced in the host cell cytosol from glucose, which can be used to help drive product export and support normal cell maintenance. Third, the balanced metabolic pathway requires a relatively low amount of oxygen (in fermentations where oxygen is used as the terminal electron acceptor) to sink excess NADH produced from pathway activity. In some embodiments of this disclosure, the recombinant host cell contains an isobutyric acid pathway providing a stoichiometric yield of 2 ATP per glucose converted to isobutyric acid in the host cell cytosol.

In certain embodiments, recombinant host cells may contain one or more heterologous nucleic acids encoding one, two, three, four, or all five, of the aforementioned isobutyric acid pathway enzymes or any combination thereof, wherein the heterologous nucleic acid is expressed in sufficient amounts to produce isobutyric acid.

In various embodiments, recombinant host cells may contain multiple copies of a single heterologous nucleic acid and/or multiple copies of two or more heterologous nucleic acids. Recombinant host cells including multiple heterologous nucleic acids may contain any number of heterologous nucleic acids.

The recombinant host cells of the present disclosure may include recombinant host cells that employ combinations of metabolic reactions for biosynthetically producing the compounds of the present disclosure. The biosynthesized compounds can be produced intracellularly and/or secreted into the fermentation medium. The biosynthesized compounds produced by the recombinant host cells may include isobutyric acid, and the products and intermediates of the isobutyric acid pathway, namely acetolactate, 2,3-dihydroxy-3-methylbutanoate, 3-methyl-2-oxobutanoate, and isobutyraldehyde. The relationship of these compounds with respect to the metabolic reactions described herein is depicted in FIG. 1.

The present disclosure also provides consensus sequences useful in identifying and/or constructing isobutyric acid pathway enzymes suitable for use in accordance with the disclosed methods. An enzyme encompassed by a consensus sequence provided herein has an enzymatic activity that is identical, or essentially identical, or at least substantially similar with respect to ability to catalyze the reaction performed by one of the enzymes exemplified herein. Thus, for example, an acetolactate synthase encompassed by an acetolactate synthase consensus sequence provided herein has an enzymatic activity that is identical, or essentially identical, or at least substantially similar with respect to its ability to convert two molecules of pyruvate to one molecule acetolactate and one molecule $CO_2$.

Enzymes also useful in the compositions and methods provided herein include those that are homologous to consensus sequences provided by the disclosure. As noted above, any protein substantially homologous to an enzyme described herein can be used in a host cell of the disclosure. The percent sequence identity of an enzyme relative to a consensus sequence is determined by aligning the enzyme sequence against the consensus sequence. Those skilled in the art will recognize that various sequence alignment algorithms are suitable for aligning an enzyme with a consensus sequence. See, for example, Needleman, S B, et al, "A general method applicable to the search for similarities in the amino acid sequence of two proteins." Journal of Molecular Biology 48 (3): 443-53 (1970). Following alignment of the enzyme sequence relative to the consensus sequence, the percentage of positions where the enzyme possesses an amino acid described by the same position in the consensus sequence determines the percent sequence identity. In various embodiments, these consensus sequences may include active site amino acid residues believed to be necessary (although this disclosure is not to be limited by any theory of mechanism of action) for substrate recognition and reaction catalysis, as described below.

In addition to identification of useful enzymes by percent sequence identity with a given consensus sequence, enzymes useful in the compositions and methods provided herein can also be identified by the occurrence of highly conserved amino acid residues in the query protein sequence relative to a consensus sequence. For each consensus sequence provided herein, a number of highly conserved amino acid residues are described. Enzymes useful in the compositions and methods provided herein include those that may include a substantial number, and sometimes all, of the highly conserved amino acids at positions aligning with the indicated residues in the consensus sequence. Those skilled in the art will recognize that, as with percent identity, the presence or absence of these highly conserved amino acids in a query protein sequence can be determined following alignment of the query protein sequence relative to a given consensus sequence and comparing the amino acid found in the query protein sequence that aligns with each highly conserved amino acid specified in the consensus sequence.

Acetolactate Synthase

Acetolactate synthase (ALS) (EC 2.2.1.6) as described herein catalyzes the conversion of two pyruvate molecules to 2-acetolacate and $CO_2$ (Table 1). Any enzyme is suitable for use in accordance with the disclosed methods so long as the enzyme is capable of catalyzing an ALS reaction. There are two types of acetolactate synthase (ALS) enzymes: anabolic ALS enzymes and catabolic ALS enzymes. Anabolic ALS enzymes are primarily found in plants, fungi, and bacteria, are involved in the biosynthesis of branched-chain amino acids, use a flavin adenine dinucleotide (FAD) cofactor, and are composed of multiple subunits, often including a regulatory subunit. By comparison, catabolic ALS enzymes are generally found only in some bacteria, have FAD-independent functionality, and lack a regulatory subunit. Either anabolic or catabolic ALSs are suitable for use in accordance with the methods of this disclosure. Generally speaking, catabolic ALSs are preferred since they do not require an FAD cofactor and do not possess a regulatory subunit.

Catabolic Acetolactate Synthases

In many embodiments, the acetolactate synthase is derived from a bacterial source. In many of these embodiments, the acetolactate synthase is derived from a host cell belonging to a genus selected from the group including

*Bacillus, Enterobacter,* and *Klebsiella.* In some embodiments, the acetolactate synthase is derived from *Bacillus subtilis.*

Non-limiting examples of catabolic ALS enzymes include those derived from *Bacillus subtilis* (UniProt ID: Q04789), *Bacillus pumilus* (UniProt ID: B4AJ14), *Bacillus licheniformis* (UniProt ID: T5HBH2), *Bacillus amyloliquefaciens* (UniProt ID: I2CAY3), *Listeria innocua* (UniProt ID: Q92A08), *Bacillus pseudomycoides* (UniProt ID: C3BGG6), *Bacillus cereus* (UniProt ID: C2Q7Y8), *Bacillus cereus* (UniProt ID: R8PL10), *Bacillus thuringiensis* (UniProt ID: C3DFV1), *Enterobacter cloacae* (UniProt ID: V3F760), and/or *Klebsiella pneumoniae* (UniProt ID: P27696).

In some embodiments, the ALS enzyme is the *Bacillus subtilis* AlsS protein (abbv. BsALSS; UniProt ID: Q04789; SEQ ID NO: 1).

In some embodiments, recombinant host cells may contain one or more heterologous nucleic acids encoding an ALS enzyme wherein the recombinant host cells are capable of producing isobutyric acid. In various embodiments, proteins suitable for use in accordance with methods of the present disclosure have ALS activity and may contain an amino acid sequence with at least 60%, at least 70%, at least 80%, at least 90%, or at least 95% sequence identity to SEQ ID NO: 1. In some embodiments, the recombinant host cell is a *P. kudriavzevii* strain.

Catabolic ALS Consensus Sequence #1; (SEQ ID NO: 19) provides the amino acid sequence of amino acids in which each position identifies the amino acid (if a specific amino acid is identified) or a subset of amino acids (if a position is identified as variable) most likely to be found at a specified position in a catabolic ALS enzyme. Those of skill in the art will recognize that fixed amino acids and conserved amino acids in these consensus sequences are identical to (in the case of fixed amino acids) or consistent with (in the case of conserved amino acids) with the wild-type sequence(s) on which the consensus sequence is based. Following alignment of a query protein with a consensus sequence provided herein, the occurrence of a dash ("–") in the aligned query protein sequence indicates an amino acid deletion in the query protein sequence relative to the consensus sequence at the indicated position. Likewise, the occurrence of a plus ("+") in the aligned consensus sequence indicates an amino acid addition in the query protein sequence relative to the consensus sequence at the indicated position. Amino acid additions and deletions are common to proteins encompassed by consensus sequences of this disclosure, and their occurrence is reflected as a lower percent sequence identity (i.e., amino acid addition or deletions are treated identically to amino acid mismatches when calculating percent sequence identity).

In various embodiments, ALS enzymes suitable for use in accordance with the methods of the present disclosure have ALS activity and may contain an amino acid sequence with at least 60%, at least 65%, or at least 70% sequence identity to SEQ ID NO: 19. For example, the BcALSS (SEQ ID NO: 1) sequence is 71% identical to consensus sequence SEQ ID NO: 19.

Many amino acids in SEQ ID NO: 19 are highly conserved and acetolactate synthases suitable for use in accordance with the methods of the present disclosure will include a substantial number, and sometimes all, of these highly conserved amino acids at positions aligning with the location of the indicated amino acid in SEQ ID NO: 19. The highly conserved amino acids in SEQ ID NO: 19 are G16, A17, L19, V21, L24, Q27, G28, V29, V32, F33, I35, P36, G37, A38, K39, I40, D41, V43, F44, D45, R58, H59, E60, N62, A63, A64, F65, M66, A67, A69, G71, R72, T74, G75, K76, G78, V79, L81, V82, T83, S84, G85, P86, G87, S89, N90, L91, T93, G94, T97, A98, E101, D103, P104, V105, V106, A107, G110, V112, R114, D116, K119, H122, Q123, S124, D126, A129, F131, P133, T135, K136, Y137, E140, V141, E149, N153, A154, F155, R156, A158, G164, S169, P171, Q172, D173, G193, A195, A210, P213, G218, R231, L233, P240, T244, Q246, A248, G249, G261, R262, G264, L265, F266, N268, Q269, G271, D272, L274, A278, D279, G285, P288, E290, Y291, P293, W296, N297, H306, D308, A312, Y318, P320, E323, L324, G326, I328, T331, H375, P376, L377, D396, G398, S399, I402, W403, R406, S419, N420, G421, Q423, T424, G426, V427, A428, L429, P430, W431, I433, A435, P440, K443, S446, S448, G449, D450, G451, G452, F453, L454, S456, M458, E459, L460, E461, T462, A463, V464, R465, H472, W475, D477, Y480, M482, V483, A484, Q486, K490, Y491, F499, G500, D503, A508, F511, G512, A513, G515, V518, L524, L528, G536, P537, P543, D545, Y546, D548, N549, and L552. In some embodiments, ALS enzymes suitable for use in accordance with the methods of this disclosure may include at least 60%, at least 70%, at least 80%, at least 85%, at least 90%, at least 95%, or sometimes all of these highly conserved amino acids at positions corresponding to (i.e., aligning with) the highly conserved amino acids identified in SEQ ID NO: 19. For example, SEQ ID NO: 1 includes 100% of these highly conserved amino acids at positions corresponding to their referenced positions in SEQ ID NO: 19. SEQ ID NO: 1 is a suitable ALS for use in accordance with the methods of the present disclosure. In some embodiments, each of these highly conserved amino acids are found in a desired ALS enzyme, as provided in SEQ ID NO: 19.

Ketol-Acid Reductoisomerase

Ketol-acid reductoisomerases (KARI) (EC 1.1.1.86) are a family of oxidoreductases that produce intermediates in the biosynthesis of branched-chain amino acids. The KARI enzymes described herein catalyze the conversion of 2-acetolactate and NAD(P)H to 2,3-dihydroxy-3-methylbutanoate and NAD(P)$^+$ (Table 1) and are used in the production of isobutyric acid in accordance with the methods of the present disclosure.

KARI enzymes typically utilize the cofactor NADP; NADPH is oxidized to NADP$^+$ during catalysis. In most cell types, the pool of NAD (which consists of reduced and oxidized forms, i.e., NADH and NAD$^+$, respectively) is larger than that of NADP. Under certain fermentation conditions, NADP may be even scarcer. Further, while interconversion of NADP with NAD can occur, the process is slow and inefficient. The limited availability and low regeneration rate of NADPH can hamper KARI enzyme turnover and isobutyric titers, yields or productivities during fermentation. Native KARI cofactor specificity can be altered, however, by standard microbial engineering techniques, and recombinant host cells can be designed to express modified KARI enzymes that utilize NADH, or NADH and NADPH non-selectively, instead of NADPH exclusively. The KARI enzymes of the present disclosure may include: 1) KARI enzymes that bind and oxidize NADH; 2) KARI enzymes that bind and oxidize NADPH; and/or 3) KARI enzymes that can indiscriminately bind and oxidize NADH and NADPH. In some embodiments of the present disclosure, the recombinant host cells may include a KARI enzyme that utilizes NADH as a cofactor and is capable of producing isobutyric acid. In some embodiments of the present disclosure, the recombinant host cell may include a KARI enzyme that utilizes NADPH as a cofactor and is capable of producing isobutyric acid. In some embodiments of the present disclosure, the recombinant host cell may include a KARI enzyme that utilizes NADH and/or NADPH as a cofactor and is capable of producing isobutyric acid.

Any enzyme is suitable for use in accordance with the methods of the present disclosure so long as the enzyme is capable of catalyzing the conversion of 2-acetolactate and NAD(P)H to 2,3-dihydroxy-3-methylbutanoate and NAD(P). In some embodiments, the KARI is derived from a bacterial source. In many of these embodiments, the KARI is derived from a host cell belonging to a genus selected from the group including *Arcobacter, Bacillus, Bradyrhizobium, Campylobacter, Cellvibrio, Clostridium, Corynebacterium, Escherichia, Lactococcus, Leuconostoc, Mycobacterium, Propionibacterium, Pseudomonas, Ralstonia, Rhodococcus, Saccharopolyspora, Staphylococcus, Streptococcus*, and *Streptomyces*. In one embodiment, the KARI is derived from *Escherichia coli*. In another embodiment, the KARI is derived from *Lactococcus lactis*.

Non-limiting examples of KARI enzymes include those derived from *Arcobacter butzleri* (UniProt ID: A8ERD8), *Bacillus cereus* (UniProt ID: Q81G13), *Bacillus pumilus* (UniProt ID: A8FFW6), *Bacillus subtilis* (UniProt ID: P37253), *Bradyrhizobium diazoefficiens* (UniProt ID: Q89G50), *Campylobacter fetus* (UniProt ID: A0RQ02), *Cellvibrio japonicus* (UniProt ID: B3PK17), *Clostridium beijerinckii* (UniProt ID: A6LPX8), *Clostridium novyi* (UniProt ID: A0Q0E9), *Corynebacterium aurimucosum* (UniProt ID: C3PFX1), *Corynebacterium efficiens* (UniProt ID: Q8FPX1), *Corynebacterium glutamicum* (UniProt ID: Q57179) *Escherichia coli* (UniProt ID: P05793), *Lactococcus lactis* (UniProt ID: Q02138), *Leuconostoc mesenteroides* (UniProt ID: Q03UU4), *Mycobacterium smegmatis* (UniProt ID: A0QUX8), *Propionibacterium acnes* (UniProt ID: Q6A7Z2), *Pseudomonas fluorescens* (UniProt ID: Q4K608), *Pseudomonas putida* (UniProt ID: Q88DZ0) *Pseudomonas syringae* (UniProt IDs: Q888N4 and Q4ZY66), *Ralstonia solanacearum* (UniProt ID: Q8XXN8), *Rhodococcus jostii* (UniProt ID: Q0S2H3), *Saccharopolyspora erythraea* (UniProt ID: A4FMQ5), *Staphylococcus aureus* (UniProt ID: A7X4M9), *Staphylococcus brevis* (UniProt ID: C2D2I9), *Staphylococcus hominis* (UniProt ID: A0A1L8Y8D1), *Streptococcus gordonii* (UniProt ID: A8AVN4), *Streptococcus suis* (UniProt ID: A4W3V8), and/or *Streptomyces coelicolor* (UniProt ID: Q9FBT8). In addition to the above listed bacterial KARI enzymes, suitable KARI enzymes can be derived from eukaryotic organisms. Most eukaryotic KARI enzymes are expressed in the mitochondria; however, expression of eukaryotic KARI comprising deletion of the N-terminal mitochondrial targeting sequences results in localization of the eukaryotic KARI to the host cell cytosol. A non-limiting example of a eukaryotic KARI suitable for use in producing isobutyric acid is *S. cerevisiae* mitochondrial Ilv5 (UniProt ID: P06168) comprising a deletion of the 47 N-terminal amino acids corresponding to the mitochondrial targeting sequence.

In a particular embodiment, the KARI enzyme is the *E. coli* IlvC protein (abbv. EcILVC; UniProt ID: P05793; SEQ ID NO: 2). In other embodiments, the KARI is *L. lactis* IlvC (abbv. LlILVC; UniProt ID: Q02138; SEQ ID NO: 21).

In other embodiments, the KARI is selected from the group including *Corynebacterium glutamicum* IlvC (UniProt ID: Q57179), *Lactococcus brevis* IlvC (UniProt ID: C2D2I9), *Lactococcus lactis* IlvC (UniProt ID: Q02138), *Pseudomonas fluorescens* IlvC (UniProt ID: Q4K608), *Pseudomonas putida* IlvC (UniProt ID: Q88DZ0), *Pseudomonas syringae* IlvC (UniProt ID: Q4ZY66), *Saccharomyces cerevisiae* mitochondrial Ilv5 (UniProt ID: P06168 comprising a deletion of the 47 N-terminal amino acids), and *Staphylococcus hominis* IlvC (UniProt ID: A0A1L8Y8D1). As described in Example 9, expression of each of the KARI enzymes listed in this group in recombinant *P. kudriavzevii* expressing the other isobutyric acid pathway proteins resulted in detectable amounts of isobutyric acid.

In many embodiments, the recombinant host cell may contain one or more heterologous nucleic acids encoding a KARI enzyme wherein the recombinant host cells are capable of producing isobutyric acid. In other embodiments, recombinant host cells may contain one or more heterologous nucleic acids encoding a protein with KARI activity wherein the recombinant host cells are capable of producing isobutyric acid. In various embodiments, proteins suitable for use in accordance with methods of the present disclosure have KARI activity and may include an amino acid sequence with at least 60%, at least 70%, at least 80%, at least 90%, or at least 95% sequence identity to SEQ ID NO: 2. In many embodiments, the recombinant host cell is *P. kudriavzevii* strain.

SEQ ID NO: 20 represents a Class I KARI Consensus Sequence which was constructed based on the KARI enzyme sequences from *Arcobacter butzleri, Bacillus cereus, Bacillus pumilus, Bacillus subtilis, Bradyrhizobium diazoefficiens, Campylobacter fetus, Cellvibrio japonicus, Clostridium beijerinckii, Clostridium novyi, Corynebacterium aurimucosum, Corynebacterium efficiens, Lactococcus lactis, Leuconostoc mesenteroides, Mycobacterium smegmatis, Propionibacterium acnes, Pseudomonas syringae, Ralstonia solanacearum, Rhodococcus jostii, Saccharopolyspora erythraea, Staphylococcus aureus, Streptococcus gordonii, Streptococcus suis*, and *Streptomyces coelicolor*. The KARI enzymes from each of these organisms is a short-form (Class I) KARI generally found in fungi and most bacteria; the short-from KARI enzymes are distinguished from long-form (Class II) KARI enzymes by the absence of a central insert found in the Class II enzymes that is the structural equivalent of one C-terminal domain in a pair of a Class I KARI subunits.

In various embodiments, KARI enzymes suitable for use in accordance with the methods of the present disclosure have KARI activity and may include an amino acid sequence with at least 60%, at least 65%, or at least 70% sequence identity to SEQ ID NO: 20. For example, the LIILVC (SEQ ID NO: 21) sequence is 66% identical to consensus sequence SEQ ID NO: 20.

Many amino acids in SEQ ID NO: 20 are highly conserved and KARI enzymes suitable for use in accordance with the methods of the present disclosure may include many of these highly conserved amino acids at positions aligning with the location of the indicated amino acid in SEQ ID NO: 20. In certain cases, a substantial number of these highly conserved amino acids will align; in others, all of these highly conserved amino acids will align. The highly conserved amino acids in SEQ ID NO: 20 are Y7, D10, G25, G27, Q29, G30, H31, A32, L37, G41, V44, A58, G62, A75, M79, P83, D84, F107, H109, G110, A130, P131, K132, P134, G135, R139, G145, P149, L151, G160, G174, G179, T183, E188, D192, L193, F194, G195, E196, Q197, V199, L200, G202, G203, L207, G211, A218, G219, Y220, E223, A225, Y226, F227, E228, H231, E232, K234, I236, V237, D238, L239, G244, S253, G259, G264, M276, L280, Q284, G286, G319, and R323. In various embodiments, KARI enzymes homologous to SEQ ID NO: 20 include at least 60%, at least 70%, at least 80%, at least 85%, at least 90%, at least 95%, or sometimes all of these highly conserved amino acids at positions corresponding to the highly conserved amino acids identified in SEQ ID NO: 20. For example, SEQ ID NO: 21 (LlILVC; UniProtID: Q02138) includes 100% of these highly conserved amino acids at positions corresponding to their referenced positions in SEQ ID NO: 20. SEQ ID NO: 21 is a suitable KARI for use in accordance with the methods of the present disclosure. In some embodiments, each of these highly conserved amino acids are found in a desired KARI enzyme, as provided in SEQ ID NO: 21.

Dihydroxy-Acid Dehydratase

Dihydroxy-acid dehydratase (DHAD) (EC 4.2.1.9) described herein catalyzes the conversion of 2,3-dihydroxy-3-methylbutanoate to 3-methyl-2-oxobutanoate and water (Table 1). Any enzyme is suitable for use in accordance with the disclosed methods, so long as the enzyme is capable of catalyzing an DHAD reaction.

In some embodiments, the DHAD enzyme is derived from a bacterial source. In many of these embodiments, the DHAD is derived from a host cell belonging to a genus selected from the group including *Arthrobacter, Acidovorax, Acinetobacter, Actinobacillus, Aeromonas, Agrobacterium, Bacillus, Bacteroides, Bifidobacterium, Burkholderia, Campylobacter, Chloroflexus, Clostridium, Corynebacterium, Lactococcus, Mycobacterium, Nocardioides, Polaromonas, Pseudoalteromonas, Rhodopseudomonas, Serratia, Staphylococcus, Stenotrophomonas, Streptococcus, Streptomyces, Vibrio,* and *Zymomonas*. In one embodiment, the DHAD is derived from *Lactococcus lactis*.

Non-limiting examples of DHAD enzymes suitable for use in accordance with the methods of the present disclosure include those derived from *Arthrobacter* sp. (UniProt ID: A0JXZ9), *Acidovorax citrulli* (UniProt ID: A1TMA7), *Acinetobacter baylyi* (UniProt ID: Q6FCR9), *Actinobacillus pleuropneumonias* (UniProt ID: A3MYG9), *Aeromonas hydrophila* (UniProt ID: A0KQS4), *Agrobacterium radiobacter* (UniProt ID: B9JDW2), *Bacillus clausii* (UniProt ID: Q5WEM9), *Bacillus subtilis* (UniProt ID: P51785), *Bacteroides vulgatus* (UniProt ID: A6L3E7), *Bifidobacterium longum* (UniProt ID: B7GUP9), *Burkholderia lata* (UniProt ID: Q39DS9), *Campylobacter fetus* (UniProt ID: A0RRN7), *Chloroflexus aurantiacus* (UniProt ID: A9WF68), *Clostridium novyi* (UniProt ID: A0Q0E8), *Corynebacterium aurimucosum* (UniProt ID: C3PFW7), *Lactococcus lactis* (UniProt ID: Q02139), *Mycobacterium leprae* (UniProt ID: 006069), *Mycobacterium* sp. (UniProt ID: A3PSS2), *Nocardioides* sp. (UniProt ID: A1SM84), *Polaromonas* sp. (UniProt ID: Q12BW0), *Pseudoalteromonas haloplanktis* (UniProt ID: Q3IJH1), *Rhodopseudomonas palustris* (UniProt ID: Q07IE7), *Serratia proteamaculans* (UniProt ID: A8GL60), *Staphylococcus carnosus* (UniProt ID: B9DMJ2), *Staphylococcus saprophyticus* (UniProt ID: Q49UX2), *Stenotrophomonas maltophilia* (UniProt ID: B4SMU1), *Streptococcus suis* (UniProt ID: A4W3W3), *Streptomyces griseus* (UniProt ID: B1VSL0), *Vibrio cholerae* (UniProt ID: A5F497), and/or *Zymomonas mobilis* (UniProt ID: Q5NLJ4).

In a particular embodiment, the DHAD enzyme is the *Lactococcus lactis* IlvD protein (abbv. LlILVD; UniProt ID Q02139; SEQ ID NO: 3). In an embodiment of the present disclosure, recombinant host cells may contain one or more heterologous nucleic acids encoding a DHAD enzyme wherein the recombinant host cell is capable of producing isobutyric acid. In another embodiment, recombinant host cells may contain one or more heterologous nucleic acids encoding a protein with DHAD activity wherein the recombinant host cell is capable of producing isobutyric acid. In various embodiments, proteins suitable for use in accordance with methods of the present disclosure have DHAD activity and may include an amino acid sequence with at least 60%, at least 70%, at least 80%, at least 90%, or at least 95% sequence identity to SEQ ID NO: 3. In many embodiments, the recombinant host cell is a *P. kudriavzevii* strain.

SEQ ID NO: 22 represents a DHAD Consensus Sequence #1 which was constructed based on the DHAD enzyme sequences from *Arthrobacter* sp. (UniProt ID: A0JXZ9), *Acidovorax citrulli* (UniProt ID: A1TMA7), *Acinetobacter baylyi* (UniProt ID: Q6FCR9), *Actinobacillus pleuropneumonias* (UniProt ID: A3MYG9), *Aeromonas hydrophila* (UniProt ID: A0KQS4), *Agrobacterium radiobacter* (UniProt ID: B9JDW2), *Bacillus clausii* (UniProt ID: Q5WEM9), *Bacillus subtilis* (UniProt ID: P51785), *Bacteroides vulgatus* (UniProt ID: A6L3E7), *Bifidobacterium longum* (UniProt ID: B7GUP9), *Burkholderia lata* (UniProt ID: Q39DS9), *Campylobacter fetus* (UniProt ID: A0RRN7), *Chloroflexus aurantiacus* (UniProt ID: A9WF68), *Clostridium novyi* (UniProt ID: A0Q0E8), *Corynebacterium aurimucosum* (UniProt ID: C3PFW7), *Lactococcus lactis* (UniProt ID: Q02139), *Mycobacterium leprae* (UniProt ID: 006069), *Mycobacterium* sp. (UniProt ID: A3PSS2), *Nocardioides* sp. (UniProt ID: A1SM84), *Polaromonas* sp. (UniProt ID: Q12BW0), *Pseudoalteromonas haloplanktis* (UniProt ID: Q3IJH1), *Rhodopseudomonas palustris* (UniProt ID: Q07IE7), *Serratia proteamaculans* (UniProt ID: A8GL60), *Staphylococcus carnosus* (UniProt ID: B9DMJ2), *Staphylococcus saprophyticus* (UniProt ID: Q49UX2), *Stenotrophomonas maltophilia* (UniProt ID: B4SMU1), *Streptococcus suis* (UniProt ID: A4W3W3), *Streptomyces griseus* (UniProt ID: B1VSL0), *Vibrio cholerae* (UniProt ID: A5F497), and *Zymomonas mobilis* (UniProt ID: Q5NLJ4).

In various embodiments, DHAD enzymes suitable for use in accordance with the methods of the present disclosure have DHAD activity and may include an amino acid sequence with at least 47%, at least 55%, at least 60%, at least 65%, or at least 70% sequence identity to SEQ ID NO: 22. For example, the LlILVD (SEQ ID NO: 3) sequence is 47% identical to consensus sequence SEQ ID NO: 22, and is therefore encompassed by consensus sequence SEQ ID NO: 22.

Many amino acids in SEQ ID NO: 22 are highly conserved and DHAD enzymes suitable for use in accordance with the methods of the present disclosure may include many of these highly conserved amino acids at positions aligning with the location of the indicated amino acid in SEQ ID NO: 22. In certain cases, a substantial number of these highly conserved amino acids will align; in others, all of these highly conserved amino acids will align. The highly conserved amino acids in SEQ ID NO: 22 are S6, G26, K34, P48, D81, G82, G89, M90, L94, S96, R97, I100, E105, D114, C122, D123, K124, P127, G128, G146, G151, G193, C195, G197, T200, A201, N202, E209, G212, A268, G276, G277, S278, N280, L283, H284, A287, P309, P316, G330, G331, G420, L425, G427, G433, K437, G450, A452, G482, P483, G485, P487, G488, M489, E491, M492, L493, T512, D513, G514, R515, S517, G518, G522, G526, H527, P530, E531, G536, D545, R568, A595, and G598. In various embodiments, DHAD enzymes homologous to SEQ ID NO: 22 contain at least 47%, at least 55%, at least 60%, at least 70%, at least 80%, at least 85%, at least 90%, at least 95%, or sometimes all of these highly conserved amino acids at positions corresponding to the highly conserved amino acids identified in SEQ ID NO: 22. For example, SEQ ID NO: 3

(LIILVD; UniProtID: Q02138) contains 100% of these highly conserved amino acids at positions corresponding to their referenced positions in SEQ ID NO: 22. SEQ ID NO: 3 is a suitable DHAD for use in accordance with the methods of the present disclosure. In some embodiments, each of these highly conserved amino acids are found in a desired DHAD enzyme, as provided in SEQ ID NO: 22.

Branched-Chain-2-Oxoacid Decarboxylase

Branched-chain-2-oxoacid decarboxylase (OADC) (EC 4.1.1.72) described herein catalyzes the conversion of 3-methyl-2-oxobutanoate to isobutyraldehyde and $CO_2$ (Table 1). Any enzyme is suitable for use in accordance with the disclosed methods so long as the enzyme is capable of catalyzing said conversion.

In some embodiments, the OADC enzyme is derived from a bacterial source. In many of these embodiments, the OADC is derived from a host cell belonging to a genus selected from the group including *Carnobacterium, Enterococcus,* and *Lactococcus*. In one embodiment, the OADC is derived from *Lactococcus lactis*.

Non-limiting examples of branched-chain-2-oxoacid decarboxylase include those derived from *Carnobacterium maltaromaticum* (UniProt ID: K8ENB2), *Enterococcus caccae* (UniProt ID: R3WVT4), *Enterococcus haemoperoxidus* (UniProt ID: R2SWI8), *Enterococcus moraviensis* (UniProt ID: R2QZ22), Influenza A virus (UniProt ID: A0A1X6), *Lactococcus lactis* KdcA (UniProt ID: Q6QBS4), *Lactococcus lactis* KivD (UniProt ID: Q684J7), *Lactococcus lactis* subsp. *cremoris* GE214 (UniProt ID: A0A084ABT7), *Lactococcus lactis* subsp. *cremoris* KW2 (UniProt ID: T2F5Q7), *Lactococcus lactis* subsp. *lactis* Dephy 1 (UniProt ID: U6ELQ5), *Lactococcus lactis* subsp. *lactis* IO-1 (UniProt ID: H5SZJ9), and *Lactococcus lactis* subsp. *lactis* KLDS 4.0325 (UniProt ID: U5PPW7).

In particular embodiments, the OADC enzyme is the *Lactococcus lactis* KivD protein (abbv. LlKIVD; UniProt ID Q684J7; SEQ ID NO: 4).

In some embodiments, recombinant host cells may include one or more heterologous nucleic acids encoding OADC wherein the recombinant host cells are capable of producing isobutyric acid. In other embodiments, recombinant host cells may include one or more heterologous nucleic acids encoding a protein with OADC activity wherein the recombinant host cells are capable of producing isobutyric acid. In various embodiments, enzymes suitable for use in accordance with methods of the present disclosure have OADC activity and contain an amino acid sequence with at least 60%, at least 70%, at least 80%, at least 90%, or at least 95% sequence identity to SEQ ID NO: 4. In many embodiments, the recombinant host cell is a *P. kudriavzevii* strain.

SEQ ID NO: 23 represents an OADC Consensus Sequence #1 which was constructed based on the OADC sequences from *Carnobacterium maltaromaticum* (UniProt ID: K8ENB2), *Enterococcus caccae* (UniProt ID: R3WVT4), *Enterococcus haemoperoxidus* (UniProt ID: R2SWI8), *Enterococcus moraviensis* (UniProt ID: R2QZ22), Influenza A virus (UniProt ID: A0A1X6), *Lactococcus lactis* KdcA (UniProt ID: Q6QBS4), *Lactococcus lactis* KivD (UniProt ID: Q684J7), *Lactococcus lactis* subsp. *cremoris* GE214 (UniProt ID: A0A084ABT7), *Lactococcus lactis* subsp. *cremoris* KW2 (UniProt ID: T2F5Q7), *Lactococcus lactis* subsp. *lactis* Dephy 1 (UniProt ID: U6ELQ5), *Lactococcus lactis* subsp. *lactis* IO-1 (UniProt ID: H5SZJ9), and *Lactococcus lactis* subsp. *lactis* KLDS 4.0325 (UniProt ID: U5PPW7).

In various embodiments, OADC enzymes suitable for use in accordance with the methods of the present disclosure have OADC activity and contain an amino acid sequence with at least 55%, at least 60%, at least 65%, at least 70%, at least 90%, or at least 95% sequence identity to SEQ ID NO: 23. For example, the LlKIVD (SEQ ID NO: 4) sequence is 95% identical to consensus sequence SEQ ID NO: 23.

Many amino acids in SEQ ID NO: 23 are highly conserved and OADC enzymes suitable for use in accordance with the methods of the present disclosure may contain many of these highly conserved amino acids at positions aligning with the location of the indicated amino acid in SEQ ID NO: 23. In certain cases, a substantial number of these highly conserved amino acids will align, in others, all of these highly conserved amino acids will align. The highly conserved amino acids in SEQ ID NO: 23 are Y2, T3, Y7, L8, L9, D10, R11, L12, E14, L15, G16, F21, G22, V23, P24, G25, D26, Y27, N28, L29, F31, L32, D33, W43, G45, N46, A47, N48, E49, L50, N51, A52, Y54, A56, D57, G58, Y59, A60, R61, T62, K63, A67, T70, T71, F72, G73, V74, G75, E76, L77, S78, A79, N81, G82, A84, G85, S86, A88, E89, P92, V93, I96, G98, P100, V104, Q105, K109, V111, H112, H113, T114, L115, D117, G118, F120, F123, A133, L137, N141, A142, E145, I146, D147, R148, V149, L150, P159, Y161, N163, L164, D167, A169, L180, L195, K197, L202, P208, G213, E215, S218, E222, P235, L239, G242, K243, E248, G255, Y257, G259, K267, V270, A273, D274, G280, L283, T284, D285, T288, F291, I301, L327, L354, Q356, W360, E364, T372, E376, Q377, G378, T379, S380, F381, F382, G383, K390, I396, G397, Q398, P399, L400, W401, G402, S403, I404, G405, T407, F408, P409, L412, G413, S414, Q415, A417, R422, H423, L424, L425, F426, I427, G428, D429, G430, S431, L432, Q433, L434, T435, Q437, E438, L439, G440, R444, K446, P449, F452, I454, N455, N456, G458, Y459, T460, V461, E462, R463, E464, I465, H466, G467, Y472, N473, D474, I475, P476, W478, Y480, L483, P484, F487, G488, V494, T501, E504, A512, D515, R518, W521, I522, E523, P532, L535, F542, A543, Q545, and N546. In various embodiments, OADC enzymes suitable for use in accordance with the methods of the present disclosure homologous to SEQ ID NO: 23 contain at least 60%, at least 70%, at least 80%, at least 85%, at least 90%, at least 95%, or sometimes all of these highly conserved amino acids at positions corresponding to the highly conserved amino acids identified in SEQ ID NO: 23. For example, SEQ ID NO: 4 (LlKIVD) contains 95% of these highly conserved amino acids at positions corresponding to their referenced positions in SEQ ID NO: 23. SEQ ID NO: 4 is a suitable OADC for use in accordance with the methods of the present disclosure. In some embodiments, each of these highly conserved amino acids are found in a desired OADC enzyme, as provided in SEQ ID NO: 23.

Isobutyraldehyde Dehydrogenase

Isobutyraldehyde dehydrogenase (IBADH) (EC 1.2.1.5) described herein catalyzes the conversion of isobutyraldehyde, water and $NAD(P)^+$ to isobutyric acid and $NAD(P)H$ (Table 1).

Generally, IBADH enzymes are known to utilize the cofactor NADP; $NADP^+$ is reduced to NADPH during catalysis. As with the above described KARI enzymes, in some organisms, dependence on NADP as a cofactor can hamper isobutyraldehyde dehydrogenase turnover and thus isobutyric acid titers, yields and/or productivities during fermentation. Using standard microbial engineering techniques, enzyme cofactor specificity can be modified and recombinant host cells can be designed to express isobutyraldehyde dehydrogenase with altered cofactor specificity. IBADH enzymes of the present disclosure may include: 1) IBADH enzymes that bind and reduce $NAD^+$; 2) IBADH enzymes that bind and reduce $NADP^+$; and/or 3) IBADH enzymes that can indiscriminately bind and reduce $NAD^+$ and $NADP^+$. In some embodiments of the present disclosure, recombinant host cells may contain an IBADH enzyme that utilizes NADH as a cofactor and is capable of producing isobutyric acid. In some embodiments, recombinant host cells may contain an IBADH enzyme that utilizes NADPH as a cofactor and is capable of producing isobutyric acid. In some embodiments, recombinant host cells may contain an IBADH enzyme that utilizes NADH and/or NADPH as a cofactor and is capable of producing isobutyric acid.

Any enzyme is suitable for use in accordance with the disclosed method so long as the enzyme is capable of catalyzing the conversion of isobutyraldehyde to isobutyric acid with concomitant reduction of NAD(P) to NAD(P)H. In some embodiments, the IBADH may be derived from a bacterial source. In many of these embodiments, the IBADH is derived from a host cell belonging to a genus selected from the group including *Enterobacter, Escherichia, Gluconobacter, Klebsiella, Pseudomonas, Serratia,* and *Sphingobium*. In one embodiment, the IBADH is derived from *Escherichia coli*.

Non-limiting examples of IBADH include those derived from *Enterobacter asburiae* (UniProt ID: G2S1W8), *Enterobacter lignolyticus* (UniProt ID: E3G8V6), *Enterobacteriaceae bacterium* (UniProt ID: L0M324), *Escherichia coli* (UniProt ID: P80668), *Gluconobacter thailandicus* (UniProt ID: M9MLV8), *Klebsiella pneumoniae* (UniProt ID: A6T8G6), *Pseudomonas* sp. (UniProt ID: I4MZX3), *Serratia marcescens* (UniProt ID: L0MER4), and/or *Sphingobium chlorophenolicum* (UniProt ID: F6EWX4).

In a particular embodiment, the IBADH is the *E. coli* FeaB protein (abbv. EcFEAB; UniProt ID P80668; SEQ ID NO: 5).

In an embodiment of the present disclosure, recombinant host cells may include one or more heterologous nucleic acids encoding IBADH wherein the recombinant host cells are capable of producing isobutyric acid. In another embodiment, recombinant host cells may include one or more heterologous nucleic acids encoding a protein with IBADH activity wherein the recombinant host cells are capable of producing isobutyric acid. In various embodiments, proteins suitable for use in accordance with methods of the present disclosure have IBADH activity and may contain an amino acid sequence with at least 60%, at least 70%, at least 80%, at least 90%, or at least 95% sequence identity to SEQ ID NO: 5. In many embodiments, the recombinant host cell is a *P. kudriavzevii* strain.

SEQ ID NO: 24 represents an IBADH Consensus Sequence #1 which was constructed based on the isobutyraldehyde dehydrogenase sequences from *Enterobacter asburiae* (UniProt ID: G2S1W8), *Enterobacter lignolyticus* (UniProt ID: E3G8V6), *Enterobacteriaceae bacterium* (UniProt ID: L0M324), *Escherichia coli* (UniProt ID: P80668), *Gluconobacter thailandicus* (UniProt ID: M9MLV8), *Klebsiella pneumoniae* (UniProt ID: A6T8G6), *Pseudomonas* sp. (UniProt ID: I4MZX3), *Serratia marcescens* (UniProt ID: L0MER4), and *Sphingobium chlorophenolicum* (UniProt ID: F6EWX4).

In various embodiments, IBADH enzymes suitable for use in accordance with the methods of the present disclosure may have IBADH activity and contain an amino acid sequence with at least 60%, at least 65%, or at least 70% sequence identity to SEQ ID NO: 24. For example, the EcFEAB (SEQ ID NO: 5) sequence is 92% identical to consensus sequence SEQ ID NO: 24.

Many amino acids in SEQ ID NO: 24 are highly conserved and IBADH enzymes suitable for use in accordance with the methods of the present disclosure may include many of these highly conserved amino acids at positions aligning with the location of the indicated amino acid in SEQ ID NO: 24. In certain cases, a substantial number of these highly conserved amino acids will align, in others, all of these highly conserved amino acids will align. The highly conserved amino acids in SEQ ID NO: 24 are F15, L16, R18, L22, G26, L37, P42, G45, I48, A52, D53, A54, D58, V59, A62, V63, S65, F70, W75, P80, A81, R83, E84, R85, L87, L88, R89, D92, L93, E95, E99, A102, Q103, L104, E105, L107, E108, Q109, G110, 5112, I113, R117, E120, V121, W127, R129, Y130, A132, G133, L134, T136, K137, G140, T142, D144, 5146, T159, E162, P163, G165, V166, V167, A168, P172, W173, N174, F175, P176, L177, I179, W182, K183, V184, P186, A187, L188, A189, G191, C192, S193, K197, P198, S199, E200, T202, P203, L204, T205, E211, A213, A216, G217, P219, G221, V222, F223, N224, T227, G228, G230, G234, L237, H240, P241, K245, S247, F248, T249, G250, S251, T252, G255, K256, I258, L271, E272, L273, G274, G275, K276, N277, P278, A279, L282, D284, A285, V290, G293, L294, F299, N301, G303, Q304, V305, C306, A307, A308, S310, R311, I312, Y313, E315, P317, D320, A329, G336, P337, G338, N346, P347, S350, H353, K356, L361, A364, A369, G374, P378, G382, Y384, P387, L389, N392, L399, R401, E403, V404, F405, G406, P407, V408, R413, V414, E418, L421, A424, N425, G430, L431, A433, S434, W436, T437, A443, A452, G453, T454, W456, V457, N458, H460, I463, D464, N466, P468, F469, G470, G471, K473, S475, G476, G478, R479, D480, F481, G482, W485, L486, D487, E491, K493, S494, and C496. In various embodiments, IBADH enzymes suitable for use in accordance with the methods of the present disclosure homologous to SEQ ID NO: 24 contain at least 60%, at least 70%, at least 80%, at least 85%, at least 90%, at least 95%, or sometimes all of these highly conserved amino acids at positions corresponding to the highly conserved amino acids identified in SEQ ID NO: 24. For example, SEQ ID NO: 5 (EcFEAB) includes 95% of these highly conserved amino acids at positions corresponding to their referenced positions in SEQ ID NO: 24. SEQ ID NO: 5 is a suitable IBADH for use in accordance with the methods of the present disclosure. In some embodiments, each of these highly conserved amino acids are found in a desired IBADH enzyme, as provided in SEQ ID NO: 24.

Mitochondrial Isobutyic Acid Pathway Expression

The isobutyric acid pathway enzyme dihydroxyacid dehydratase (DHAD) uses a Fe—S cluster as a cofactor to catalyze a dehydration reaction. In eukaryotes, the Fe—S cluster biogenesis takes place in the mitochondria and most of the native Fe—S enzyme activity takes place in the mitochondria; while enzymes requiring the Fe—S cofactor are found in the yeast cytosol they are relatively rare. Yeast produces branched-chain amino acids (leucine, valine and isoleucine) using a mitochondrial pathway comprising the first three steps of the isobutyric acid pathway, namely acetolactate synthase (ILV2), ketol-acid reductoisomerase (ILV5), and the Fe—S utilizing enzyme dihydroxyacid dehydratase (ILV3). Thus, through the activity of these three enzymes yeast synthesize the isobutyric acid pathway intermediate 3-methyl-2-oxobutanoate. Expression of the isobutyric acid pathway enzymes in the yeast mitochondria can therefore take advantage of the higher occurrence of Fe—S cofactor in the mitochondria as compared to the cytosol, leading to higher DHAD activity and isobutyric acid production.

In some embodiments, the isobutyric acid pathway enzymes are expressed in the host cell cytosol resulting in isobutyric acid production. In other embodiments, the isobutyric acid pathway enzymes are expressed in the host cell mitochondria and result in isobutyric acid production. Those skilled in the art recognize that cytosolic proteins can be re-localized to the mitochondria when expressed in eukaryotic host cells (like yeast) by including an N-terminal mitochondrial targeting sequence. Various algorithms are readily available to identify suitable mitochondrial targeting sequences (see, for example, Fukasawa Y, et al., "MitoFates: improved prediction of mitochondrial targeting sequences and their cleavage sites." Molecular and Cellular Proteomics 14(4): 1113-1126 (2015)). One such mitochondrial targeting sequence in *P. kudriavzevii* is the 30 N-terminal amino acids of the mitochondrial pyruvate dehydrogenase complex protein PDA1 (UniProt ID: A0A099P5A5). As described in Example 10, expression of a mitochondrial isobutyric acid pathway comprising the same isobutyric acid pathway proteins expressed in the host cell cytosol, except with addition of a *P. kudriavzevii* PDA1 mitochondrial targeting sequence at each protein's N-terminus, resulted in isobutyric acid production.

Ancillary Proteins

Ancillary proteins are other proteins that are expressed in recombinant host cells of the present disclosure whose expression results in an increase in isobutyric acid yields, productivities, and/or titers as compared to control, or host cells that do not express the proteins. Ancillary proteins function outside the isobutyric acid pathway, wherein each ancillary protein plays a role that increases the recombinant host cell's ability to produce isobutyric acid. Ancillary proteins may include any protein (excluding isobutyric acid pathway enzymes) of any structure or function that can increase isobutyric acid yields, titers, or productivities when expressed. Non-limiting examples of classes of ancillary proteins include transcription factors, transporters, scaffold proteins, proteins that decrease byproduct accumulation, and proteins that regenerate or synthesize redox cofactors. Ancillary proteins may be either native or non-native proteins. In cases where the protein is a native protein it is expressed in a non-native context, for example, it may be expressed from a heterologous nucleic acid.

Provided herein in certain embodiments are recombinant host cells containing one or more heterologous nucleic acids encoding one or more ancillary proteins wherein the recombinant host cell is capable of producing higher isobutyric acid yields, titers, or productivities as compared to control cells, or host cells that do not contain the heterologous nucleic acid(s).

In some embodiments, that host recombinant cell naturally produces isobutyric acid and in these cases, the isobutyric acid yields, titers, and/or productivities are increased following expression of one or more ancillary proteins. In other embodiments, the recombinant host cell does not natively produce isobutyric acid and has been engineered to produce isobutyric acid. In certain embodiments of the present disclosure, the recombinant host cells contain one or more heterologous nucleic acids encoding one or more isobutyric acid pathway enzymes and one or more heterologous nucleic acids encoding one or more ancillary proteins. In certain of these embodiments, the recombinant host cells may be engineered to express more of these ancillary proteins. In these particular embodiments, the ancillary proteins are expressed at a higher level (i.e., produced at a higher amount as compared to cells that do not express the ancillary proteins) and may be operatively linked to one or more exogenous promoters or other regulatory elements.

In certain embodiments, recombinant host cells contain both endogenous and heterologous nucleic acids encoding one or more isobutyric acid pathway enzymes and one or more ancillary proteins. In certain embodiments, the recombinant host cells contain one or more heterologous nucleic acids encoding one or more isobutyric acid pathway enzymes and/or one or more ancillary proteins, and one or more endogenous nucleic acids encoding one or more isobutyric acid pathway enzymes and/or one or more ancillary proteins.

In certain embodiments, endogenous nucleic acids of ancillary proteins may be modified in situ (i.e., on chromosome in the host cell genome) to alter levels of expression, activity, or specificity. In some embodiments, heterologous nucleic acids may be inserted into endogenous nucleic acids of ancillary proteins.

Ancillary Proteins: Redox Cofactor Recycling

One category of ancillary proteins which may be used are proteins that recycle the redox cofactors produced during isobutyric acid pathway activity. Redox balance is fundamental to sustained metabolism and cellular growth in living organisms. Intracellular redox potential is determined by redox cofactors that facilitate the transfer of electrons from one molecule to another within a cell. Yeast-derived redox cofactors which may be used as ancillary proteins in the disclosed methods include the nicotinamide adenine dinucleotides, NAD and NADP, the flavin nucleotides, FAD and FMN, and iron sulfur clusters (Fe—S clusters). Redox cofactors may also be derived from other eukaryotic cells or derived from prokaryotic cells.

Redox constraints play an important role in end-product formation. Additional reducing power must be provided to produce compounds whose degree of reduction is higher than that of the substrate. Conversely, in the absence of oxygen as a terminal electron acceptor, producing compounds with a degree of reduction lower than that of the substrate will force the synthesis of byproducts with higher degrees of reduction to compensate for excess reducing power generated from substrate oxidation. Re-oxidation of NAD(P)H to NAD(P)$^+$ is important for maintaining the thermodynamic driving force necessary for efficient and rapid isobutyric acid production and thus it is important to maintain redox neutrality to ensure efficient end-product formation. For example, the isobutyric acid pathway results in a net formation of 2 mol of NAD(P)H for each mol of isobutyric acid produced in the cytosol. In the absence of sufficient oxygen and/or electron transport chain flux, overflow metabolism (for example, in the yeast cytosol) can occur to reoxidize surplus cytosolic NAD(P)H, leading to byproduct accumulation and decreasing product titers, yields and/or productivities. Ancillary proteins can be expressed to reoxidize excess NAD(P)H without driving the formation of unwanted byproducts. Non-limiting examples of ancillary proteins that can be overexpressed to restore this redox balance include NADH dehydrogenase and water-forming NADH oxidase. In certain embodiments, the ancillary proteins may be expressed in the cytosol of recombinant host cells. In certain embodiments, the ancillary proteins may be associated with the mitochondrial or cell membrane of the recombinant host cells.

In many embodiments of the present disclosure, recombinant host cells capable of producing isobutyric acid may contain one or more nucleic acids encoding a NADH dehydrogenase ancillary protein. In some embodiments, the one or more nucleic acids are endogenous nucleic acids encoding a NADH dehydrogenase. In other embodiments, the one or more nucleic acids are heterologous nucleic acids encoding a NADH dehydrogenase. The yeast NADH dehydrogenase catalyzes the oxidation of NAD(P)H to NAD(P)$^+$, thereby shuttling electrons from cytosolic NAD(P)H into the mitochondrial electron transport chain. Any NAD(P)H dehydrogenase can be used in accordance with the disclosed methods so long as it is capable of oxidizing NAD(P)H to NAD(P)$^+$ in the cytosol. In many embodiments, the NADH dehydrogenase ancillary protein is expressed in the cytosol. In some embodiments, the NADH dehydrogenase is membrane associated or membrane bound. In some embodiments, the NADH dehydrogenase is a mitochondrial external NADH dehydrogenase. In yeast, the mitochondrial external NADH dehydrogenase is an inner-membrane mitochondrial protein with its catalytic site facing the intermembrane space. Because the mitochondrial outer membrane is permeable to most small molecules, the mitochondrial intermembrane space is considered to have the same environment as the cytosol. Therefore, the mitochondrial external NADH dehydrogenase contributes to the oxidation of cytosolic NAD(P)H and is a suitable ancillary protein for isobutyric acid production. In some embodiments, the mitochondrial external NADH dehydrogenase is the *P. kudriavzevii* NdeI protein (abbv. PkNDE1; SEQ ID: NO 6). In some embodiments, recombinant host cells may contain one or more heterologous nucleic acids encoding one or more proteins suitable for use in accordance with methods of the present disclosure having NAD(P)H dehydrogenase activity and may further contain an amino acid sequence with at least 60%, at least 70%, at least 80%, at least 90%, or at least 95% sequence identity to SEQ ID NO: 6.

In some embodiments, recombinant host cells may contain one or more heterologous and/or endogenous nucleic acids encoding a water-forming NADH oxidase ancillary protein. The NADH oxidase converts NAD(P)H to NAD(P)$^+$ and can restore redox balance in the host cell cytosol while reducing molecular oxygen, resulting in the formation of one mol water per mol NADH. Any NAD(P)H oxidase can be used in accordance with the disclosed methods so long as it is capable of oxidizing NAD(P)H to NAD(P)+ and reducing molecular oxygen to water in the cytosol.

In some embodiments, the water-forming NADH oxidase may be derived from a bacterial source. In many of these embodiments, the bacterial water-forming NADH oxidase is a *Lactococcus lactis* NoxE protein (abbv. LlNOXE; UniProt ID A2RIB7; SEQ ID: NO 7). In some embodiments, recombinant host cells may contain one or more heterologous nucleic acids encoding one or more proteins suitable for use in accordance with methods of the present disclosure have water-forming NAD(P)H oxidase activity and may contain an amino acid sequence with at least 60%, at least 70%, at least 80%, at least 90%, or at least 95% sequence identity to SEQ ID NO: 7.

In addition to being found in many bacteria, the water-forming NADH oxidases are also found in a number of archaeal microbes and in some embodiments, the NADH oxidase is derived from an archaeal source.

Ancillary Proteins: Redox Cofactor Biogenesis

As explained in preceding paragraphs, redox balance is crucial for cell growth and sustained metabolism. Three out of the five isobutyric acid pathway enzymes detailed in Table 1 utilize redox cofactors that must be generated, in addition to being recycled, for robust metabolism and cell vitality. In some embodiments of the present disclosure, recombinant host cells may contain EcILVC that utilizes NAD(P)H. In some embodiments, recombinant host cells may contain LlILVD that utilizes Fe—S clusters. In some embodiments, recombinant host cells may contain EcFEAB that utilizes NAD(P). Thus, biogenesis and homeostasis of these cofactors are crucial for efficient catalysis of these enzymatic reactions.

Fe—S clusters facilitate various enzyme activities that require electron transfer. Because both iron and sulfur atoms are highly reactive and toxic to cells, Fe—S cluster assembly requires carefully coordinated synthetic pathways in living cells. The three known pathways are the Isc (iron sulfur cluster) system, the Suf (sulfur formation) system, and the Nif (nitrogen fixation) system. Each of these systems has a unique physiological role, yet several functional components are shared between them. First, a cysteine desulfurase enzyme liberates sulfur atoms from free cysteine. Then, a scaffold protein receives the liberated sulfur for Fe—S cluster assembly. Finally, the Fe—S cluster is transferred to a target apoprotein. In some embodiments of the present disclosure, recombinant host cells may contain heterologous and/or endogenous nucleic acids encoding one or more ancillary proteins that facilitate Fe—S cluster assembly. In some embodiments, the ancillary proteins may include one, more or all proteins of the Isc system, the Suf system, the Nif system, or any combination thereof. In some embodiments, recombinant host cells may contain one or more heterologous nucleic acids encoding one or more proteins suitable for use in accordance with methods of the present disclosure having cysteine desulfurase activity, Fe—S cluster assembly capability, Fe—S cluster transfer capability, iron chaperone capability, or any combination thereof.

Similar to Fe—S clusters, the NAD and NADP cofactors are involved in electron transfer and contribute to approximately 12% of all biochemical reactions in a cell (Osterman A., EcoSal Plus, 2009). NAD is assembled from L-aspartate, dihydroxyacetone phosphate (DHAP), phosphoribosyl pyrophosphate (PRPP) and ATP. The NADP is assembled in the same manner and further phosphorylated. In some embodiments, recombinant host cells may contain heterologous and/or endogenous nucleic acids encoding one or more ancillary proteins that facilitate NAD and NADP cofactor assembly. In some embodiments, the ancillary proteins may contain one, more or all proteins suitable for use in accordance with methods of the present disclosure having NAD and/or NADP assembly capability, NAD and/or NADP transfer capability, NAD and/or NADP chaperone capability, or any combination thereof.

Ancillary Proteins: Isobutyric Acid Transport

Another class of ancillary proteins useful for increasing isobutyric acid yields, titers, and/or productivities are isobutyric acid transporter proteins. In some embodiments, recombinant host cells may contain one or more heterologous and/or endogenous nucleic acids encoding one or more isobutyric acid transporter proteins. In many embodiments, the isobutyric acid transporter is derived from a fungal source. In some embodiments, the isobutyric acid transporter may include those derived from *S. cerevisiae* PDR12 (abbv. ScPDR12; UniProt ID: Q02785), *S. cerevisiae* WAR1 (abbv. ScWAR1; UniProt ID: Q03631), and/or *Kluyveromyces marxianus* PDC12 (abbv. KmPDC12; UniProt ID: W0T9C6). In some embodiments, recombinant host cells may contain one or more heterologous nucleic acids encoding one or more proteins suitable for use in accordance with methods of the present disclosure have isobutyric acid transporter activity and may contain an amino acid sequence with at least 60%, at least 70%, at least 80%, at least 90%, or at least 95% sequence identity to ScPDR12, ScWAR1, and/or KmPDC12.

Decreasing or Eliminating Expression of Byproduct Pathway Enzymes

In an additional aspect of this disclosure, nucleic acids encoding byproduct pathway enzymes may be disrupted in the recombinant host cells of the present disclosure to increase isobutyric acid yields, productivities, and/or titers; and/or to decrease byproduct titers and/or yields as compared to control cells, or host cells that express native/undisrupted levels of the byproduct pathway enzymes. Byproduct pathway enzymes may include any protein (excluding isobutyric acid pathway enzymes) of any structure or function that can decrease isobutyric acid yields, titers, or productivities when undisrupted because they utilize intermediates or products of the isobutyric acid pathway.

Byproducts that accumulate during isobutyric acid production and can lead to: 1) lower isobutyric acid titers, productivities and/or yields; and/or 2) accumulation of byproducts in the fermentation broth that increase the difficulty of downstream purification processes. In some embodiments, recombinant host cells may contain genetic disruptions that encompass alterations, deletions, substitutions, promoter modifications, premature stop codons and knock-outs, or knock-downs that decrease byproduct accumulation. In some embodiments, recombinant host cells containing a disruption of one or more genes encoding a byproduct pathway enzyme will have altered performance characteristics as compared to cells without the genetic disruption(s), such as decreased or eliminated byproduct pathway enzyme expression, decreased or eliminated byproduct accumulation, improved isobutyric acid pathway activity, altered metabolite flux through the isobutyric acid pathway, higher isobutyric acid titers, higher isobutyric acid productivities, higher isobutyric acid yields, and/or altered cellular fitness.

One important reason to decrease byproduct formation is that it allows an increase in isobutyric acid pathway activity, resulting in increased isobutyric acid production. In many embodiments, recombinant host cells of the present disclosure containing one or more genetic disruptions of one or more genes encoding a byproduct pathway enzyme may produce an increased isobutyric acid titer as compared to host cells that do not contain the genetic disruption(s). In some of these embodiments, the isobutyric acid titer in the fermentation broth is increased by 0.5 g/l, 1 g/l, 2.5 g/l, 5 g/l, 7.5 g/l, 10 g/l, or more than 10 g/l.

In addition to increasing isobutyric acid titers, decreasing byproduct formation can also help increase isobutyric acid yields. Because yield is independent of the volume of the fermentation broth, which can change during the course of a fermentation, it is often advantageous to measure isobutyric acid yields. In many embodiments, recombinant host cells of the present disclosure containing one or more genetic disruptions of one or more genes encoding byproduct pathway enzymes may produce an increased isobutyric acid yield as compared to host cells that do not contain the genetic disruption. In some of these embodiments, the isobutyric acid yield is increased by 0.5%, 1%, 2.5%, 5%, 7.5%, 10%, or more than 10% (g-isobutyric acid/g-substrate). The substrate in this yield calculation is the fermentation substrate, which is typically glucose, but may also be other, non-glucose substrates (e.g., sucrose, glycerol, or pyruvate).

Increasing isobutyric acid production is important for decreasing manufacturing costs, but it is also useful to disrupt genes encoding byproduct pathway enzymes in order to decrease byproduct formation. Byproducts are typically unwanted chemicals, are disposed of as waste, and their disposal can involve elaborate processing steps and containment requirements. Therefore, decreasing byproduct formation is generally also important for lowering production costs. In many embodiments, recombinant host cells of the present disclosure contain one or more genetic disruptions of one or more genes encoding a byproduct pathway enzyme may produce a lower byproduct titer as compared to host cells that do not contain the genetic disruption. In some of these embodiments, a recombinant host cell of the disclosure that contains genetic disruption of one or more byproduct pathway enzymes produces a byproduct titer that is 0.5 g/l, 1 g/l, 2.5 g/l, 5 g/l, 7.5 g/l, 10 g/l, or more than 10 g/l less than host cells that do not contain the genetic disruption.

In many embodiments, recombinant host cells of the present disclosure containing one or more genetic disruptions of one or more genes encoding a byproduct pathway enzyme produce a lower byproduct yield as compared to host cells that do not contain the genetic disruption(s). In some of these embodiments, recombinant host cells contain genetic disruption of one or more genes encoding byproduct pathway enzymes produce a byproduct yield that is 0.5%, 1%, 2.5%, 5%, 7.5%, 10%, or more than 10% (g-byproduct/g-substrate) less than host cells that do not contain the genetic disruption. As with the isobutyric acid yield calculation, the substrate used in the byproduct yield calculation is the carbon source provided to the fermentation; this is typically glucose, sucrose, or glycerol, but may be any carbon substrate.

Non-limiting examples of byproducts that arise due to consumption of an isobutyric acid pathway substrate, intermediate or product, include isobutanol, acetaldehyde, glycerone, carbon dioxide, acetaldehyde, acetoin, acetate, glycerol, and ethanol. In the event of a redox imbalance, an undesirable excess of reduced or oxidized cofactors may also accumulate; thus, the redox cofactors NADH, $NAD^+$, NADPH and $NADP^+$ can also be considered byproducts.

A non-limiting list of enzyme-catalyzed reactions that utilize the isobutyric acid pathway substrate (i.e., pyruvate), an isobutyric acid pathway intermediate, or isobutyric acid itself, are found in Table 2. Decreasing or eliminating expression of one, some or all of the genes encoding the enzymes in Table 2 can increase isobutyric acid production and/or decrease byproduct production. In many cases, the product of the enzyme-catalyzed reactions provided in Table 2 can accumulate in the fermentation broth; in such cases, this indicates that expression of the native gene encoding the listed enzyme should be reduced or eliminated. For example, the occurrence of dihydroxyacetone (also known as glycerone) in the fermentation broth indicates that expression of a native gene encoding glycerol dehydrogenase should be decreased or eliminated. In some cases, the product of the specific reaction listed in Table 2 is further converted, either spontaneously or through the action of other enzymes, into a byproduct that accumulates in the fermentation broth. For example, dihydroxyacetone is generally metabolized to glycerol, which is found to accumulate in the fermentation broth. In cases where byproduct accumulation is due to the activity of multiple enzymes, one or more of the genes encoding the one or more byproduct pathway enzymes can be deleted or disrupted to reduce byproduct formation.

In some embodiments of the present disclosure, recombinant host cells may be microbial strains with decreased or eliminated expression of one, some or all of the genes encoding enzymes listed in Table 2. In some embodiments, recombinant host cells may be microbial strains with decreased byproduct accumulation wherein the byproducts are formed through the activity of one, some or all of the enzymes listed in Table 2. In some embodiments, recombinant host cells may be microbial strains with decreased expression of pyruvate-utilizing enzymes. In some embodiments, recombinant host cells may be microbial strains with decreased expression of isobutyric acid-utilizing enzymes. In some embodiments, recombinant host cells may be microbial strains with inability to catabolize or breakdown isobutyric acid. In some embodiments, recombinant host cells may contain genetic modifications that reduce the ability of the host cells to catabolize the isobutyric acid pathway intermediates except via the isobutyric acid pathway. In some embodiments, recombinant host cells may contain genetic modifications that decrease the ability of the host cells to catabolize pyruvate except via the isobutyric acid pathway.

accumulation of pyruvate decarboxylase-based byproducts. As described above, homologous proteins share substantial sequence identity with each other. Any protein that is homologous to any of the pyruvate decarboxylases of the present disclosure (SEQ ID NOs: 8, 9 and 10) will share substantial sequence identity one or more of these proteins.

In some embodiments, recombinant host cells may contain genetic disruptions in one or more pyruvate decarboxylase homologs. As defined above, genetic disruptions encompass nucleic acid deletions, nucleic acid insertions, nucleic acid substitutions, nucleic acid mutations, premature stop codons and promoter modifications. In some embodiments, recombinant host cells of the present disclosure may contain a genetic disruption of a homologous pyruvate decarboxylase gene with at least 60%, at least 70%, at least 80%, at least 90%, at least 95%, or more than 95% homology when compared to PkPDC1, PkPDC5 or PkPDC6. In some of these embodiments, the recombinant host cell is a

TABLE 2

Enzyme-catalyzed Reactions that Consume Isobutyric Acid Pathway Substrate, Intermediate or Product

| Substrate | EC # | Enzyme name | Reaction formula |
|---|---|---|---|
| Isobutyrate | 6.2.1.1 | Isobutanoate/CoA-ligase | Isobutyrate + CoA + ATP → Isobutyryl-CoA + AMP + Diphosphate |
| Acetaldehyde | 1.2.1.3 | Acetaldehyde dehydrogenase | Acetaldehyde + Oxidized cofactor + $H_2O$ → Acetate + Reduced cofactor + $H^+$ |
| Aldehyde | 1.1.1.1 | Alcohol dehydrogenase | Aldehyde + Reduced cofactor → Alcohol + Oxidized cofactor |
| Isobutyraldehyde | 1.1.1.1 | Isobutyraldehyde reductase | Isobutyraldehyde + Reduced cofactor → Isobutanol + Oxidized cofactor |
| 2-Acetolactate | 4.1.1.5 | Acetolactate decarboxylase | 2-Acetolactate → Acetoin + $CO_2$ |
| Pyruvate | 1.1.1.28 | Lactate dehydrogenase | Pyruvate + Reduced cofactor + $H^+$ ⇌ Lactate + Oxidized cofactor |
| Pyruvate | 4.1.1.1 | Pyruvate decarboxylase | Pyruvate + $H^+$ → Acetaldehyde + $CO_2$ |
| Pyruvate | n/a | Pyruvate dehydrogenase complex | Pyruvate + CoA + Oxidized cofactor → Acetyl-CoA + $CO_2$ + Reduced cofactor |
| Pyruvate | 6.4.1.1 | Pyruvate carboxylase | Pyruvate + $HCO_3^-$ + ATP → Oxaloacetate + ADP + Phosphate + $H^+$ |

Decreasing or Eliminating Expression of Pyruvate Decarboxylase

Pyruvate decarboxylase catalyzes the conversion of pyruvate to acetaldehyde and $CO_2$. This reaction is irreversible/unidirectional and, under most conditions, is thermodynamically favored over the acetolactate synthase catalyzed reaction (step 1 of the isobutyric acid pathway detailed in FIG. 1); the difference in equilibrium constant between acetolactate synthase and pyruvate decarboxylase, at 1 mM metabolite concentrations, i.e., $\Delta Keq'm$, is $-8.97 \times 10^5$ kJ/mol. Thus, under the calculated conditions of a recombinant host cell, pyruvate decarboxylase activity is favored (i.e., a negative $\Delta Keq'^m$) over acetolactate synthase. Pyruvate decarboxylase activity can lead to the formation of at least three undesirable pyruvate decarboxylase-based byproducts: acetaldehyde, acetate, and ethanol. There are at least 3 pyruvate decarboxylase homologs in *P. kudriavzevii*: PkPDC1 (SEQ ID NO: 8), PkPDC5 (SEQ ID NO: 9) and PkPDC6 (SEQ ID NO: 10); decreasing or eliminating expression of one or more of these homologs is useful for increasing isobutyric acid production and/or decreasing

*P. kudriavzevii* strain. In some embodiments, recombinant host cells may contain one or more gene disruptions that produce altered, decreased or eliminated activity in one, two or all three, pyruvate decarboxylase proteins. In some of these other embodiments, the recombinant host cell is a *P. kudriavzevii* strain.

In some embodiments, recombinant host cells may contain heterologous nucleic acids encoding isobutyric pathway enzymes, and may further contain one or more genetic disruptions of one, more, or all of the pyruvate decarboxylase homologs. In certain embodiments, acetaldehyde byproduct titer (i.e., g of byproduct/liter of fermentation volume) at the end of fermentation is 10 g/l or less, preferably 5 g/l or less, and most preferably 2.5 g/l or less. In certain embodiments, acetaldehyde byproduct yield (i.e., percentage of g of byproduct/g of substrate) at the end of fermentation is 10% or less, 5% or less, 2.5% or less, and preferably, 1% or less. In certain embodiments, acetate byproduct titer at the end of fermentation is 10 g/l or less, preferably 5 g/l or less, and most preferably 2.5 g/l or less. In certain embodiments, acetate byproduct yield at the end of fermentation is 10% or less, 5% or less, 2.5% or less, and preferably, 1% or less. In some embodiments, ethanol byproduct titer at the end of a fermentation is 10 g/l or less, preferably 5 g/l or less, and most preferably 2.5 g/l or less. In certain embodiments, ethanol byproduct yield at the end of fermentation is 10% or less, 5% or less, 2.5% or less, and preferably, 1% or less.

Decreasing or Eliminating Expression of Pyruvate Dehydrogenase

The pyruvate dehydrogenase complex catalyzes the conversion of pyruvate, coenzyme A and $NAD^+$ to acetyl-CoA, $CO_2$ and NADH; in wild type $P.$ $kudriavzevii$, this enzyme is localized in the mitochondria. This reaction is irreversible/unidirectional and is thermodynamically favored over the acetolactate synthase (ALS) catalyzed reaction (step 1 of the isobutyric acid pathway); the $\Delta Keq'''$ between ALS and pyruvate dehydrogenase complex is $-8.48 \times 10^5$ kJ/mol. Thus, pyruvate dehydrogenase complex activity is favored (i.e., a negative $\Delta Keq'''$) over ALS activity. In most native microbes, pyruvate dehydrogenase is used for aerobic metabolism of pyruvate to $CO_2$ through the activity of the tricarboxylic acid cycle enzymes. Genetic disruption of one or more genes encoding a protein of the pyruvate dehydrogenase complex can decrease pyruvate dehydrogenase complex protein activity or expression, consequently increasing isobutyric acid production and/or decreasing $CO_2$ byproduct formation. In some embodiments of the present disclosure, recombinant host cells may contain decreased or eliminated expression and/or activity of one or more pyruvate dehydrogenase complex proteins. In some of these embodiments, recombinant host cells may contain decreased or eliminated expression and/or activity of the E1 α-subunit of the pyruvate dehydrogenase complex (abbv. PkPDA1; SEQ ID NO: 11). In some embodiments, the recombinant host cell is a $P.$ $kudriavzevii$ strain.

Decreasing or Eliminating Expression of Alcohol Dehydrogenase Enzymes

Alcohol dehydrogenase catalyzes the conversion of aldehyde and NAD(P)H to alcohol byproduct and $NAD(P)^+$. Although many alcohol dehydrogenases are known to have high substrate specificity (e.g., are specific for the reduction of isobutyraldehyde to isobutanol), many others are substrate promiscuous and may reduce many different aldehyde substrates.

Multiple protein homologs with alcohol dehydrogenase activity may be present in a recombinant host cell. It may be necessary to genetically disrupt one or more alcohol dehydrogenase homologs to increase isobutyric acid pathway activity and/or decrease alcohol byproduct accumulation. In some embodiments of the present disclosure, recombinant host cells may contain heterologous nucleic acids encoding the isobutyric acid pathway enzymes and may further contain genetic disruptions of one or more alcohol dehydrogenase homologs. In some of these embodiments, the genetic disruptions give rise to decreased, altered or eliminated expression of one or more alcohol dehydrogenase homologs, and/or decreased, altered or eliminated activity of one or more alcohol dehydrogenase homologs.

In $P.$ $kudriavzevii$, two alcohol dehydrogenase enzymes are the Adh1 protein (abbv. PkADH1; SEQ ID NO: 13) and the Adh6A protein (abbv. PkADH6A; SEQ ID NO: 14). In many embodiments, wherein the recombinant host cell is a $P.$ $kudriavzevii$ strain, recombinant host cells may contain genetic disruptions that give rise to decreased, altered or eliminated expression and/or activity of PkADH1 and/or PkADH6.

In some embodiments, recombinant host cells of the present disclosure may contain one or more genetic disruptions in one or more alcohol dehydrogenase homologs with at least 60%, at least 70%, at least 80%, at least 90%, at least 95%, or more than 95% homology when compared to PkADH1 and/or PkADH6A.

In some embodiments, recombinant host cells may contain heterologous nucleic acids encoding isobutyric pathway enzymes and may further contain one or more genetic disruptions of one or more alcohol dehydrogenase homologs. In certain embodiments, ethanol byproduct titer at the end of the fermentation is 10 g/l or less, preferably 5 g/l or less, and most preferably 2.5 g/l or less. In other embodiments, isobutanol byproduct yield at the end of fermentation is 10% or less, 5% or less, 2.5% or less, and preferably, 1% of less.

Decreasing or Eliminating Expression of Acetaldehyde Dehydrogenase

Acetaldehyde dehydrogenase catalyzes the conversion of acetaldehyde, $NAD(P)^+$ and water to acetate byproduct and NAD(P)H. Although many aldehyde dehydrogenases bind to a specific aldehyde substrate (such as acetaldehyde), many others are capable of binding indiscriminately to a variety of aldehyde substrates. In $P.$ $kudriavzevii$, the acetaldehyde dehydrogenase proteins include the Ald2a protein (abbv. PkALD2A; SEQ ID NO: 15), the Ald2b protein (abbv. PkALD2B; SEQ ID NO: 16), the Ald3 protein (abbv. PkALD3; SEQ ID NO: 17), and the Ald6 protein (abbv. PkALD6; SEQ ID NO: 18). In some embodiments of the present disclosure, nucleic acids encoding PkALD2A, PkALD2B, PkALD3 or PkALD6, or any combination thereof, are genetically disrupted.

In embodiments of the present disclosure where in the recombinant host cell is a $P.$ $kudriavzevii$ strain, recombinant host cells may contain genetic disruptions that give rise to decreased, altered or eliminated expression or activity of PkALD2A, PkALD2B, PkALD3 or PkALD6, or any combination thereof. In some embodiments, recombinant host cells of the present disclosure may contain one or more genetic disruptions in one or more aldehyde dehydrogenase homologs with at least 60%, at least 70%, at least 80%, at least 90%, at least 95%, or more than 95% homology when compared PkALD2A, PkALD2B, PkALD3 or PkALD6.

In some embodiments, recombinant host cells may contain heterologous nucleic acids encoding isobutyric pathway enzymes, and may further contain one or more genetic disruptions of one, more, or all of the acetaldehyde dehydrogenase homologs. In certain embodiments, acetate byproduct titer at the end of fermentation 10 g/l or less, preferably 5 g/l or less, and most preferably 2.5 g/l or less. In certain embodiments, acetate byproduct yield at the end of fermentation is 10% or less, 5% or less, 2.5% or less, and preferably, 1% or less.

Decreasing or Eliminating Expression of Glycerol-3-phosphate Dehydrogenase

In addition to the possible byproducts derived from pyruvate and isobutyric acid pathway intermediates and product (as listed in Table 2), additional byproducts can arise from intermediates in glycolysis. Glycerol is a common byproduct that occurs under conditions of excess NADH. NAD-dependent glycerol-3-phosphate dehydrogenase catalyzes the conversion of dihydroxyacetone phosphate (glycerone phosphate) to glycerol-3-phosphate. NAD-dependent glycerol-3-phosphate dehydrogenase activity leads to the formation of the undesired byproduct glycerol. In $P.$ $kudriavzevii$, NAD-dependent glycerol-3-phosphate dehydrogenase activity is encoded by the gene PkGPD1 (SEQ ID NO: 12).

Decreasing or eliminating the expression of NAD-dependent glycerol-3-phosphate dehydrogenase is useful for decreasing glycerol byproduct accumulation. In some embodiments of the present disclosure, recombinant host cells may contain one or more genetic disruptions in one or more nucleic acids encoding a glycerol-3-phosphate dehydrogenase that gives rise to decreased, altered or eliminated expression and/or protein activity. In embodiments where the recombinant host cell is a *P. kudriavzevii* strain, the glycerol-3-phosphate dehydrogenase is PkGPD1. In some embodiments, recombinant host cells of the present disclosure may contain one or more genetic disruption(s) in one or more PkGPD1 homologs with at least 60%, at least 70%, at least 80%, at least 90%, at least 95%, or more than 95% homology when compared with PkGPD1.

In some embodiments, recombinant host cells may contain heterologous nucleic acids encoding isobutyric pathway enzymes and may further contain one or more genetic disruptions in one or more nucleic acids encoding glycerol-3-phosphate dehydrogenase. In certain embodiments, glycerol byproduct titer at the end of fermentation is 10 g/l or less, preferably at a titer of 5 g/l or less, and most preferably at a titer of 2.5 g/l or less. In certain embodiments, glycerol byproduct yield at the end of fermentation is 10% or less, 5% or less, 2.5% or less, and preferably, 1% or less.

Genetic Engineering

Expression of isobutyric acid pathway enzymes in host cells can be achieved by transforming host cells with exogenous nucleic acids encoding isobutyric acid pathway enzymes, thus producing recombinant host cells of the present disclosure. The same is true for expression of ancillary proteins. Any method can be used to introduce exogenous nucleic acids into a host cell to produce a recombinant host cell of the present disclosure. Many such methods are known to practitioners in the art. Some examples include electroporation, transformation, conjugation and homologous recombination.

Recombinant host cells of the present disclosure may contain one or more exogenous nucleic acid molecules/elements, as well as single or multiple copies of a particular exogenous nucleic acid molecule/element as described herein. These molecules/elements may contain transcriptional promoters, transcriptional terminators, protein coding regions, open reading frames, regulatory sites, flanking sequences for homologous recombination, and intergenic sequences.

Exogenous nucleic acids can be maintained by recombinant host cells in various ways. In some embodiments, exogenous nucleic acids are integrated into the host cell genome. In other embodiments, exogenous nucleic acids are maintained in an episomal state that can be propagated, either stably or transiently, to daughter cells. Exogenous nucleic acids may include selectable markers to ensure propagation. In some embodiments, the exogenous nucleic acids are maintained in recombinant host cells with selectable markers. In some embodiments, the selectable markers are removed and exogenous nucleic acids are maintained in a recombinant host cell or strain without selection. In some embodiments, removal of selectable markers is advantageous for downstream processing and purification of the fermentation product.

In some embodiments, endogenous nucleic acids (i.e., genomic or chromosomal elements of a host cell), are genetically disrupted to alter, mutate, modify, modulate, disrupt, enhance, remove, or inactivate a gene product. In some embodiments, genetic disruptions alter expression or activity of proteins native to a host cell. In some embodiments, genetic disruptions circumvent unwanted byproduct formation or byproduct accumulation. Genetic disruptions occur according to the principle of homologous recombination via methods well known in the art. Disrupted endogenous nucleic acids can contain open reading frames as well as genetic material that is not translated into protein. In some embodiments, one or more marker genes replace deleted genes by homologous recombination. In some of these embodiments, the one or more marker genes are later removed from the chromosome using techniques known to practitioners in the art.

Methods of Producing Isobutyric Acid

Methods are provided herein for producing isobutyric acid from recombinant host cells of the present disclosure. In certain embodiments, the methods include the steps of: 1) culturing a recombinant host cell as provided by the present disclosure in a fermentation broth containing at least one carbon source such that isobutyric acid is produced; and 2) recovering the isobutyric acid from the fermentation broth.

Fermentative Production of Isobutyric Acid By Recombinant Host Cells

Any of the recombinant host cells of the present disclosure can be cultured to produce and/or secrete isobutyric acid. Materials and methods for the maintenance and growth of prokaryotic and eukaryotic cells, as well as fermentation conditions, are well known to practitioners of ordinary skill in the art. It is understood that consideration must be given to appropriate culture medium, pH, temperature, revival of frozen stocks, growth of seed cultures and seed trains, and requirements for aerobic, microaerobic, or anaerobic conditions, depending on the specific requirements of the host cells, the fermentation, and process flows.

The methods of producing isobutyric acid provided herein may be performed in a suitable fermentation broth in a suitable bioreactor such as a fermentation vessel, including but not limited to a culture plate, a flask, or a fermenter. Further, the methods can be performed at any scale of fermentation known in the art to support microbial production of small-molecules on an industrial scale. Any suitable fermenter may be used including a stirred tank fermenter, an airlift fermenter, a bubble column fermenter, a fixed bed bioreactor, or any combination thereof.

In some embodiments of the present disclosure, the fermentation broth is any fermentation broth in which a recombinant host cell capable of producing isobutyric acid according to the present disclosure, and can subsist (i.e., maintain growth, viability, and/or catabolize glucose or other carbon source). In some embodiments, the fermentation broth is an aqueous medium containing assimilable carbon, nitrogen, and phosphate sources. Such a medium can also include appropriate salts, minerals, metals, and other nutrients required for microbial growth and propagation. In some embodiments, the carbon source and each of the essential cell nutrients are provided to the fermentation broth incrementally or continuously, and each essential cell nutrient is maintained at essentially the minimum level required for efficient assimilation by growing cells. Examples of cell growth procedures include batch fermentation, fed-batch fermentation with batch separation, fed-batch fermentation with continuous separation, and continuous fermentation with continuous separation. These procedures are well known to practitioners of ordinary skill in the art.

In some embodiments of the present disclosure, the handling and culturing of recombinant host cells to produce isobutyric acid may be divided up into phases, such as growth phase, production phase, and/or recovery phase. The following paragraphs provide examples of features or purposes that may relate to these different phases. One skilled in the art will recognize that these features or purposes may vary based on the recombinant host cells used, the desired isobutyric acid yield, titer, and/or productivity, or other factors. While it may be beneficial in some embodiments for the isobutyric acid pathway enzymes, ancillary proteins and/or endogenous host cell proteins to be constitutively expressed, in other embodiments, it may be preferable to selectively express or repress any or all of the aforementioned proteins.

During growth phase, recombinant host cells may be cultured to focus on growing cell biomass by utilizing the carbon source provided. In some embodiments, the expression of isobutyric acid pathway enzymes and/or ancillary proteins is repressed or uninduced during growth phase. In some embodiments, no appreciable amount of isobutyric acid or any of its pathway intermediates is made. In some embodiments, proteins that contribute to cell growth and/or cellular processes may be selectively expressed.

During production phase, recombinant host cells may be cultured to stop producing cell biomass and to focus on isobutyric acid biosynthesis by utilizing the carbon source provided. In some embodiments, isobutyric acid pathway enzymes and/or ancillary proteins may be selectively expressed during the production phase to generate high product titers, yields and productivities. The production phase is synonymous with fermentation, fermentation run and/or fermentation phase.

In some embodiments, the growth and production phases take place at the same time. In other embodiments, the growth and production phases are separate. While in some embodiments, product is made exclusively during production phase, in other embodiments some product is also made during growth phase before production phase begins.

The recovery phase marks the end of the production phase, during which cellular biomass is separated from fermentation broth and isobutyric acid is purified from fermentation broth. Those skilled in the art will recognize that in some fermentation process, e.g., fill-draw and continuous fermentations, there may be multiple recovery phases where fermentation broth containing biomass and isobutyric acid are removed from the fermentation system. The draws of fermentation broth may be processed independently or may be stored, pooled, and processed together. In other fermentation processes, e.g., batch and fed-batch fermentations, there may only be a single recovery phase.

Fermentation procedures are particularly useful for the biosynthetic production of commercial isobutyric acid. It is understood by practitioners of ordinary skill in the art that fermentation procedures can be scaled up for manufacturing isobutyric acid and examples of fermentation procedures include, for example, fed-batch fermentation and batch product separation; fed-batch fermentation and continuous product separation; batch fermentation and batch product separation; and continuous fermentation and continuous product separation.

Carbon Source for Fermentation

The carbon source provided to the fermentation can be any carbon source that can be fermented by the recombinant host cell. Suitable carbon sources include, but are not limited to, a variety of sugars including monosaccharides, disaccharides, polysaccharides, glycerol, acetate, ethanol, methanol, methane, or one or more combinations thereof. Examples of monosaccharides suitable for use in accordance to the methods of the present disclosure include, but are not limited to, dextrose (glucose), fructose, galactose, xylose, arabinose, and any combination thereof. Examples of disaccharides suitable for use in accordance to the methods of the present disclosure include, but are not limited to, sucrose, lactose, maltose, trehalose, cellobiose, and any combination thereof. Examples of polysaccharides suitable for use in accordance to the methods of the present disclosure include, but are not limited to, starch, glycogen, cellulose, and combinations thereof. In some embodiments, the carbon source is dextrose. In other embodiments, the carbon source is sucrose. In some embodiments, mixtures of some or all the aforementioned carbon sources can be used in fermentation.

Fermentation pH

The pH of the fermentation broth can be controlled by the addition of acid or base to the culture medium. Preferably, fermentation pH is controlled at the beginning of fermentation and then allowed to drop as isobutyric acid accumulates in the broth, minimizing the amount of base added to the fermentation (thereby improving process economics) as well as minimizing the amount of salt formed. Specifically, the pH during fermentation is maintained in the range of 2-8, and more preferably, in the range of 4-8. At the end of fermentation, the final pH is in the range of 2-5. Non-limiting examples of suitable acids used to control fermentation pH include aspartic acid, acetate, hydrochloric acid, and/or sulfuric acid. Non-limiting examples of suitable bases used to control fermentation pH include sodium bicarbonate ($NaHCO_3$), sodium hydroxide (NaOH), potassium bicarbonate ($KHCO_3$), potassium hydroxide (KOH), calcium hydroxide ($Ca(OH)_2$), calcium carbonate ($CaCO_3$), ammonia, ammonium hydroxide, and/or diammonium phosphate. In some embodiments, a concentrated acid or concentrated base is used to limit dilution of the fermentation broth.

In some embodiments of the present disclosure, base is used for modulating pH and examples of base include $NaHCO_3$, NaOH, $Ca(OH)_2$, $CaCO_3$, $NH_4$, $KHCO_3$ and KOH. Base cations and isobutyrate anions react to form ionic compounds in fermentation broths. For example, base $Na^+$ cations and isobutyrate anions react to form sodium butyrate. In some embodiments, the ionic compounds form by base cations and isobutyrate anions are soluble in fermentation broth. In other embodiments, the ionic compounds formed by base cations and isobutyrate anions are insoluble and may crystallize in the fermentation broth.

Fermentation Temperature

The temperature of the fermentation broth can be any temperature suitable for growth of the recombinant host cells and/or production of isobutyric acid. Preferably, during isobutyric acid production, the fermentation broth is maintained within a temperature range of from about 20° C. to about 45° C., from about 25° C. to about 45° C., or from about 30° C. to about 42° C. In some embodiments, the fermentation broth is maintained at a temperature of about 20° C. In some embodiments, the fermentation broth is maintained at a temperature of about 25° C. In some embodiments, the fermentation broth is maintained at a temperature of about 30° C. In some embodiments, the fermentation broth is maintained at a temperature of about 35° C. In some embodiments, the fermentation broth is maintained at a temperature of about 40° C.

Oxygen/Aeration

Generally speaking, microbial production of isobutyric acid from glucose results in the formation of NADH and/or NADPH, redox cofactors that must be converted back to NAD+ and NADP+ in order to maintain catabolism of glucose. Under aerobic conditions, microbes will commonly use molecular oxygen as an electron acceptor, enabling these cofactors to be reoxidized. If the fermentation is not appropriately oxygenated, isobutyric acid production can decrease. During cultivation, aeration and agitation conditions are selected to produce an oxygen transfer rate (OTR; amount of dissolved oxygen in a fermentation medium) that results in isobutyric acid formation. In various embodiments, fermentation conditions are selected to produce an OTR of greater than 10 mmol/l/hr. In some embodiment, fermentation conditions are selected to produce an OTR of greater than 20 mmol/l/hr, greater than 30 mmol/l/hr, greater than 40 mmol/l/hr, greater than 50 mmol/l/hr, greater than 75 mmol/l/hr, greater than 100 mmol/l/hr, greater than 125 mmol/l/hr, greater than 150 mmol/l/hr, greater than 175 mmol/l/hr, or greater than 200 mmol/l/hr. OTR as used herein refers to the volumetric rate at which oxygen is consumed during the fermentation. Inlet and outlet oxygen concentrations can be measured by exhaust gas analysis, for example by mass spectrometers. OTR can be calculated by one of ordinary skill in the art using the Direct Method described in Bioreaction Engineering Principles $3^{rd}$ Edition, 2011, Spring Science+Business Media, p. 449. The recombinant host cells of the present disclosure are able to produce isobutyric acid under a wide range of oxygen concentrations.

Fermentation Yields and Titers

A high yield of isobutyric acid from the provided carbon source(s) is desirable to decrease the production cost. As used herein, yield is calculated as the percentage of the mass of carbon source catabolized by recombinant host cells of the present disclosure and used to produce isobutyric acid. In some cases, only a fraction of the carbon source provided to a fermentation is catabolized by the cells, and the remainder is found unconsumed in the fermentation broth or is consumed by contaminating microbes in the fermentation. Thus, it is important to ensure that fermentation is both substantially pure of contaminating microbes and that the concentration of unconsumed carbon source at the completion of the fermentation is measured. For example, if 100 grams of glucose is fed into the fermentation, and at the end of the fermentation 25 grams of isobutyric acid are produced and there remains 10 grams of glucose, the isobutyric acid yield is 27.7% (i.e., 25 grams isobutyric acid from 90 grams glucose). In certain embodiments of the methods provided herein, the final yield of isobutyric acid on the carbon source is at least 10%, at least 20%, at least 30%, at least 35%, at least 40%, or greater than 40%. In certain embodiments, the recombinant host cells provided herein are capable of producing at least 35%, at least 40%, or greater than 40% by weight of carbon source to isobutyric acid. Those skilled in the art will recognize that when an isobutyric acid salt (i.e., isobutyrate) is found in the fermentation broth the isobutyric acid yield can be determined by calculating the mols of isobutyric acid salt present and adjusting for the molecular weight difference between the isobutyric acid salt and isobutyric acid.

In addition to yield, the titer (or concentration), of isobutyric acid produced in the fermentation is another important metric for production. Assuming all other metrics are equal, a higher titer is preferred to a lower titer. Generally speaking, titer is provided as grams of product (e.g., isobutyric acid) per liter of fermentation broth (i.e., g/l). In some embodiments, the isobutyric acid titer is at least 1 g/l, at least 5 g/l, at least 10 g/l, at least 15 g/l, at least 20 g/l, at least 25 g/l, at least 30 g/l, at least 40 g/l, at least 50 g/l, at least 60 g/l, at least 70 g/l, at least 80 g/l, at least 90 g/l, at least 100 g/l, or greater than 100 g/l at some point during the fermentation, and preferably at the conclusion of the fermentation. As with yield calculations, those skilled in the art will recognize that an isobutyric acid titer can be calculated from the isobutyric acid salt titer by adjusting for molecular weight differences between the isobutyric acid salt and isobutyric acid.

Further, productivity, or the rate of product (i.e., isobutyric acid) formation, is important for decreasing production cost, and, assuming all other metrics are equal a higher productivity is preferred over a lower productivity. Generally speaking, productivity is provided as grams product produced per liter of fermentation broth per hour (i.e., g/l/hr). In some embodiments, isobutyric acid productivity is at least 0.1 g/l, at least 0.25 g/l, at least 0.5 g/l, at least 0.75 g/l, at least 1.0 g/l, at least 1.25 g/l, at least 1.25 g/l, at least 1.5 g/l, or greater than 1.5 g/l over some time period during the fermentation.

Practitioners of ordinary skill in the art understand that high-performance liquid chromatography (HPLC) is an appropriate method to determine the amount of isobutyric acid and/or isobutyric acid salts produced, the amount of any byproducts produced (e.g., organic acids and alcohols), the amount of any pathway metabolite or intermediate produced, and the amount of unconsumed glucose left in the fermentation broth. Aliquots of fermentation broth can be isolated for analysis at any time during fermentation, as well as at the end of fermentation. Briefly, molecules in the fermentation broth are first separated by liquid chromatography (LC); then, specific liquid fractions are selected for analysis using an appropriate method of detection (e.g., UV-VIS, refractive index, and/or photodiode array detectors). In some embodiments of the present disclosure, an organic acid salt (e.g., acetate and isobutyrate) is the fermentative product present in the fermentation broth. Practitioners in the art understand that the organic acid salt is acidified before or during HPLC analysis (producing acetic acid and isobutyric acid). Hence, the organic acid concentration calculated by HPLC analysis can be used to calculate the organic acid salt titer in the fermentation broth by adjusting for difference in molecular weight between the two compounds.

Gas chromatography is also an appropriate method to determine the amount of target product and byproducts, particularly if they are volatile. Samples of fermentation headspace can be isolated for analysis at any time during and after fermentation. Practitioners in the art understand that molecules are carried by an inert gas carries as they move through a column for separation and then arrive at a detector.

EXAMPLES

Methodology: Parent Strain

The parent strain in Example 1 was a *P. kudriavzevii* strain auxotrophic for histidine and uracil (i.e., the strain cannot grow in media without histidine and uracil supplementation). Histidine auxotrophy in the parent strain enables selection of new, engineered strains that carry a HIS3 marker, enabling histidine prototrophy and indicating desired strain construction. Likewise, uracil auxotrophy in the parent strain enables selection of new, engineered strains that carry a URA3 marker, enabling uracil prototrophy and indicating desired strain construction. Thus, cells that were successfully modified with exogenous nucleic acids to contain desired genetic modifications can grow in media without histidine and/or uracil supplementation, dependent on the selection marker included in the exogenous nucleic acid. Following confirmation of correct strain engineering, the selection marker(s) were removed by, for example, homologous recombination and marker loopout. Removing the marker enables subsequent rounds of strain engineering using the same selection markers.

Methodology: Media

Complete Supplement Mixture (CSM) Medium.

CSM medium comprised Adenine 10 mg/L; L-Arginine HCl 50 mg/L; L-Aspartic Acid 80 mg/L; L-Histidine HCl 20 mg/L; L-Isoleucine 50 mg/L; L-Leucine 100 mg/L; L-Lysine HCl 50 mg/L; L-Methionine 20 mg/L; L-Phenylalanine 50 mg/L; L-Threonine 100 mg/L; L-Tryptophan 50 mg/L; L-Tyrosine 50 mg/L; Uracil 20 mg/L; L-Valine 140 mg/L. The YNB used in the CSM comprised Ammonium sulfate 5.0 g/L, Biotin 2.0 µg/L, Calcium pantothenate 400 µg/L, Folic acid 2.0 µg/L, Inositol 2.0 mg/L, Nicotinic acid 0-400 µg/L, p-Aminobenzoic acid 200 µg/L, Pyridoxine HCl 400 µg/L, Riboflavin 200 µg/L, Thiamine HCl 400 µg/L, Boric acid 500 µg/L, Copper sulfate 40 µg/L, Potassium iodide 100 µg/L, Ferric chloride 200 µg/L, Manganese sulfate 400 µg/L, Sodium molybdate 200 µg/L, Zinc sulfate 400 µg/L, Potassium phosphate monobasic 1.0 g/L, Magnesium sulfate 0.5 g/L, Sodium chloride 0.1 g/L, and Calcium chloride 0.1 g/L.

Complete Supplement Mixture Minus Histidine (CSM-his) Medium.

CSM-His medium is identical to CSM medium with the exception that histidine was not included in the medium. Engineered strains auxotrophic for histidine are unable to grow on CSM-His medium while engineered strains containing exogenous nucleic acids comprising a histidine selectable marker (e.g., HIS3) are capable of growth in CSM-His medium.

Complete Supplement Mixture Minus Uracil (CSM-Ura) Medium.

CSM-Ura medium is identical to CSM medium with the exception that uracil was not included in the medium. Engineered strains auxotrophic for uracil are unable to grow on CSM-Ura medium while engineered strains containing exogenous nucleic acids comprising a uracil selectable marker (e.g., URA3) are capable of growth in CSM-Ura medium.

BM02 Medium.

BM02 medium is Glucose 125 g/l, $K_2SO_4$ 0.816 g/l, $Na_2SO_4$ 0.1236, $MgSO_4$-$7H_2O$ 0.304 g/l, Urea 4.3 g/l, Myo-inositol 2 mg/l, Thiamin HCl 0.4 mg/l, Pyridoxal HCl 0.4 mg/l, Niacin 0.4 mg/l, Ca-Pantothenate 0.4 mg/l, Biotin µg/l, Folic acid 2 µg/l, PABA 200 µg/l, Riboflavin 200 µg/l, Boric acid 0.25 mg/l, Copper sulfate pentahydrate 393 µg/l, Iron sulfate 11.0 mg/l, Manganese chloride 1.6 mg/l, Sodium molybdate 100 µg/l, Zinc sulfate 4 mg/l, and EDTA 11 mg/l.

BM02-P Medium.

BM02-P medium is BM02 medium with 1 g/l potassium phosphate.

YPE Medium.

YPE medium is Bacto peptone 20 g/l, Yeast extract 10 g/l, and Ethanol 2%.

Example 1: Construction of Recombinant *P. kudriavzevii* Strain, LPK15779, with Eliminated Expression of Pyruvate Decarboxylase This example describes the construction of a pyruvate decarboxylase (PDC) minus *P. kudriavzevii*, LPK15779, wherein all three PDC genes, i.e., Pdc1, Pdc5 and Pdc6, were genetically disrupted to eliminate expression of PkPDC1, PkPDC5, and PkPDC6.

The parent *P. kudriavzevii* strain used in this example was auxotrophic for uracil and histidine. To eliminate PDC expression, the Pdc1, Pdc5 and Pdc6 genes in the *P. kudriavzevii* genome were disrupted sequentially. The *P. kudriavzevii* strain was diploid and two copies of each pyruvate decarboxylase gene were present at the indicated locus; therefore, disruption of each gene was achieved by deleting both gene copies.

A URA3 selectable marker, amplified by PCR, was provided to the parent *P. kudriavzevii* strain to complement the uracil auxotrophic deficiency. The URA3 selectable marker contained unique upstream and downstream homologous regions for homologous recombination at the *P. kudriavzevii* Pdc1 locus, a transcriptional promoter, a URA3 coding region, and a transcriptional terminator. The transcriptional promoter 5' of URA3 was the *P. kudriavzevii* TEF1 promoter (pPkTEF1) and the transcriptional terminator 3' of URA3 was the *S. cerevisiae* TDH3 terminator (tScTDH3). The PCR product of the URA3 selectable marker was gel-purified and provided as exogenous nucleic acids to *P. kudriavzevii*. Transformation was carried out in a single step and gene deletion was achieved by homologous recombination. Transformants were selected on CSM-Ura medium and successful deletion of both copies of the gene encoding PkPDC1 was confirmed by genetic sequencing of this locus and the flanking regions. After successful construction of a recombinant *P. kudriavzevii* comprising a Pdc1 genetic disruption, the URA3 selectable marker was removed from the recombinant strain genome by recombination and marker loopout.

The URA3 selectable marker and genetic disruption strategy described above were reused to next disrupt the Pdc5 and Pdc6 genes in succession. Deletion of the native genes encoding PkPDC5 and PkPDC6 was confirmed by genetic sequencing of this locus and the flanking regions. The *P. kudriavzevii* strain that results from Example 1, LPK15779, was without any URA3 selectable marker. The URA3 selectable marker was absent in the following examples that describe further strain engineering or strain performance testing. Thus, Example 1 produces a PDC minus (i.e., contains deletion of native genes encoding PkPDC1, PkPDC5, and PkPDC6), uracil and histidine auxotrophic *P. kudriavzevii*, which was the background strain for Example 2 below.

Example 2: Construction of Recombinant *P. kudriavzevii* Background Strain, LPK15942, with Eliminated Expression of Pyruvate Decarboxylase and Pyruvate Dehydrogenase Complex This example describes the construction of a pyruvate dehydrogenase complex (PDH) minus *P. kudriavzevii*, LPK15942, wherein expression of PDH was eliminated via genetic disruption of the Pda1 gene. Pda1 encodes for the E1 α-subunit (PkPDA1) of the PDH. When PkPDA1 expression is eliminated, PDH cannot assemble into a functional complex. Thus, PDH expression is also eliminated and the recombinant host cell is unable to catalyze the conversion of pyruvate, coenzyme A and $NAD^+$ to acetyl-CoA, $CO_2$ and NADH in the host cell mitochondria. This genetic disruption has the end result of decreasing respiration, thereby decreasing formation of byproduct $CO_2$ and increasing isobutyric acid production.

PkPDA1 was genetically disrupted using the same engineering strategy as described above in Example 1. LPK15779, a PDC minus, uracil and histidine auxotrophic *P. kudriavzevii* strain from Example 1 was the background strain used in Example 2.

A HIS3 selectable marker, amplified by PCR, was provided to the background strain (from Example 1) to complement the histidine auxotophic deficiency. The HIS3 selectable marker contained unique upstream and downstream homologous regions for homologous recombination at the Pda1 locus of the background strain genome, a transcriptional promoter, a HIS3 coding region, and a transcriptional terminator. The transcriptional promoter 5' of HIS3 was the *P. kudriavzevii* TEF1 promoter (pPkTEF1) and the transcriptional terminator 3' of HIS3 was the *S. cerevisiae* TDH3 terminator (tScTDH3). The PCR product of the HIS3 selectable marker was gel-purified and provided as exogenous nucleic acids to the background strain. Transformation was carried out in a single step and gene deletion was achieved by homologous recombination. Transformants were selected on CSM-His medium and successful deletion of both copies of the genes encoding PkPDA1 was confirmed by genetic sequencing of this locus and the flanking regions. After successful construction of a recombinant *P. kudriavzevii* comprising a Pda1 genetic disruption, the HIS3 selectable marker was removed from the recombinant strain genome by recombination and marker loopout.

The *P. kudriavzevii* strain that resulted from Example 2, LPK15942, was without a HIS3 selectable marker. The HIS3 selectable marker was absent in the following examples that describe further strain engineering or strain performance testing. Example 2 produced a PDC minus, PDH minus, uracil and histidine auxotrophic *P. kudriavzevii* (i.e., the strain contained deletion of native genes encoding PkPDC1, PkPDC5, PkPDC6, and PkPDA1), which was the background strain used in Example 3.

Example 3: Recombinant *P. kudriavzevii* Background Strain, LPK15942, does not Naturally Produce Isobutyric Acid This example describes the culturing and analysis of LPK15942 (from Example 2) for isobutyric acid production before LPK15942 was used as the background strain for genomic integration of the isobutyric acid pathway (Example 5, below). LPK15942 colonies were used to inoculate replicate tubes of 15 ml of YPE medium and incubated at 30° C. with 80% humidity and shaking at 250 rpm for 20 hours. These replicate tubes of pre-cultures were used to inoculate baffled flask replicates of 250 ml of BM02-P media with 10% glucose, 1% ethanol and 40 g/l CaCO$_3$. Pre-cultures were diluted 50× with 1 M HCl for OD$_{600}$ measurements to inform appropriate dilution of pre-cultures to produce a starting culture biomass of 1 g/l dry cell weight (DCW). Baffled flask cultures were then incubated at 30° C. with 80% humidity and shaking at 250 rpm. After 48 hours, the cultures were diluted 10× with 12 M HCl, spin-filtered and frozen for storage. Samples were analyzed by HPLC within 48 hours of harvest.

For HPLC analysis, frozen samples were thawed analyzed by HPLC using a Bio-Rad Aminex 87H column (300×7.8 mm) and a Bio-Rad Fermentation Monitoring column (#1250115; 150×7.8 mm) installed in series, with an isocratic elution rate of 0.8 ml/min with water at pH 1.95 (with sulfuric acid) at 30° C. Refractive index and UV 210 nm measurements were acquired for 35 minutes.

The LPK15942 background strain did not produce detectable amounts of isobutyric acid. Thus, all engineered *P. kudriavzevii* strains built from this background strain were incapable of producing isobutyric acid without the heterologous nucleic acids that encode the isobutyric acid pathway (Table 1 and Example 5).

Example 4: Recombinant *P. kudriavzevii* Background Strain, LPK15942, does not Produce Significant Amounts of the Byproduct Ethanol This example describes the culturing and analysis of LPK15942 (from Example 2) for basal level production of ethanol before LPK15942 was used as the background strain for genomic integration of the isobutyric acid pathway (Table 1 and Example 5). Native *P. kudriavzevii* cells are capable of producing the downstream metabolite ethanol via PDC-mediated decarboxylation of pyruvate to acetaldehyde. LPK15942 was a PDC minus strain incapable of decarboxylating pyruvate to acetaldehyde, and consequently incapable of producing ethanol. The PDC minus phenotype was constructed to provide the engineered isobutyric acid pathway access to the cellular pool of pyruvate without having to compete with PDC-mediated decarboxylation. LPK15942 should produce less ethanol than the PDC plus, wild type strain, designated LPK15, which was a *P. kudriavzevii* strain with all native PDC genes intact. LPK15942 and LPK15 were cultured and analyzed by HPLC according to methods described above, in Example 3.

The LPK15942 (PDC minus) background strain did not produce detectable amounts of ethanol while the LPK15 (PDC plus) strain produced greater than 50 mM of ethanol. This observation indicated that the PkPDC1, PkPDC5 and PkPDC6 genetic disruptions in LPK15942 produced a desired phenotype that did not produce excessive ethanol byproduct by PDC-mediated depletion of pyruvate. Thus, the cellular pool of pyruvate was available for the first reaction in the isobutyric acid pathway (Table 1).

Example 5: Construction of Recombinant *P. kudriavzevii* Strains, LPK151338 and LPK151339, Expressing Isobutyric Acid Pathway Enzymes and Eliminating Expression of GPD1

This example describes the construction of recombinant host cells of the present disclosure that contain heterologous nucleic acids encoding isobutyric acid pathway enzymes (Table 1). The PDC minus, PDH minus, uracil and histidine auxotrophic *P. kudriavzevii*, LPK15942, from Example 2 was the background strain used in Example 5.

The heterologous nucleic acids used in this example encoded the following isobutyric acid pathway enzymes: *B. subtilis* AlsS (BsALSS; SEQ ID NO: 1), *E. coli* IlvC (EcILVC; SEQ ID NO: 2), *L. lactis* IlvD (LlILVD; SEQ ID NO: 3), *L. lactis* KivD (LlKIVD; SEQ ID NO: 4), and *E. coli* FeaB (EcFEAB; SEQ ID NO: 5). The genes encoding these proteins were codon-optimized for yeast and were synthesized and provided by Twist Bioscience; each gene was cloned into its own entry vector, pEV, along with an upstream transcriptional promoter and a downstream transcriptional terminator. The transcriptional promoters cloned in front (5') of each gene were constitutive and derived from *P. kudriavzevii*. The promoters for BsALSS, EcILVC, LlILVD, LlKIVD, and EcFEAB were the PGK1 promoter (pPkPGK1), the ENO1 promoter (pPkENO1), the FBA1 promoter (pPkFBA1), the GPM1 promoter (pPkGPM1), and the TDH1 promoter (pPkTDH1), respectively. The transcriptional terminators cloned behind (3') of each gene were derived from *S. cerevisiae*. The terminators for BsALSS, EcILVC, LlILVD, LlKIVD, and EcFEAB were the HXT1 terminator (tScHXT1), the TEF1 terminator (tScTEF1), the GRE3 terminator (tScGRE3), the PCY3 terminator (tScPYC2), and the TPI1 terminator (tScTPI1), respectively. Additionally, a HIS3 marker was included in the heterologous expression cassette to complement the histidine auxotrophic deficiency in the parent strain. This HIS3 marker contained a transcriptional promoter, a HIS3 coding region, and a transcriptional terminator. The transcriptional promoter 5' of HIS3 was the P. kudriavzevii TEF1 promoter (pPkTEF1) and the transcriptional terminator 3' of HIS3 was the S. cerevisiae TDH3 terminator (tScTDH3). Each gene was amplified from its respective pEV vector using primers with upstream and downstream homologous regions to neighboring genetic elements to drive correct assembly of the full-length pathway. The upstream and downstream homologous regions were 25 bp to 700 bp in length. The 5' and 3' ends of the expression cassette contained regions homologous to the genomic sequences upstream and downstream of the P. kudriavzevii GPD1 locus, thereby facilitating integration of the heterologous nucleic acids encoding the isobutyric acid pathway enzymes at the GPD1 locus in the P. kudriavzevii genome. Consequently, one or both copies of the PkGPD1 gene were deleted from the host genome; thus, genomic integration of the isobutyric acid pathway simultaneously decreased or eliminated expression of PkGPD1.

All PCR products were gel-purified and provided as exogenous nucleic acids to P. kudriavzevii. Transformation was carried out in a single step. Transformants were selected on CSM-His medium. Successful integration of all nucleic acids encoding isobutyric acid pathway enzymes as well as deletion of one or both copies of the genes encoding PkGPD1 were confirmed by genetic sequencing of this locus and the flanking regions After successful construction of recombinant P. kudriavzevii host cells comprising isobutyric acid pathway genes, the HIS3 selectable markers were removed from recombinant host cell genomes by recombination and marker loopout. Example 3 produced recombinant host cells that contained heterologous nucleic acids encoding isobutyric acid pathway enzymes and additionally contained genetic disruption of PkPDC1, PkPDC5, PkPDC6, PkPDA1, and PkGPD1. The resulting strains were additionally auxotrophic for uracil and histidine. The recombinant host cell with one copy of PkGPD1 disrupted with a single genomic integration of the isobutyric acid pathway (i.e., a single GPD1 knockout) was designated LPK151338. The recombinant host cell with both copies of PkGPD1 disrupted with the isobutyric acid pathway genes (i.e., a double GPD1 knockout and a GPD minus phenotype) was designated LPK151339.

Example 6: Construction of Recombinant P. kudriavzevii Strains, LPK151336 and LPK151337, with Single or Double GPD1 Genetic Disruptions Via HIS3 Gene Integration at the GPD1 Locus The same strain engineering strategy described in Example 5 was used to construct P. kudriavzevii strains with single or double GPD1 knockouts by genomic integration of the HIS3 selectable marker at the GPD1 locus. These strains were constructed to serve as GPD1 knockout control strains that lack the isobutyric acid pathway. In this example, the HIS3 selectable markers were not removed from recombinant host cell genomes. This example produced recombinant host cells that were auxotrophic for uracil and prototrophic for histidine, and further contained genetic disruption of PkPDC1, PkPDC5, PkPDC6, PkPDA1 and PkGPD1. The recombinant host cell with one copy of PkGPD1 disrupted with a single genomic integration of HIS3 (i.e., a single GPD1 knockout) was designated LPK151336. The recombinant host cell with both copies of PkGPD1 disrupted with HIS3 (i.e., a double GPD1 knockout and a GPD minus phenotype) was designated LPK151337.

Example 7: Recombinant P. kudriavzevii Strains LPK151338 and LPK151339 Produce Isobutyric Acid Pathway Intermediate and Product This example describes the culturing and analysis of recombinant host cells LPK151338 and LPK151339 from Example 5 (PDC minus, PDH minus, and single or double GPD1 knockout with single or double insertion of the isobutyric acid pathway), and LPK151336 and LPK151337 from Example 6 (PDC minus, PDH minus, and single or double GPD1 knock out with single or double insertion of the HIS3 gene) for in vivo production of the isobutyric acid pathway intermediate acetolactate, and product isobutyric acid (Table 1). All four recombinant strains were cultured and analyzed by HPLC according to methods described above in Example 3.

Both LPK151338 and LPG151339 produced about 6.5 mM to about 7.5 mM of isobutyric acid, and about 9.5 mM to about 10.5 mM of isobutyric acid, respectively. In contrast, the LPK15942 background strain did not produce detectable amounts of isobutyric acid (Example 3). Further, both LPK151338 and LKP151339 recombinant host cells produced about 10 g/l of acetolactate, which is the product of the first step in the isobutyric pathway (catalyzed by heterologous acetolactate synthase; Table 1). This example demonstrated, in accordance with the present disclosure, the expression of heterologous nucleic acids encoding isobutyric acid pathway enzymes (Table 1 and Example 5) in recombinant P. kudriavzevii for isobutyric acid production.

In addition, LPK151338 and LKP151339 produced about 165 mM to about 175 mM of acetoin, and about 170 mM to about 180 mM of acetoin, respectively. LPK151338 and LKP151339 contained a heterologous acetolactate synthase of the isobutyric acid pathway, enabling increased acetolactate production. Acetolactate can spontaneously convert to diacetyl, and acetolactate and/or diacetyl can migrate from the cytosol into the mitochondria, where the P. kudriavzevii native mitochondrial Bdh1 protein (PkBDH1) converts diacetyl to acetoin. Thus, increased amounts of acetolactate enabled increased acetoin production in the mitochondria. In contrast, the LPK151336 and LPK151337 strains, both PDC minus and PDH minus strains from Example 6 that lack the isobutyric acid pathway, produced about 15 mM to about 25 mM acetoin. Detection of increased acetoin levels in LPK151338 and LPK151339 in this example also demonstrated, in accordance with the present disclosure, the expression of heterologous nucleic acids encoding isobutyric acid pathway enzymes in recombinant P. kudriavzevii for isobutyric acid production.

Example 8: Recombinant P. kudriavzevii Strains LPK151338 and LPK151339 do not Produce the Byproduct Glycerol This example describes the culturing and analysis of LPK151338 (single GPD1 knockout) and LPK151339 (double GPD1 knockout; GPD minus) recombinant host cells (from Example 5) for in vivo production of glycerol. Native P. kudriavzevii cells are capable of producing the downstream metabolite glycerol via PkGPD1-mediated conversion of dihydroxyacetone phosphate (glycerone phosphate) to glycerol-3-phosphate. The presence of glycerol in fermentation media requires additional glycerol removal steps in isobutyric acid purification. The isobutyric acid pathway genes were inserted in the *P. kudriavzevii* GPD1 locus to disrupt expression of PkGPD1, thereby removing glycerol production in recombinant host cells. LPK151338 and LPK151339 were cultured and analyzed by HPLC according to methods described above in Example 3.

The single GPD1 knockout LPK151338 produced about 50 mM to about 110 mM of glycerol, while the double GPD1 knockout (hence, GPD1 minus) LPG151339 produced no detectable amounts of glycerol. This example demonstrates, in accordance with the present disclosure, the successful removal of glycerol from fermentation by genetic disruption of PkGPD1 in recombinant *P. kudriavzevii* for isobutyric acid production.

Example 9: Recombinant *P. kudriavzevii* Strains Expressing KARI Enzymes

This example describes the construction, culturing, and analysis of recombinant host cells of the present disclosure that contain heterologous nucleic acids encoding KARI enzymes. The strains were constructed identically to LPK15338 from Example 5 with the exception that different KARI enzymes were used in place of the *E. coli* IlvC KARI protein. The KARI enzymes expressed in this example were *Corynebacterium glutamicum* IlvC (UniProt ID: Q57179), *Lactococcus brevis* IlvC (UniProt ID: C2D2I9), *Lactococcus lactis* IlvC (UniProt ID: Q02138), *Pseudomonas fluorescens* IlvC (UniProt ID: Q4K608), *Pseudomonas putida* IlvC (UniProt ID: Q88DZ0), *Pseudomonas syringae* IlvC (UniProt ID: Q4ZY66), *Saccharomyces cerevisiae* mitochondrial Ilv5 (UniProt ID: P06168 comprising a deletion of the 47 N-terminal amino acids corresponding to the mitochondrial targeting sequence), and *Staphylococcus hominis* IlvC (UniProt ID: A0A1L8Y8D1). The heterologous nucleic acids encoding the isobutyric acid pathway enzymes were integrated at the GPD1 locus, deleting one of the two native GPD1 alleles.

The recombinant *P. kudriavzevii* strains were cultured and analyzed by HPLC according to methods described above in Example 3. *P. kudriavzevii* strains LPK15942 (which does not produce isobutyric acid, see Example 3), and LPK15338 (which does produce isobutyric acid, see Example 7), were included as negative and positive controls, respectively. The negative control, LPK15942, produced an undetectable amount of isobutyric acid while the positive control, LPK15338, produced over 0.7 g/l isobutyric acid. The engineered strains comprising KARI enzymes derived from *Corynebacterium glutamicum, Lactococcus brevis, Lactococcus lactis, Pseudomonas fluorescens, Pseudomonas putida, Pseudomonas syringae, Saccharomyces cerevisiae,* and *Staphylococcus hominis* described here all produced isobutyric acid titers greater than 0.1 g/l. Thus, this Example demonstrates that, in accordance with the present disclosure, that any one of various KARI enzymes are suitable for use in engineered *P. kudriavzevii* for production of isobutyric acid.

Example 10: Recombinant *P. kudriavzevii* Strains Producing Isobutyric Acid from a Mitochondrially Expressed Isobutyric Acid Pathway This example describes the construction, culturing, and analysis of recombinant host cells of the present disclosure that express the isobutyric acid pathway proteins in the host cell mitochondria. The isobutyric acid pathway enzymes used in this example were *Bacillus subtilis* AlsS, *Escherichia coli* IlvC, *Lactococcus lactis* DHAD, *Lactococcous lactis* KivD, and *Escherichia coli* FeaB described in Example 5 with the exception that each protein included the mitochondrial targeting sequence from *P. kudriavzevii* PDA1 (i.e., the 30 N-terminal amino acids). The heterologous nucleic acids encoding this mitochondrial isobutyric acid pathway were inserted at the GPD1 locus in the *P. kudriavzevii* genome, deleting one of the two GPD1 alleles.

The recombinant *P. kudriavzevii* strains were cultured and analyzed by HPLC according to methods described above in Example 3. *P. kudriavzevii* strains LPK15942 (which does not produce isobutyric acid, see Example 3), and LPK15338 (which does produce isobutyric acid, see Example 7), were included as negative and positive controls, respectively. The negative control, LPK15942, produced an undetectable amount of isobutyric acid while the positive control, LPK15338, produced around 0.4 g/l isobutyric acid. The engineered strain expressing the mitochondrial isobutyric acid pathway produced around 1.2 g/l hour. Thus, this Example demonstrates that, in accordance with the present disclosure, that expression of a mitochondrial isobutyric acid pathway in *P. kudriavzevii* resulted in production of detectable amounts of isobutyric acid.

Various publications were referenced in this application. The disclosures of these publications in their entireties are hereby incorporated by reference in this application in order to more fully describe the state of the art to which this disclosure pertains.

It should be noted that there are alternative ways of implementing the embodiments disclosed herein. Accordingly, the present embodiments are to be considered as illustrative and not restrictive; various modifications can be made without departing from the spirit of the disclosure. Furthermore, the claims are not to be limited to the details given herein and are entitled their full scope and equivalents thereof.

What is claimed is:

1. A recombinant host cell, comprising:
an isobutyric acid biosynthetic pathway, comprising heterologous nucleic acids encoding an acetolactate synthase, a ketol-acid reductoisomerase, a dihydroxy-acid dehydratase, a branched-chain-2-oxoacid decarboxylase, and an isobutyraldehyde dehydrogenase;
wherein the recombinant host cell is *Pichia* kudriavzevii host cell,
wherein the amino acid sequence of the acetolactate synthase comprises SEQ ID NO: 1 or SEQ ID NO: 19,
wherein the amino acid sequence of the ketol-acid reductoisomerase comprises SEQ ID NO: 2, SEQ ID NO: 20, or SEQ ID NO: 21,
wherein the amino acid sequence of the dihydroxy-acid dehydratase comprises SEQ ID NO: 3 or SEQ ID NO: 22,
wherein the amino acid sequence of the branched-chain-2-oxoacid decarboxylase comprises SEQ ID NO: 4 or SEQ ID NO: 23, and
wherein the amino acid sequence of the isobutyraldehyde dehydrogenase comprises SEQ ID NO: 5 or SEQ ID NO: 24,
wherein the heterologous nucleic acids are expressed in sufficient amounts in the recombinant host cell to enable the recombinant host cell to produce increased amounts of isobutyric acid compared to a wild type host cell.

2. The recombinant host cell of claim 1, wherein the amino acid sequence of the acetolactate synthase comprises SEQ ID NO: 1.

3. The recombinant host cell of claim 1, wherein the amino acid sequence of the ketol-acid reductoisomerase comprises SEQ ID NO: 2 or SEQ ID NO: 21.

4. The recombinant host cell of claim 1, wherein the amino acid sequence of the dihydroxy-acid dehydratase comprises SEQ ID NO: 3.

5. The recombinant host cell of claim 1, wherein the amino acid sequence of the branched-chain-2-oxoacid decarboxylase comprises SEQ ID NO: 4.

6. The recombinant host cell of claim 1, wherein the amino acid sequence of the isobutyraldehyde dehydrogenase comprises SEQ ID NO: 5.

7. The recombinant host cell of claim 1, further comprising: one or more heterologous nucleic acids encoding one or more ancillary proteins; wherein the one or more ancillary proteins functions in redox cofactor recycling, redox cofactor biogenesis, or organic acid transport; and wherein the one or more ancillary proteins is mitochondrial external NADH dehydrogenase, water-forming NADH oxidase, isobutyric acid transporter, or combinations thereof.

8. The recombinant host cell of claim 7, wherein the amino acid sequence of the mitochondrial external NADH dehydrogenase comprises SEQ ID NO: 6.

9. The recombinant host cell of claim 7, wherein the amino acid sequence of the water-forming NADH oxidase comprises SEQ ID NO: 7.

10. The recombinant host cell of claim 7, wherein the isobutyric acid transporter is selected from the group consisting of: *Saccharomyces cerevisiae* PDR12, *Saccharomyces cerevisiae* WAR1, and *Kluyveromyces marxianus* PDC12.

11. The recombinant host cell of claim 1, further comprising a genetic disruption of one or more genes encoding pyruvate decarboxylase, pyruvate dehydrogenase, alcohol dehydrogenase, acetaldehyde dehydrogenase, glycerol-3-phosphate dehydrogenase, or combinations thereof.

12. The recombinant host cell of claim 11, wherein the one or more genes encode a protein comprising the amino acid sequence of SEQ ID NO: 12.

13. The recombinant host cell of claim 11, wherein the one or more genes encodes:
(i) PkPDC1 having the amino sequence of SEQ ID NO: 9, PkPDC6 having the amino sequence of SEQ ID NO: 10, or combinations thereof; or
(ii) PkPDA1 having the amino sequence of SEQ ID NO: 11; or
(iii) PkADH1 having the amino sequence of SEQ ID NO: 13, PkADH6A having the amino sequence of SEQ ID NO: 14, or combinations thereof; or
(iv) PkALD2A having the amino sequence of SEQ ID NO: 15, PkALD2B having the amino sequence of SEQ ID NO: 16, PkALD3 having the amino sequence of SEQ ID NO: 17, PkALD6 having the amino sequence of SEQ ID NO: 18, or combinations thereof.

14. A method for producing isobutyric acid, comprising: culturing the recombinant host cell of claim 1 to produce isobutyric acid.

15. The method of claim 14, wherein the culturing is performed at an oxygen transfer rate greater than 10 mmol/l/hr and/or at a temperature of between about 25° C. and about 45° C.

16. The method of claim 14, wherein the culturing is performed to produce a final fermentation broth pH of about pH 5.

17. An isobutyric acid biosynthetic pathway, comprising at least one heterologous enzyme selected from the group consisting of:
(i) an acetolactate synthase that has at least 60%, at least 70%, at least 80%, at least 90%, or at least 95% amino acid identity to SEQ ID NO: 19;
(ii) a ketol-acid reductoisomerase that has at least 60%, at least 70%, at least 80%, at least 90%, or at least 95% amino acid identity to SEQ ID NO: 21;
(iii) a dihydroxy-acid dehydratase that has at least 60%, at least 70%, at least 80%, at least 90%, or at least 95% amino acid identity to SEQ ID NO: 22;

(iv) a branched-chain-2-oxoacid decarboxylase that has at least 60%, at least 70%, at least 80%, at least 90%, or at least 95% amino acid identity to SEQ ID NO: 23; and
(v) an isobutyraldehyde dehydrogenase that has at least 60%, at least 70%, at least 80%, at least 90%, or at least 95% amino acid identity to SEQ ID NO: 24.

* * * * *